(12) United States Patent
Fan et al.

(10) Patent No.: US 11,884,682 B2
(45) Date of Patent: Jan. 30, 2024

(54) COMPOUNDS AND THEIR USES AS MIF INHIBITORS

(71) Applicant: NANJING IMMUNOPHAGE BIOTECH CO., LTD., Nanjing (CN)

(72) Inventors: Guohuang Fan, Nanjing (CN); Kin Chiu Fong, Nanjing (CN); Hongyu Yang, Nanjing (CN); Jianfei Wang, Nanjing (CN)

(73) Assignee: NANJING IMMUNOPHAGE BIOTECH CO., LTD., Nanjing (CN)

( * ) Notice: Subject to any disclaimer, the term of this patent is extended or adjusted under 35 U.S.C. 154(b) by 0 days.

(21) Appl. No.: 17/053,357

(22) PCT Filed: Jun. 23, 2020

(86) PCT No.: PCT/CN2020/097572
§ 371 (c)(1),
(2) Date: Nov. 6, 2020

(87) PCT Pub. No.: WO2021/258272
PCT Pub. Date: Dec. 30, 2021

(65) Prior Publication Data
US 2021/0403484 A1    Dec. 30, 2021

(51) Int. Cl.
| C07D 498/18 | (2006.01) |
| C07D 413/04 | (2006.01) |
| C07D 405/04 | (2006.01) |
| C07D 413/14 | (2006.01) |
| C07D 471/04 | (2006.01) |
| C07D 271/113 | (2006.01) |

(52) U.S. Cl.
CPC ........ *C07D 498/18* (2013.01); *C07D 271/113* (2013.01); *C07D 405/04* (2013.01); *C07D 413/04* (2013.01); *C07D 413/14* (2013.01); *C07D 471/04* (2013.01)

(58) Field of Classification Search
CPC .......................... C07D 498/18; C07D 271/113; C07D 405/04; C07D 413/04; C07D 413/14; C07D 471/04
See application file for complete search history.

(56) References Cited

U.S. PATENT DOCUMENTS

| 2009/0215742 A1* | 8/2009 | Funk ..................... C07D 207/12 514/211.1 |
| 2018/0179176 A1* | 6/2018 | Jorgensen ............ C07D 403/04 |
| 2019/0002418 A1* | 1/2019 | Watts .................. A61K 31/4245 |
| 2022/0144838 A1* | 5/2022 | Fong ..................... C07D 473/16 |

FOREIGN PATENT DOCUMENTS

| CN | 104958289 A | * | 10/2015 | |
| CN | 105481834 A | * | 4/2016 | |
| DE | 1956510 A1 | * | 5/1971 | |
| WO | WO1997003976 A1 | * | 2/1997 | |
| WO | WO-2008003861 A1 | * | 1/2008 | ........... C07D 409/14 |
| WO | WO-2011062955 A2 | * | 5/2011 | ............. A61K 31/42 |
| WO | WO-2016153023 A1 | * | 9/2016 | ............. A61K 31/41 |
| WO | WO-2017049177 A1 | * | 3/2017 | ........... A61K 31/167 |
| WO | WO-2017076740 A1 | * | 5/2017 | ............. A01N 43/82 |
| WO | WO-2018062978 A1 | * | 4/2018 | ............. A01N 43/50 |
| WO | WO-2020186220 A1 | * | 9/2020 | |

OTHER PUBLICATIONS

Cisneros; J. Am. Chem. Soc. 2016, 138, 27, 8630-8638. https://doi.org/10.1021/jacs.6b04910 (Year: 2016).*
Garai; Current Medicinal Chemistry 2009, 16, 1091-1114. Abstract From CAS. (Year: 2009).*
Goralski; Antimicrobial Agents and Chemotherapy 2016, 60, 3276-3282. https://doi.org/10.1128/AAC.03089-15 (Year: 2016).*
Kok; Drug Discovery Today 2018, 23, 1910-1918. https://doi.org/10.1016/j.drudis.2018.06.017 (Year: 2018).*
Pace; J. Org. Chem. 2007, 72, 20, 7656-7666. https://doi.org/10.1021/jo701306t (Year: 2007).*
Trivedi-Parmar; J. Med. Chem. 2018, 61, 8104-8119. http://dx.doi.org/10.1021/acs.jmedchem.8b00589 (Year: 2018).*
Zapatero; Journal of Biomolecular Screening 2016, 21, 446-458. DOI: 10.1177/1087057116633997 (Year: 2016).*
Chemical Abstracts STN Registry Database, Record for RN 920483-67-6, "2,4-Dimethoxy-N-(5-phenyl-1,3,4-oxadiazol-2-yl) benzamide", Entered STN Feb. 11, 2007. (Year: 2007).*
Chemical Abstracts STN Registry Database, Record for RN 1329658-58-3, "2,4-Dimethoxy-N-[5-(2-thienyl)-1,3,4-oxadiazol-2-yl] benzamide", Entered STN Sep. 7, 2011. (Year: 2011).*
Chemical Abstracts STN Registry Database, Record for RN 1328901-35-4, "2-Fluoro-N-[[5-(2-thienyl)-1,3,4-oxadiazol-2-yl] methyl]benzamide", Entered STN Sep. 6, 2011. (Year: 2011).*
Chemical Abstracts STN Registry Database, Record for RN 1328569-51-2, "2-Methyl-N-[[5-(2-thienyl)-1,3,4-oxadiazol-2-yl] methyl]benzamide", Entered STN Sep. 5, 2011. (Year: 2011).*

(Continued)

*Primary Examiner* — Daniel R Carcanague
(74) *Attorney, Agent, or Firm* — TOMANAGEIP

(57) ABSTRACT

The present invention provides compounds of Formula I which can be used as macrophage migration inhibitory factor (MIF) inhibitors; methods for the production of the compounds of the invention; pharmaceutical compositions comprising the compounds of the invention; as well as uses and methods for treating a disease mediated by MIF by administering the compounds of the invention.

Formula I

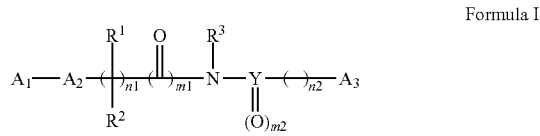

14 Claims, No Drawings

(56) References Cited

OTHER PUBLICATIONS

Chemical Abstracts STN Registry Database, Record for RN 1328752-54-0, "2-Methoxy-N-[[5-(2-thienyl)-1,3,4-oxadiazol-2-yl]methyl]benzamide", Entered STN Sep. 6, 2011. (Year: 2011).*
Chemical Abstracts STN Registry Database, Record for RN 1327985-15-8, "2-Chloro-N-[[5-(2-thienyl)-1,3,4-oxadiazol-2-yl]methyl]benzamide", Entered STN Sep. 4, 2011. (Year: 2011).*
Chemical Abstracts STN Registry Database, Record for RN 1327765-23-0, "2,6-Dimethoxy-N-[[5-(2-thienyl)-1,3,4-oxadiazol-2-yl]methyl]benzamide", Entered STN Sep. 4, 2011. (Year: 2011).*
Chemical Abstracts STN Registry Database, Record for RN 1327677-75-7, "N-[[5-(2-Thienyl)-1,3,4-oxadiazol-2-yl]methyl]cyclohexanecarboxamide", Entered STN Sep. 4, 2011. (Year: 2011).*
Chemical Abstracts STN Registry Database, Record for RN 1323346-30-0, "2,4-Dimethoxy-N-[5-(3-thienyl)-1,3,4-oxadiazol-2-yl]benzamide", Entered STN Aug. 25, 2011. (Year: 2011).*
Chemical Abstracts STN Registry Database, Record for RN 865288-08-0, "N-[5-(2-Thienyl)-1,3,4-oxadiazol-2-yl] benzeneacetamide", Entered STN Oct. 14, 2005. (Year: 2005).*
Chemical Abstracts STN Registry Database, Record for RN 878027-43-1, "Ethyl a-(benzoylamino)-5-phenyl-1,3,4-oxadiazole-2-acetate", Entered STN Mar. 24, 2006. (Year: 2006).*
Golovchenko; Russian Journal of General Chemistry 2005, 75, 425-431. https://doi.org/10.1007/s11176-005-0244-8 (Year: 2005).*
Chemical Abstracts STN Registry Database, Record for RN 1219157-87-5, "Methyl 5-(4-fluorophenyl)-α-[(4-methylbenzoyl) amino]-1,3,4- oxadiazole-2-acetate", Entered STN Apr. 15, 2010. (Year: 2010).*
Yang; ACS Comb. Sci. 2015, 17, 732-741, with supporting information, 173 pages. http://dx.doi.org/10.1021/acscombsci.5b00140 ( Year: 2015).*
Chemical Abstracts STN Registry Database, record for RN 900325-53-3, "5-(3-Chlorophenyl)-N-(2-pyridinylmethyl)-1,3,4-oxadiazole-2-carboxamide", Entered STN Aug. 10, 2006. (Year: 2006).*
Chemical Abstracts STN Registry Database, record for RN 1242939-15-6, "N-Cyclohexyl-5-(4-methylphenyl)-1,3,4-oxadiazole-2-acetamide", Entered STN Sep. 27, 2010. (Year: 2010).*
Martinez-Grau; Bioorganic & Medicinal Chemistry Letters 2018, 28, 1758-1764. https://doi.org/10.1016/j.bmcl.2018.04.028 (Year: 2018).*
Chemical Abstracts STN Registry Database, Record for RN 2330779-62-7, "N,5-Diphenyl-1,3,4-oxadiazole-2-acetamide", Entered STN Jun. 12, 2019. (Year: 2019).*

* cited by examiner

COMPOUNDS AND THEIR USES AS MIF INHIBITORS

BACKGROUND OF THE INVENTION

Technical Field

The present invention relates to novel compounds; methods for the production of the compounds of the invention; pharmaceutical compositions comprising the compounds of the invention; as well as uses and methods for treating a disease mediated by macrophage migration inhibitory factor (MIF) by administering the compounds of the invention. In particular, the compounds of the invention may be used as MIF inhibitors.

Description of Related Art

Macrophage migration inhibitory factor (MIF) was originally identified as a cytokine released from active T cells to inhibit the random movement of macrophages. It is secreted by epithelial cells, endothelial cells, lymphocytes, monocytes, and macrophages, showing that it has a role in innate and acquired immunity. In humans, the MIF gene is found on chromosome 22q11.2 and codes for an evolutionarily conserved protein consisting of 115 amino acids. The MIF protein has a molecular weight of 12.5 kD in its monomeric form. When the MIF protein is activated, MIF forms a trimer composed of three identical subunits, with each monomer containing two antiparallel α-helices that pack against a four-stranded β-sheet. MIF demonstrates chemokine-like function and was identified as a ligand of CD74 which forms complex with both CXCR2 and CXCR4. Binding of MIF to these receptors enhances monocyte recruitment and leukocyte chemotaxis. The inflammatory cascade relies on the activation of CXCR2 and CD74, suggesting that MIF operates via a functional CXCR2/CD74 complex.

MIF has various biological roles, with the most significant being inflammation and immunity. MIF counter-regulates the actions of glucocorticoids, which are natural steroid hormones produced by the adrenal glands during cellular stress that possess as anti-inflammatory effects. MIF may stimulate the expression of other cytokines involved in inflammation. Inflammation is needed for the survival of organisms, but when it is incorrectly regulated, it may contribute to tumorigenesis. MIF plays a role in both innate and adaptive immunity and is constitutively expressed by monocytes, macrophages, dendritic cells, B cells, neutrophils, eosinophils, mast cells, and basophils. It promotes the stimulation and proliferation of T cells in response to foreign agents and acts as a regulator of responses to infections by increasing the expression of TLR4. Activated T cells release MIF to inhibit glucocorticoid-mediated interleukin-2 and interferon-γ production. Since circulating glucocorticoid levels are increased during infection and inflammation, MIF exerts its immunosuppressive effects, which enable the primary immune response and reduce the need for steroid therapy. MIF is also reported to possess enzymatic activity, and it converts D-dopachrome in 5,6-dihydroxy-2-carboxylic acid (DHICA). Although identification of DHICA as a true biological MIF substrate sheds light on this mechanism of action, the role of MIF enzymatic activity is not fully understood.

MIF is a pluripotent and pleiotropic cytokine expressed in numerous human malignancies such as glioblastomas, lung cancer, breast cancer, gastric cancer, bladder cancer, and melanoma. MIF has been shown to contribute to many different forms of cancer in multiple studies. First, MIF is a regulator of the p53 signaling pathway and can physically interact with p53. MIF suppresses the activity of p53, which leads to the deregulation of the normal cell cycle. Since MIF functionally inactivates p53, cell cycle arrest and apoptosis do not occur. Second, MIF is involved in the phosphoinositide-3-kinase (PI3K)/Akt pathway, which plays a key role in the development of tumors. Activation of this pathway allows crucial cells to prevent apoptosis. Previous studies have shown that MIF and CD74 initiate Akt activation and when MIF is overexpressed, it causes crucial cells to progress through the cell cycle via the PI3K/Akt pathway. Third, MIF plays a role in angiogenesis. When MIF is highly expressed, vascular endothelial growth factor (VEGF), hypoxia inducible factor 1 (HIF-1), and other angiogenic factors are responsible for the creation of new blood vessels. Forth, MIF leads to the metastasis of tumor cells by decreasing the expression of E-cadherin and increasing the expression of N-cadherin. The decreased expression of E-cadherin also promotes epithelial mesenchymal transition (EMT) and can lead to the establishment of secondary tumors. EMT is a process that modulate epithelial cells to acquire characteristics of mesenchymal cells, which in turn leads to invasion and metastasis.

In addition to the oncology area, MIF is also a pleiotropic inflammatory cytokine with upstream regulatory roles in innate and adaptive immunity, and is implicated in the pathogenesis of autoimmune diseases including multiple sclerosis (MS), rheumatoid arthritis (RA) and systemic lupus erythematosus (SLE). MIF is significantly up-regulated in the serum of MS, RA and SLE patients and animal models. MIF inhibition has been shown to improve both ex vivo and in vivo features of the autoimmune diseases.

The important role of MIF in cancer development and autoimmune diseases suggests that targeted inhibition of MIF is a potential therapeutic approach for the treatment of cancer, autoimmune diseases, and other inflammatory diseases. One of the most important strategies targeting MIF is to develop small molecule inhibitors against MIF, which have demonstrated promising preclinical efficacy.

SUMMARY OF THE INVENTION

The present invention provides novel compounds that function as MIF inhibitors.

In one aspect, the invention provides a compound of formula I:

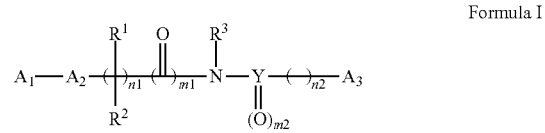

Formula I wherein
$A_1$ is a 5 or 6 membered carbocycle or heterocycle,
wherein $A_1$ is optionally substituted with 0, 1, 2 or 3 substituents independently selected from the group consisting of OH, halogen, or $C_{1-6}$ alkyl;
$A_2$ is selected from the group consisting of k,

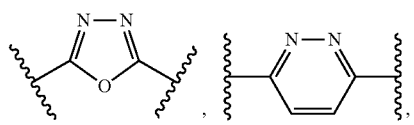

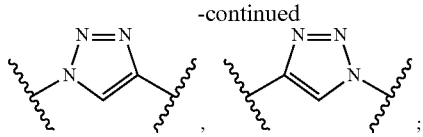

n1 is 0 or 1, when n1 is 0, $R^1$ and $R^2$ are absent, when n1 is 1, each of $R^1$ and $R^2$ independently is selected from the group consisting of H, $C_{1-6}$ alkyl, or $R^1$ and $R^2$ together with the carbon atom to which they are bonded, form a $C_3$-$C_6$ cycloalkyl;

m1 is 0 or 1, m2 is 0, 1 or 2, when m1 is 0, m2 is 1, Y is C; when m1 is 0, m2 is 2, Y is S; when m1 is 1, Y is absent, and m2 is 0;

$R^3$ is H, methylene, or $C_{1-6}$ alkyl;

n2 is 0 or 1;

$A_3$ is a 5 or 6 membered carbocycle or heterocycle, wherein $A_3$ is optionally substituted with 0, 1, 2 or 3 substituents independently selected from the group consisting of OH, halogen, $C_{1-6}$ alkyl, $C_{1-6}$ alkoxy,

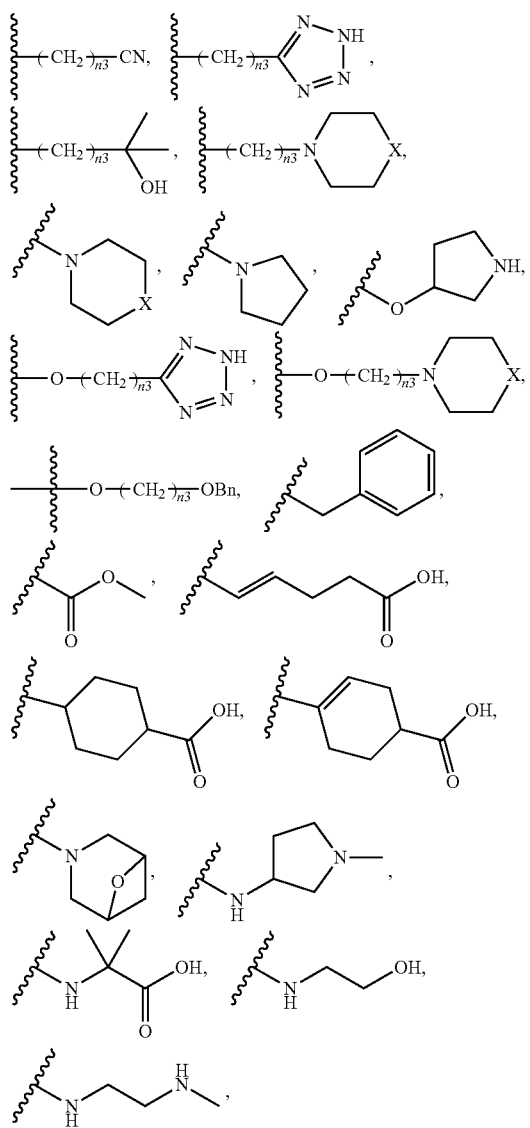

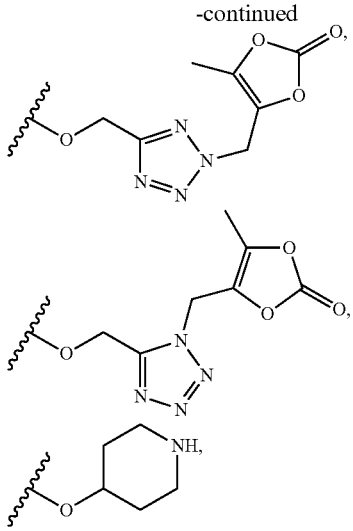

wherein

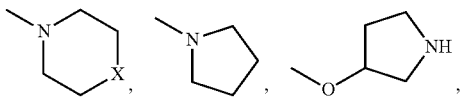

$C_{1-6}$ alkoxy may be optionally substituted with 0, 1, 2 substituents independently selected from the group consisting of halogen, OH, $CH_3$, $OCH_3$, COOH, $NH_2$, $NH(C_{1-6}$ alkyl), $N(C_{1-6}$ alkyl$)_2$, wherein n3 is 0, 1, 2, 3, or 4, wherein X is $CH_2$, NH, or O;

when n2 is 0, $R^3$ is methylene, and the $A_3$ is optionally substituted with $C_{1-6}$ alkyl, the $R^3$ and the $C_{1-6}$ alkyl together with the atoms to which they are attached, form a 6- to 8-membered heterocycle;

or a pharmaceutically acceptable salt, ester, stereoisomer, tautomer, solvate, prodrug, or combination thereof.

In some embodiments, $A_3$ is optionally substituted with 0, 1 or 2 substituents independently selected from the group consisting of

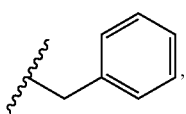 [SMILES: *Cc1ccccc1]

OH, methylene, F, Cl, Br, —$CH_3$, —OMe, —OEt, OBn, —$OCF_3$,

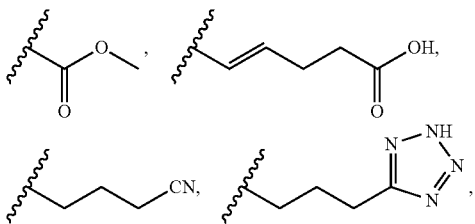

-continued

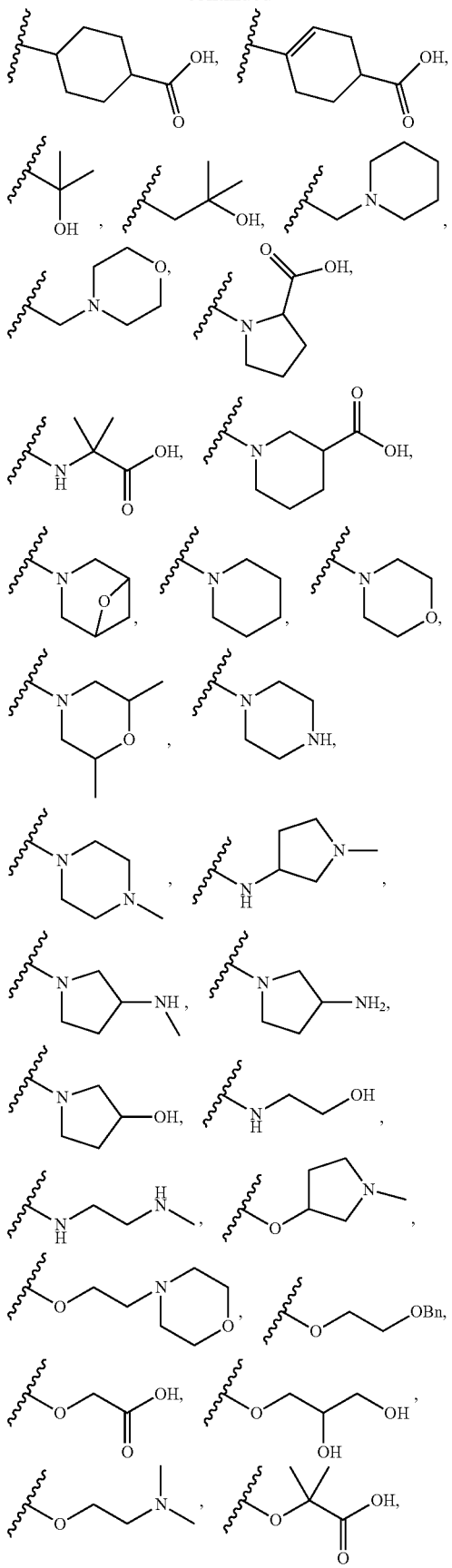

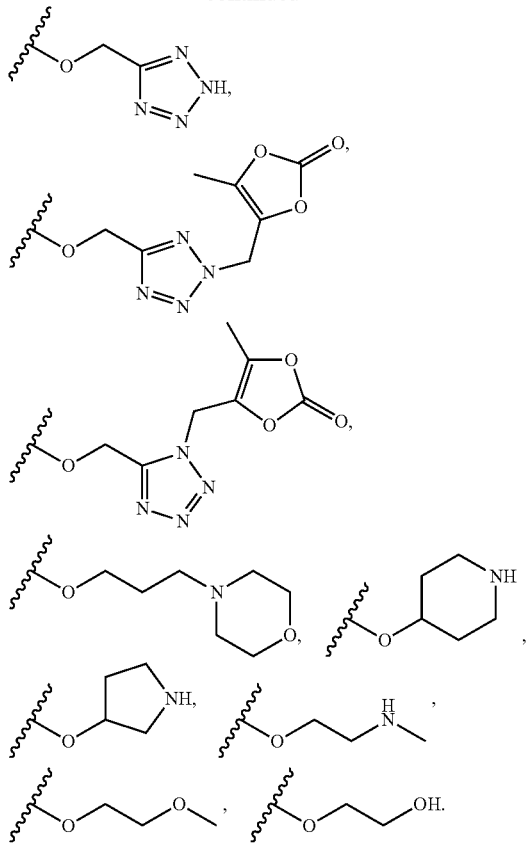

In some embodiments, $A_2$ is

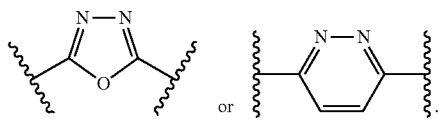 [SMILES: *c1nnc(*)o1 ; *c1ccc(*)nn1]

In one embodiment, n1 is 1;

$A_1$ is a phenyl or is independently selected from the group consisting of

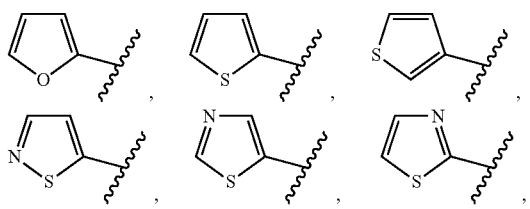

wherein $A_1$ is optionally substituted with 0 or 1 substituents selected from the group consisting of OH, F, Cl, or methyl.

In a preferred embodiment, m1 is 0, m2 is 1, Y is C.

In a more preferred embodiment, n2 is 0;

$A_3$ is selected from phenyl, pyridinyl, cyclohexyl, pyrrolidinyl, or piperidinyl.

In a most preferred embodiment, $A_3$ is selected from pyridinyl, cyclohexyl, pyrrolidinyl, or piperidinyl;

wherein A₃ is optionally substituted with 0, 1, 2 substituents independently selected from the group consisting of OH, halogen, $C_{1-6}$ alkyl, $C_{1-6}$ alkoxy, or

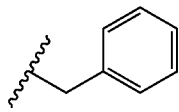

In this case, $C_{1-6}$ alkyl may be —CH₃, and $C_{1-6}$ alkoxy may be —OMe.

In an alternative most preferred embodiment, A₃ is phenyl, wherein A₃ is optionally substituted with 0, 1, 2 substituents independently selected from the group consisting of OH, methylene, F, Cl, Br, —CH₃, —OMe, —OEt, OBn, —OCF₃,

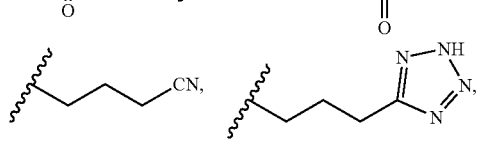

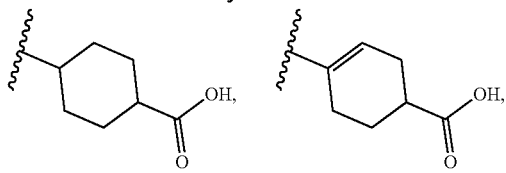

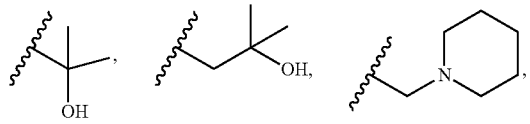

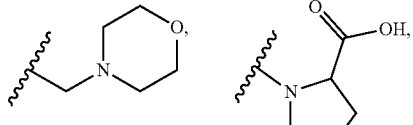

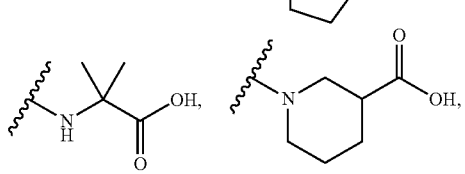

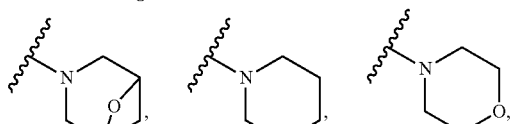

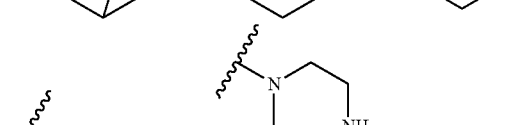

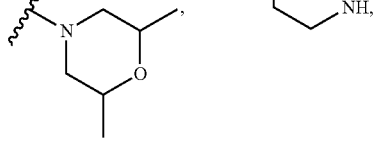

-continued

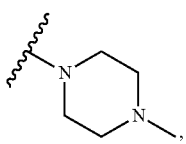

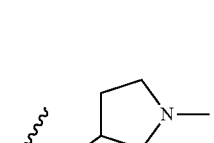 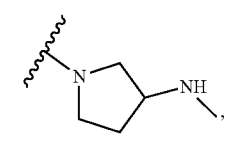

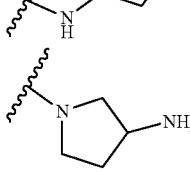 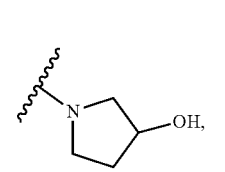

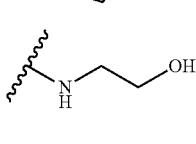 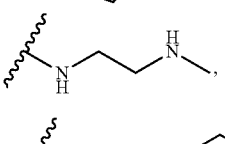

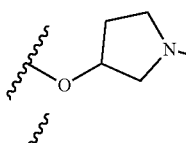 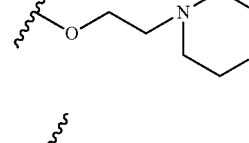

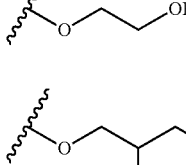 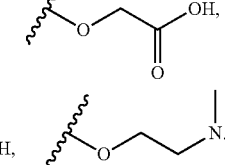

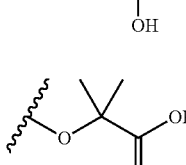 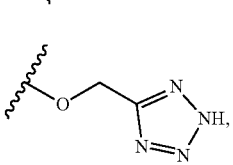

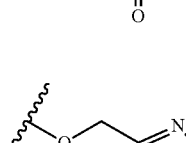 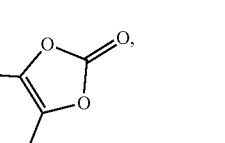

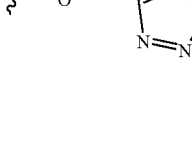 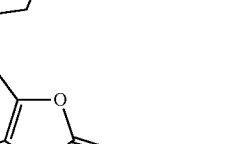

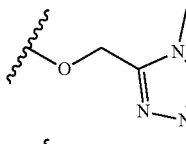 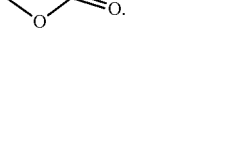

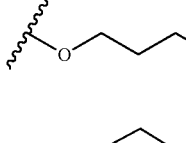 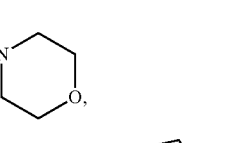

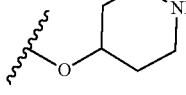 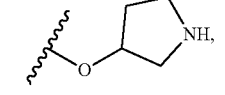

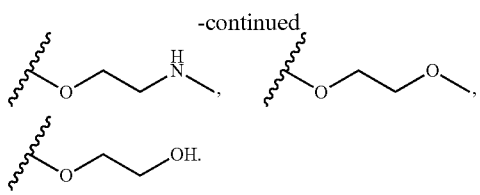

In another preferred embodiment, m1 is 0, m2 is 2, Y is S;

n2 is 0;

$A_3$ is selected from phenyl, pyridinyl, cyclohexyl, pyrrolidinyl, or piperidinyl.

In a more preferred embodiment, $A_3$ is selected from pyridinyl, cyclohexyl, pyrrolidinyl, or piperidinyl;

wherein $A_3$ is optionally substituted with 0, 1, 2 substituents independently selected from the group consisting of OH, halogen, $C_{1-6}$ alkyl, $C_{1-6}$ alkoxy, or

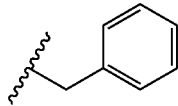

In this case, $C_{1-6}$ alkyl may be —$CH_3$, and $C_{1-6}$ alkoxy may be —OMe.

In another embodiment, n1 is 0;

$A_1$ is a phenyl or is independently selected from the group consisting of

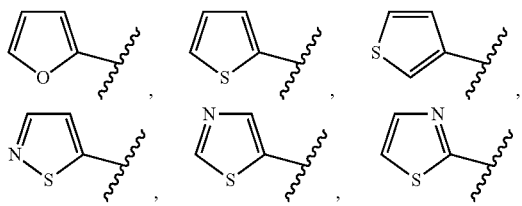

wherein $A_1$ is optionally substituted with 0 or 1 substituents selected from the group consisting of OH, F, Cl, or methyl.

In a preferred embodiment, m1 is 0, m2 is 1, Y is C.

In a more preferred, n2 is 0;

$A_3$ is selected from phenyl, pyridinyl, cyclohexyl, pyrrolidinyl, or piperidinyl.

In a most preferred embodiment, $A_3$ is selected from pyridinyl, cyclohexyl, pyrrolidinyl, or piperidinyl;

wherein $A_3$ is optionally substituted with 0, 1, 2 substituents independently selected from the group consisting of OH, halogen, $C_{1-6}$ alkyl, $C_{1-6}$ alkoxy, or

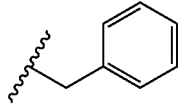

In this case, $C_{1-6}$ alkyl may be —$CH_3$, and $C_{1-6}$ alkoxy may be —OMe.

In an alternative preferred embodiment, m1 is 0, m2 is 2, Y is S, n2 is 0;

$A_3$ is selected from phenyl, pyridinyl, cyclohexyl, pyrrolidinyl, or piperidinyl.

In a more preferred embodiment, $A_3$ is selected from pyridinyl, cyclohexyl, pyrrolidinyl, or piperidinyl;

wherein $A_3$ is optionally substituted with 0, 1, 2 substituents independently selected from the group consisting of OH, halogen, $C_{1-6}$ alkyl, $C_{1-6}$ alkoxy, or

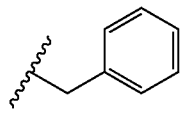

In this case, $C_{1-6}$ alkyl may be —$CH_3$, and $C_{1-6}$ alkoxy may be —OMe.

In still another embodiment, n1 is 0 or 1; m1 is 1, Y is absent, and m2 is 0.

In a preferred embodiment, n2 is 0, $A_1$ is a phenyl or is independently selected from the group consisting of

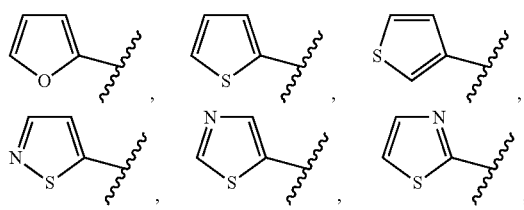

wherein $A_1$ is optionally substituted with 0 or 1 substituents selected from the group consisting of OH, F, Cl, or methyl.

In a more preferred embodiment, $A_3$ is selected from phenyl, pyridinyl, cyclohexyl, pyrrolidinyl, or piperidinyl.

In still another embodiment, $A_1$ is a phenyl or is independently selected from the group consisting of

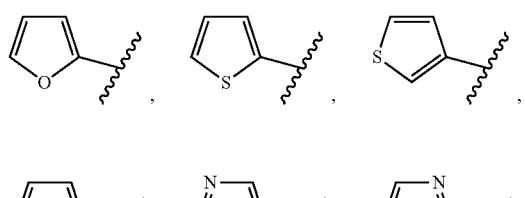

wherein $A_1$ is optionally substituted with 0 or 1 substituents selected from the group consisting of OH, F, Cl, or methyl;

n1 is 0 or 1;

m1 is 0, m2 is 1, Y is C;

n2 is 0;

$R^3$ is methylene; $A_3$ is $C_{1-6}$ alkyl-substituted phenyl; the methylene and the $C_{1-6}$ alkyl together with the atoms to which they are attached, form a 6- to 8-membered heterocycle.

In a preferred embodiment, wherein n1 is 1; R³ is methylene; A₃ is methyl-substituted phenyl; and

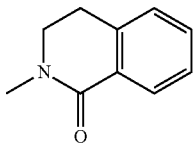

is

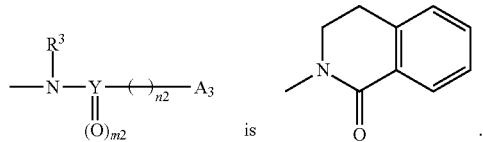

which is optionally substituted with 0, 1 or 2 substituents independently selected from the group consisting of halogen,

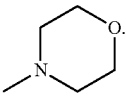

In yet another embodiment, the compound is selected from

| No | Structure | Name |
|---|---|---|
| 1 | 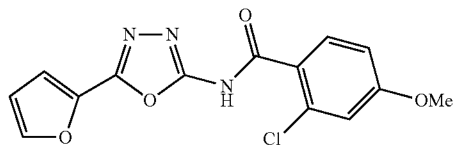 [SMILES: COc1ccc(C(=O)Nc2nnc(-c3ccco3)o2)c(Cl)c1] | 2-chloro-N-(5-(furan-2-yl)-1,3,4-oxadiazol-2-yl)-methoxybenzamide |
| 2 | 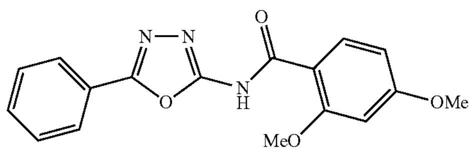 [SMILES: COc1ccc(C(=O)Nc2nnc(-c3ccccc3)o2)c(OC)c1] | 2,4-dimethoxy-N-(5-phenyl-1,3,4-oxadiazol-2-yl)benzamide |
| 3 | 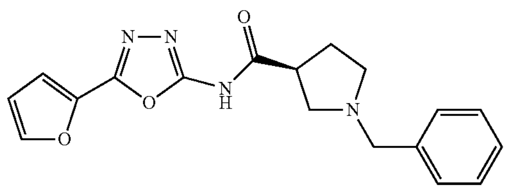 [SMILES: O=C(Nc1nnc(-c2ccco2)o1)[C@H]1CCN(Cc2ccccc2)C1] | (S)-1-benzyl-N-(5-(furan-2-yl)-1,3,4-oxadiazol-2-yl)pyrrolidine-3-carboxamide |
| 4 | 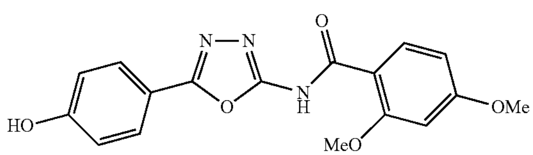 [SMILES: COc1ccc(C(=O)Nc2nnc(-c3ccc(O)cc3)o2)c(OC)c1] | N-(5-(4-hydroxyphenyl)-1,3,4-oxadiazol-2-yl)-2,4-dimethoxybenzamide |
| 5 | 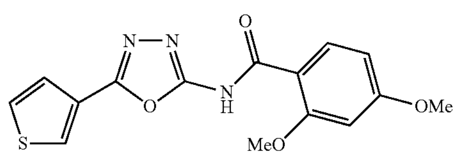 [SMILES: COc1ccc(C(=O)Nc2nnc(-c3ccsc3)o2)c(OC)c1] | 2,4-dimethoxy-N-(5-(thiophen-3-yl)-1,3,4-oxadiazol-2-yl)benzamide |
| 6 | 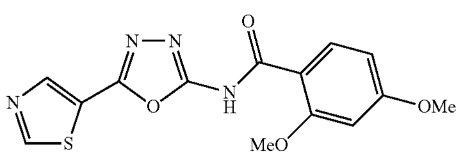 [SMILES: COc1ccc(C(=O)Nc2nnc(-c3cncs3)o2)c(OC)c1] | 2,4-dimethoxy-N-(5-(thiazol-5-yl)-1,3,4-oxadiazol-2-yl)benzamide |
| 7 | 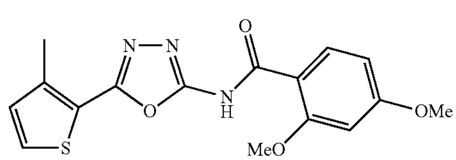 [SMILES: COc1ccc(C(=O)Nc2nnc(-c3sccc3C)o2)c(OC)c1] | 2,4-dimethoxy-N-(5-(3-methylthiophen-2-yl)-1,3,4-oxadiazol-2-yl)benzamide |
| 8 | 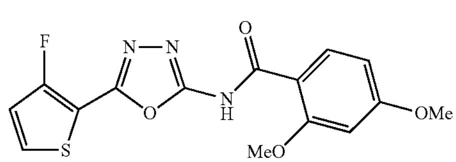 [SMILES: COc1ccc(C(=O)Nc2nnc(-c3sccc3F)o2)c(OC)c1] | N-(5-(3-fluorothiophen-2-yl)-1,3,4-oxadiazol-2-yl)-2,4-dimethoxybenzamide |

-continued

| No | Structure | Name |
|---|---|---|
| 9 | 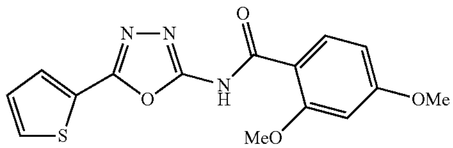 [SMILES: COc1ccc(C(=O)Nc2nnc(-c3cccs3)o2)c(OC)c1] | 2,4-dimethoxy-N-(5-(thiophen-2-yl)-1,3,4-oxadiazol-2-yl)benzamide |
| 10 | 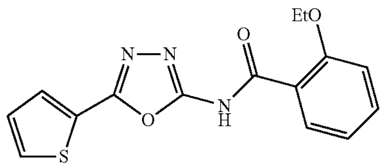 [SMILES: CCOc1ccccc1C(=O)Nc1nnc(-c2cccs2)o1] | 2-ethoxy-N-(5-(thiophen-2-yl)-1,3,4-oxadiazol-2-yl)benzamide |
| 11 | 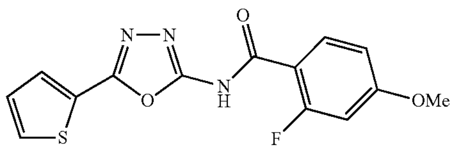 [SMILES: COc1ccc(C(=O)Nc2nnc(-c3cccs3)o2)c(F)c1] | 2-fluoro-4-methoxy-N-(5-(thiophen-2-yl)-1,3,4-oxadiazol-2-yl)benzamide |
| 12 | 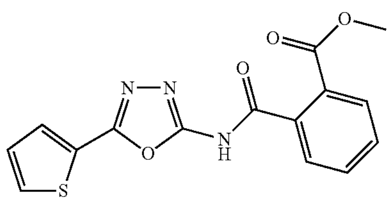 [SMILES: COC(=O)c1ccccc1C(=O)Nc1nnc(-c2cccs2)o1] | methyl 2-((5-(thiophen-2-yl)-1,3,4-oxadiazol-2-yl)carbamoyl)benzoate |
| 13 | 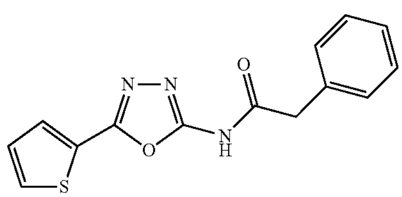 [SMILES: O=C(Cc1ccccc1)Nc1nnc(-c2cccs2)o1] | 2-phenyl-N-(5-(thiophen-2-yl)-1,3,4-oxadiazol-2-yl)acetamide |
| 14 | 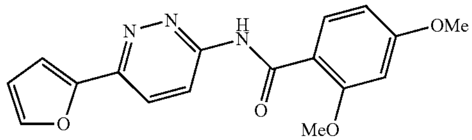 [SMILES: COc1ccc(C(=O)Nc2ccc(-c3ccco3)nn2)c(OC)c1] | N-(6-(furan-2-yl)pyridazin-3-yl)-2,4-dimethoxybenzamide |
| 15 | 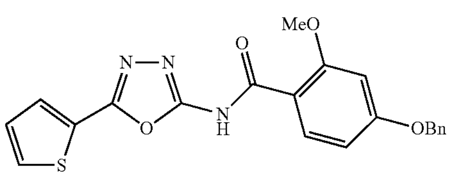 [SMILES: COc1cc(OCc2ccccc2)ccc1C(=O)Nc1nnc(-c2cccs2)o1] | 4-(benzyloxy)-2-methoxy-N-(5-(thiophen-2-yl)-1,3,4-oxadiazol-2-yl)benzamide |
| 16 | 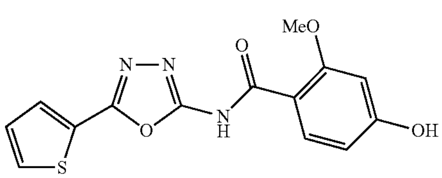 [SMILES: COc1cc(O)ccc1C(=O)Nc1nnc(-c2cccs2)o1] | 4-hydroxy-2-methoxy-N-(5-(thiophen-2-yl)-1,3,4-oxadiazol-2-yl)benzamide |
| 17 | 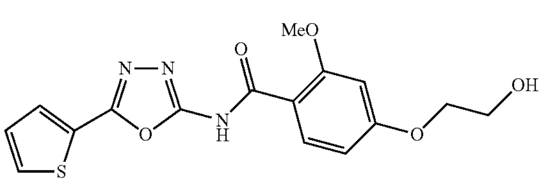 [SMILES: COc1cc(OCCO)ccc1C(=O)Nc1nnc(-c2cccs2)o1] | 4-(2-hydroxyethoxy)-2-methoxy-N-(5-(thiophen-2-yl)-1,3,4-oxadiazol-2-yl)benzamide |

-continued

| No | Structure | Name |
|---|---|---|
| 18 | 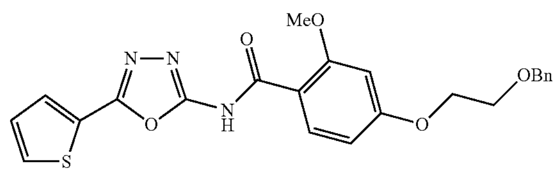 [SMILES: COc1cc(OCCOCc2ccccc2)ccc1C(=O)Nc1nnc(-c2cccs2)o1] | 4-(2-(benzyloxy)ethoxy)-2-methoxy-N-(5-(thiophen-2-yl)-1,3,4-oxadiazol-2-yl)benzamide |
| 19 | 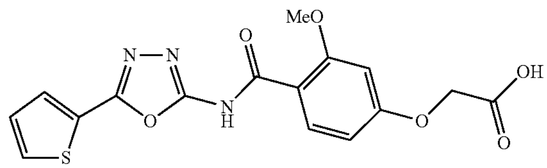 [SMILES: COc1cc(OCC(=O)O)ccc1C(=O)Nc1nnc(-c2cccs2)o1] | 2-(3-methoxy-4-((5-(thiophen-2-yl)-1,3,4-oxadiazol-2-yl)carbamoyl)phenoxy)acetic acid |
| 20 | 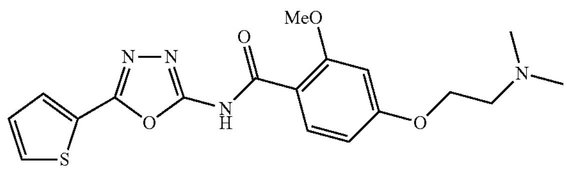 [SMILES: COc1cc(OCCN(C)C)ccc1C(=O)Nc1nnc(-c2cccs2)o1] | 4-(2-(dimethylamino)ethoxy)-2-methoxy-N-(5-(thiophen-2-yl)-1,3,4-oxadiazol-2-yl)benzamide |
| 21 | 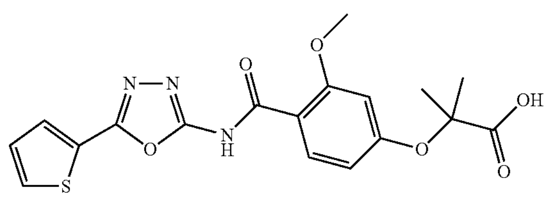 [SMILES: COc1cc(OC(C)(C)C(=O)O)ccc1C(=O)Nc1nnc(-c2cccs2)o1] | 2-(3-methoxy-4-((5-(thiophen-2-yl)-1,3,4-oxadiazol-2-yl)carbamoyl)phenoxy)-2-methyl propanoic acid |
| 22 | 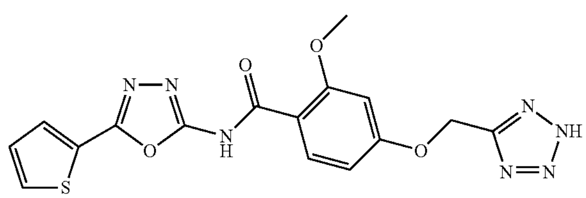 [SMILES: COc1cc(OCc2nn[nH]n2)ccc1C(=O)Nc1nnc(-c2cccs2)o1] | 4-((2H-tetrazol-5-yl)methoxy)-2-methoxy-N-(5-(thiophen-2-yl)-1,3,4-oxadiazol-2-yl)benzamide |
| 23 | 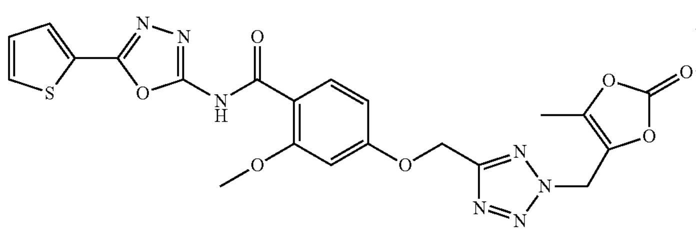 [SMILES: COc1cc(OCc2nnn(Cc3oc(=O)oc3C)n2)ccc1C(=O)Nc1nnc(-c2cccs2)o1] | 2-methoxy-4-((2-((5-methyl-2-oxo-1,3-dioxol-4-yl)methyl)-2H-tetrazol-5-yl)methoxy)-N-(5-(thiophen-2-yl)-1,3,4-oxadiazol-2-yl)benzamide |
| 24 | 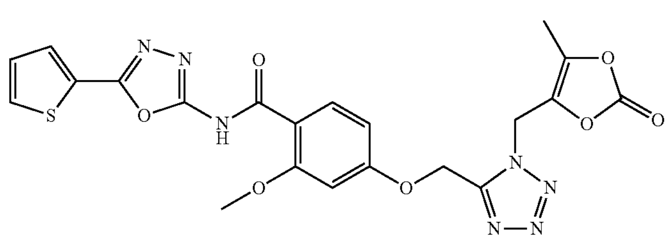 [SMILES: COc1cc(OCc2nnnn2Cc2oc(=O)oc2C)ccc1C(=O)Nc1nnc(-c2cccs2)o1] | 2-methoxy-4-((1-((5-methyl-2-oxo-1,3-dioxol-4-yl)methyl)-1H-tetrazol-5-yl)methoxy)-N-(5-(thiophen-2-yl)-1,3,4-oxadiazol-2-yl)benzamide |
| 25 | 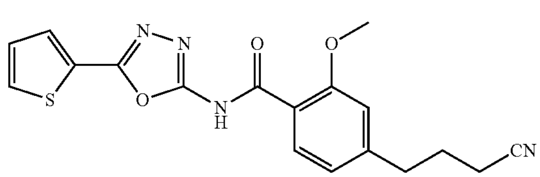 [SMILES: COc1cc(CCCC#N)ccc1C(=O)Nc1nnc(-c2cccs2)o1] | 4-(3-cyanopropyl)-2-methoxy-N-(5-(thiophen-2-yl)-1,3,4-oxadiazol-2-yl)benzamide |

-continued

| No | Structure | Name |
|---|---|---|
| 26 | 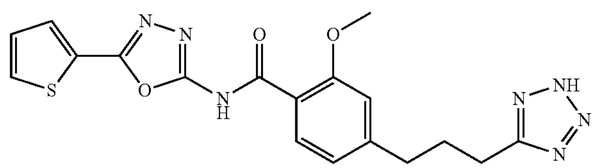 [SMILES: COc1cc(CCCc2nn[nH]n2)ccc1C(=O)Nc1nnc(-c2cccs2)o1] | 4-(3-(2H-tetrazol-5-yl)propyl)-2-methoxy-N-(5-(thiophen-2-yl)-1,3,4-oxadiazol-2-yl)benzamide |
| 27 | 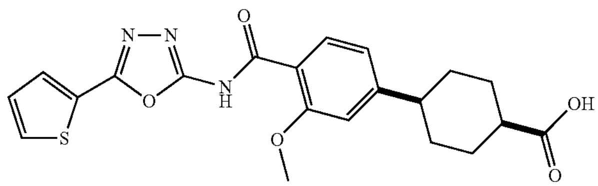 | Cis-4-(3-methoxy-4-((5-(thiophen-2-yl)-1,3,4-oxadiazol-2-yl)carbamoyl)phenyl)cyclohexane-1-carboxylic acid |
| 28 | 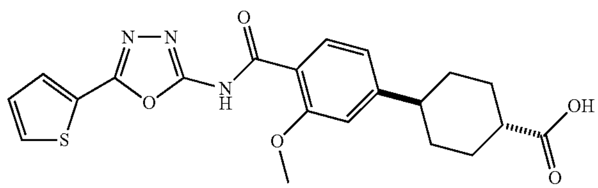 | Trans-4-(3-methoxy-4-((5-(thiophen-2-yl)-1,3,4-oxadiazol-2-yl)carbamoyl)phenyl)cyclohexane-1-carboxylic acid |
| 29 | 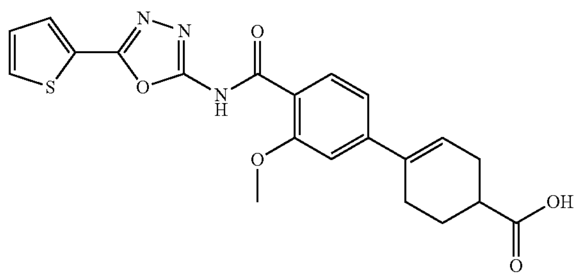 [SMILES: COc1cc(C2=CCC(C(=O)O)CC2)ccc1C(=O)Nc1nnc(-c2cccs2)o1] | 3'-methoxy-4'-((5-(thiophen-2-yl)-1,3,4-oxadiazol-2-yl)carbamoyl)-2,3,4,5-tetrahydro-[1,1'-biphenyl]-4-carboxylic acid |
| 30 | 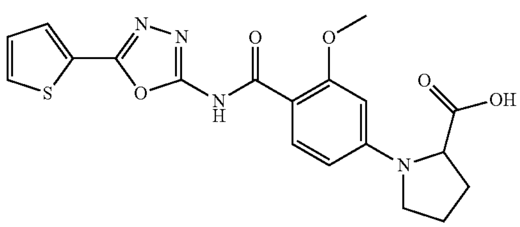 [SMILES: COc1cc(N2CCCC2C(=O)O)ccc1C(=O)Nc1nnc(-c2cccs2)o1] | (3-methoxy-4-((5-(thiophen-2-yl)-1,3,4-oxadiazol-2-yl)carbamoyl)phenyl)proline |
| 31 | 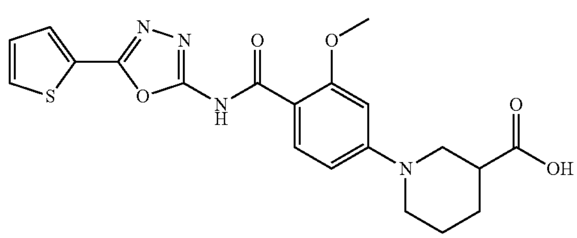 [SMILES: COc1cc(N2CCCC(C(=O)O)C2)ccc1C(=O)Nc1nnc(-c2cccs2)o1] | 1-(3-methoxy-4-(((5-(thiophen-2-yl)-1,3,4-oxadiazol-2-yl)carbamoyl)phenyl)piperidine-3-carboxylic acid |
| 32 | 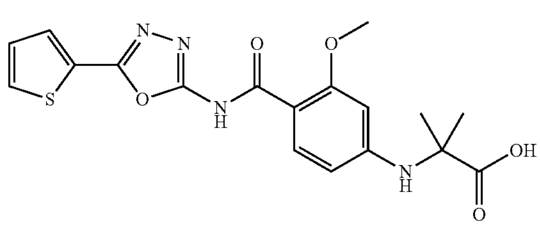 [SMILES: COc1cc(NC(C)(C)C(=O)O)ccc1C(=O)Nc1nnc(-c2cccs2)o1] | 2-((3-metboxy-4-((5-(thiophen-2-yl)-1,3,4-oxadiazol-2-yl)carbamoyl)phenyl)amino)-2-methylpropanoic acid |

-continued

| No | Structure | Name |
|---|---|---|
| 33 | 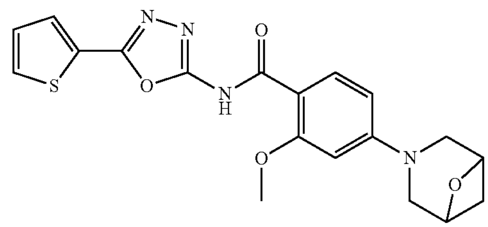 [SMILES: COc1cc(N2CC3CC(C2)O3)ccc1C(=O)Nc1nnc(-c2cccs2)o1] | 4-(6-oxa-3-azabicyclo[3.1.1]heptan-3-yl)-2-methoxy-N-(5-(thiophen-2-yl)-1,3,4-oxadiazol-2-yl)benzamide |
| 34 | 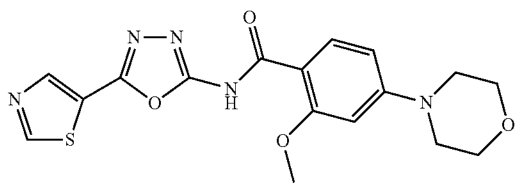 [SMILES: COc1cc(N2CCOCC2)ccc1C(=O)Nc1nnc(-c2cncs2)o1] | 2-methoxy-4-morpholino-N-(5-(thiazol-5-yl)-1,3,4-oxadiazol-2-yl)benzamide |
| 35 | 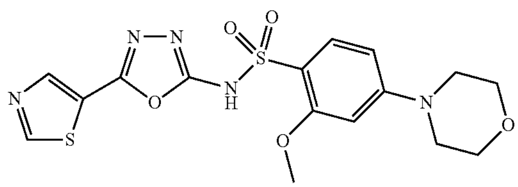 [SMILES: COc1cc(N2CCOCC2)ccc1S(=O)(=O)Nc1nnc(-c2cncs2)o1] | 2-methoxy-4-morpholino-N-(5-thiazol-5-yl)-1,3,4-oxadiazol-2-yl)benzenesafonamide |
| 36 | 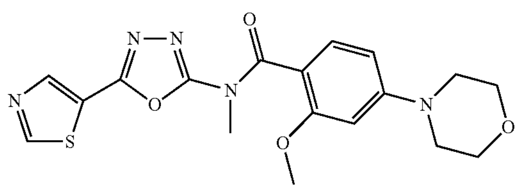 [SMILES: COc1cc(N2CCOCC2)ccc1C(=O)N(C)c1nnc(-c2cncs2)o1] | 2-methoxy-N-methyl-4-morpholino-N-(5-(thiazol-5-yl)-1,3,4-oxadiazol-2-yl)benzamide |
| 37 | 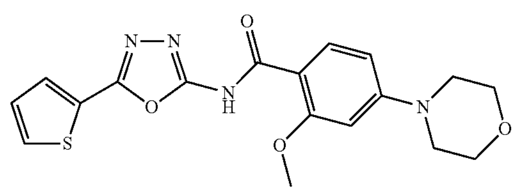 [SMILES: COc1cc(N2CCOCC2)ccc1C(=O)Nc1nnc(-c2cccs2)o1] | 2-methoxy-4-morpholino-N-(5-(thiophen-2-yl)-1,3,4-oxadiazol-2-yl)benzamide |
| 38 | 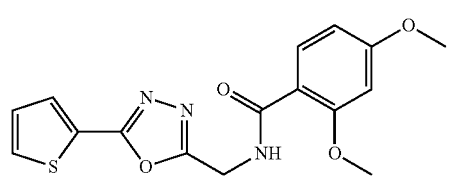 [SMILES: COc1ccc(C(=O)NCc2nnc(-c3cccs3)o2)c(OC)c1] | 2,4-dimethoxy-N-((5-(thiophen-2-yl)-1,3,4-oxadiazol-2-yl)methyl)benzamide |
| 39 | 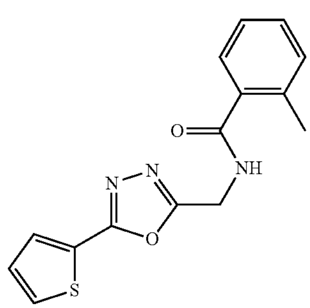 [SMILES: Cc1ccccc1C(=O)NCc1nnc(-c2cccs2)o1] | 2-methyl-N-((5-(thiophen-2-yl)-1,3,4-oxadiazol-2-yl)methyl)benzamide |

-continued

| No | Structure | Name |
|---|---|---|
| 40 | 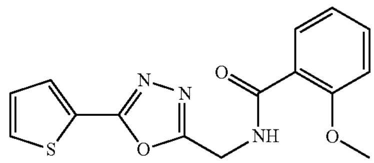 [SMILES: COc1ccccc1C(=O)NCc1nnc(-c2cccs2)o1] | 2-methoxy-N-((5-(thiophen-2-yl)-1,3,4-oxadiazol-2-yl)methyl)benzamide |
| 41 | 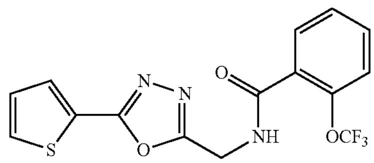 | N-((5-(thiophen-2-yl)-1,3,4-oxadiazol-2-yl)methyl)-2-(trifluoromethoxy)benzamide |
| 42 | 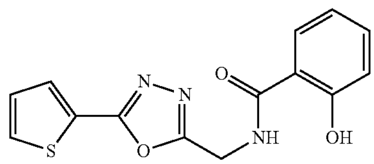 [SMILES: O=C(NCc1nnc(-c2cccs2)o1)c1ccccc1O] | 2-hydroxy-N-((5-(thiophen-2-yl)-1,3,4-oxadiazol-2-yl)methyl)benzamide |
| 43 | 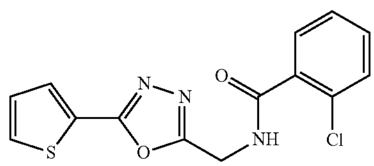 [SMILES: O=C(NCc1nnc(-c2cccs2)o1)c1ccccc1Cl] | 2-chloro-N-((5-(thiophen-2-yl)-1,3,4-oxadiazol-2-yl)methyl)benzamide |
| 44 | 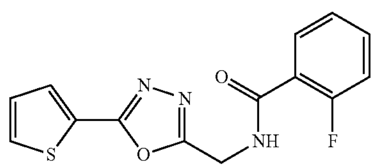 [SMILES: O=C(NCc1nnc(-c2cccs2)o1)c1ccccc1F] | 2-fluoro-N-((5-(thiophen-2-yl)-1,3,4-oxadiazol-2-yl)methyl)benzamide |
| 45 | 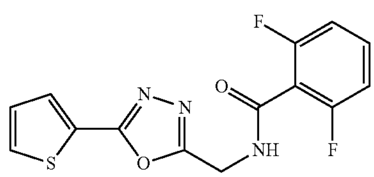 [SMILES: O=C(NCc1nnc(-c2cccs2)o1)c1c(F)cccc1F] | 2,6-difluoro-N-((5-(thiophen-2-yl)-1,3,4-oxadiazol-2-yl)methyl)benzamide |
| 46 | 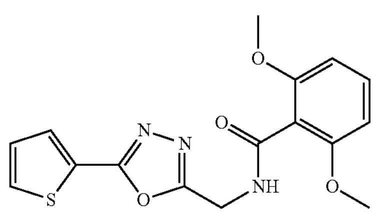 [SMILES: COc1cccc(OC)c1C(=O)NCc1nnc(-c2cccs2)o1] | 2,6-dimethoxy-N-((5-(thiophen-2-yl)-1,3,4-oxadiazol-2-yl)methyl)benzamide |
| 47 | 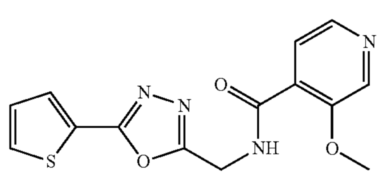 [SMILES: COc1cnccc1C(=O)NCc1nnc(-c2cccs2)o1] | 3-methoxy-N-((5-(thiophen-2-yl)-1,3,4-oxadiazol-2-yl)methyl)isonicotinamide |
| 48 | 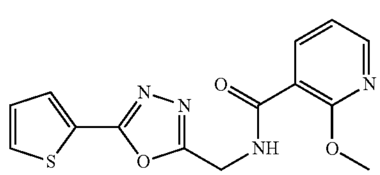 [SMILES: COc1ncccc1C(=O)NCc1nnc(-c2cccs2)o1] | 2-methoxy-N-((5-(thiophen-2-yl)-1,3,4-oxadiazol-2-yl)methyl)nicotinamide |

-continued

| No | Structure | Name |
|---|---|---|
| 49 | 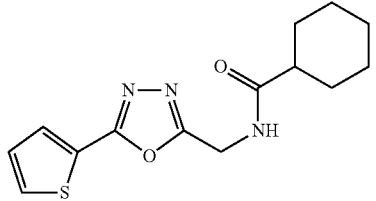 [SMILES: O=C(NCc1nnc(-c2cccs2)o1)C1CCCCC1] | N-((5-(thiophen-2-yl)-1,3,4-oxadiazol-2-yl)methyl)cyclohexanecarboxamide |
| 50 | 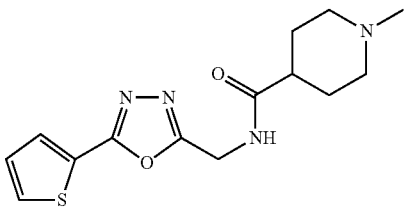 [SMILES: CN1CCC(C(=O)NCc2nnc(-c3cccs3)o2)CC1] | 1-methyl-N-((5-(thiophen-2-yl)-1,3,4-oxadiazol-2-yl)methyl)piperidine-4-carboxamide |
| 51 | 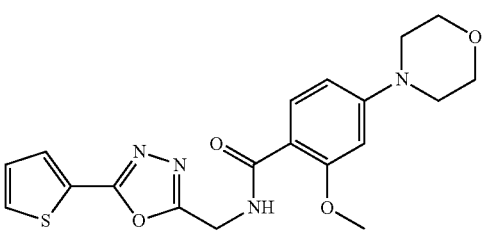 [SMILES: COc1cc(N2CCOCC2)ccc1C(=O)NCc1nnc(-c2cccs2)o1] | 2-methoxy-4-morpholino-N-((5-(thiophen-2-yl)-1,3,4-oxadiazol-2-yl)methyl)benzamide |
| 52 | 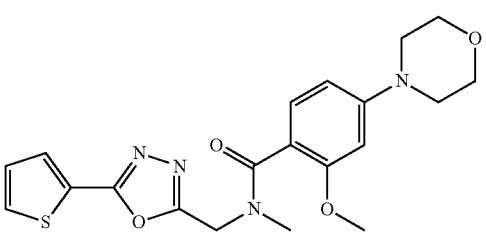 [SMILES: COc1cc(N2CCOCC2)ccc1C(=O)N(C)Cc1nnc(-c2cccs2)o1] | 2-methoxy-N-methyl-4-morpholino-N-((5-(thiophen-2-yl)-1,3,4-oxadiazol-2-yl)methyl)benzamide |
| 53 | 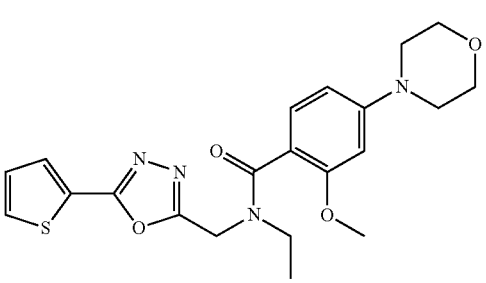 [SMILES: CCN(Cc1nnc(-c2cccs2)o1)C(=O)c1ccc(N2CCOCC2)cc1OC] | N-ethyl-2-methoxy-4-morpholino-N-((5-(thiophen-2-yl)-1,3,4-oxadiazol-2-yl)methyl)benzamide |
| 54 | 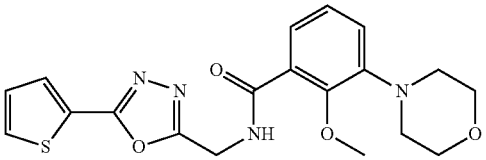 [SMILES: COc1c(C(=O)NCc2nnc(-c3cccs3)o2)cccc1N1CCOCC1] | 2-methoxy-3-morpholino-N-((5-(thiophen-2-yl)-1,3,4-oxadiazol-2-yl)methyl)benzamide |

-continued

| No | Structure | Name |
|---|---|---|
| 55 | 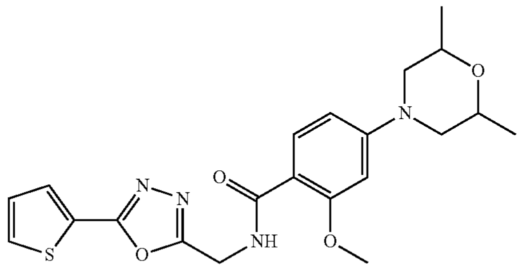 [SMILES: COc1cc(N2CC(C)OC(C)C2)ccc1C(=O)NCc1nnc(-c2cccs2)o1] | 4-(2,6-dimethylmorpholino)-2-methoxy-N-((5-(thiophen-2-yl)-1,3,4-oxadiazol-2-yl)methyl)benzamide |
| 56 | 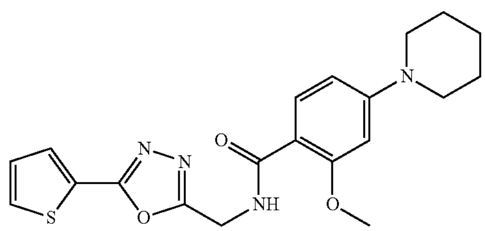 [SMILES: COc1cc(N2CCCCC2)ccc1C(=O)NCc1nnc(-c2cccs2)o1] | 2-methoxy-4-(piperidin-1-yl)-N-((5-(thiophen-2-yl)-1,3,4-oxadiazol-2-yl)methyl)benzamide |
| 57 | 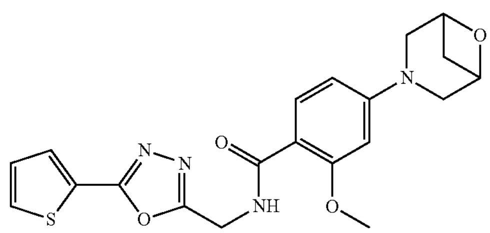 [SMILES: COc1cc(N2CC3CC(C2)O3)ccc1C(=O)NCc1nnc(-c2cccs2)o1] | 4-(6-oxa-3-azabicyclo[3.1.1]heptan-3-yl)-2-methoxy-N-((5-(thiophen-2-yl)-1,3,4-oxadiazol-2-yl)methyl)benzamide |
| 58 | 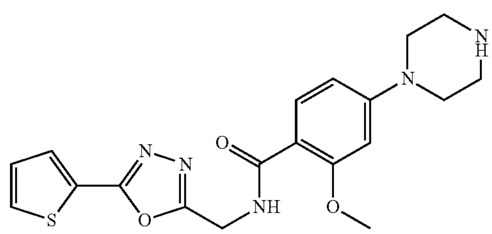 [SMILES: COc1cc(N2CCNCC2)ccc1C(=O)NCc1nnc(-c2cccs2)o1] | 2-methoxy-4-(piperazin-1-yl)-N-((5-(thiophen-2-yl)-1,3,4-oxadiazol-2-yl)methyl)benzamide |
| 59 | 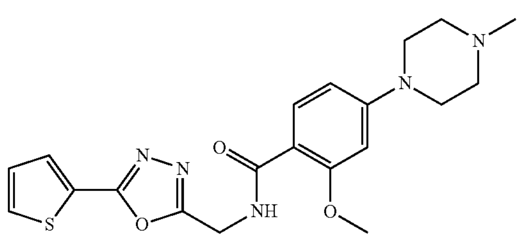 [SMILES: COc1cc(N2CCN(C)CC2)ccc1C(=O)NCc1nnc(-c2cccs2)o1] | 2-methoxy-4-(4-methylpiperazin-1-yl)-N-((5-(thiophen-2-yl)-1,3,4-oxadiazol-2-yl)methyl)benzamide |
| 60 | 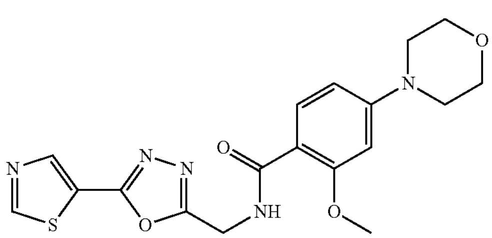 [SMILES: COc1cc(N2CCOCC2)ccc1C(=O)NCc1nnc(-c2cncs2)o1] | 2-methoxy-4-morpholino-N-((5-(thiazol-5-yl)-1,3,4-oxadiazol-2-yl)methyl)benzamide |

-continued

| No | Structure | Name |
|---|---|---|
| 61 | 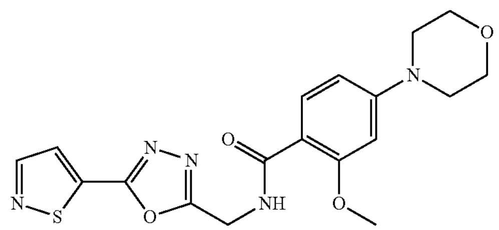 [SMILES: COc1cc(N2CCOCC2)ccc1C(=O)NCc1nnc(-c2ccns2)o1] | N-((5-(isothiazol-5-yl)-1,3,4-oxadiazol-2-yl)methyl)-2-methoxy-4-morpholinobenzamide |
| 62 | 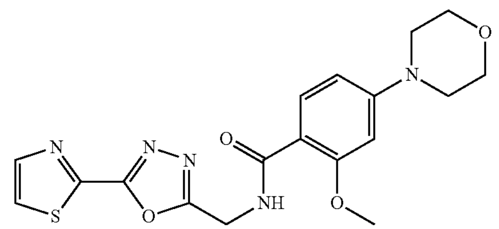 [SMILES: COc1cc(N2CCOCC2)ccc1C(=O)NCc1nnc(-c2nccs2)o1] | 2-methoxy-4-morpholino-N-((5-(thiazol-2-yl)-1,3,4-oxadiazol-2-yl)methyl)benzamide |
| 63 | 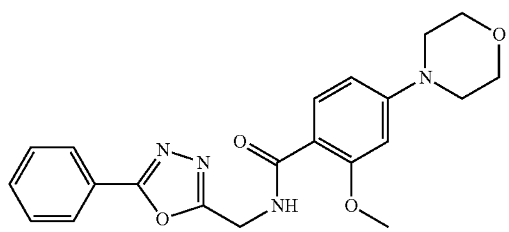 [SMILES: COc1cc(N2CCOCC2)ccc1C(=O)NCc1nnc(-c2ccccc2)o1] | 2-methoxy-4-morpholino-N-((5-phenyl-1,3,4-oxadiazol-2-yl)methyl)benzamide |
| 64 | 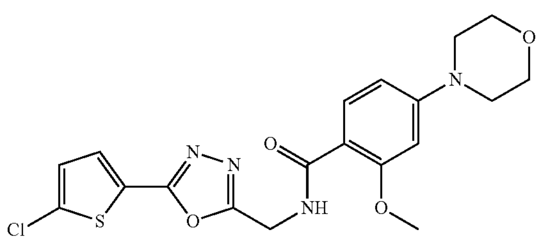 [SMILES: COc1cc(N2CCOCC2)ccc1C(=O)NCc1nnc(-c2ccc(Cl)s2)o1] | N-((5-(5-chlorothiophen-2-yl)-1,3,4-oxadiazol-2-yl)methyl)-2-methoxy-4-morpholinobenzamide |
| 65 | 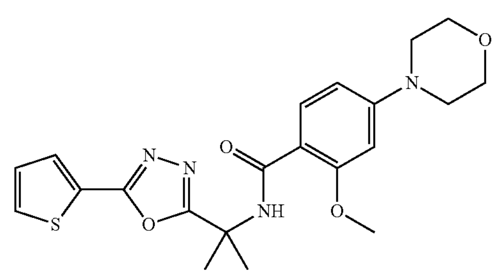 [SMILES: COc1cc(N2CCOCC2)ccc1C(=O)NC(C)(C)c1nnc(-c2cccs2)o1] | 2-methoxy-4-morpholino-N-(2-(5-(thiophen-2-yl)-1,3,4-oxadiazol-2-yl)propan-2-yl)benzamide |
| 66 | 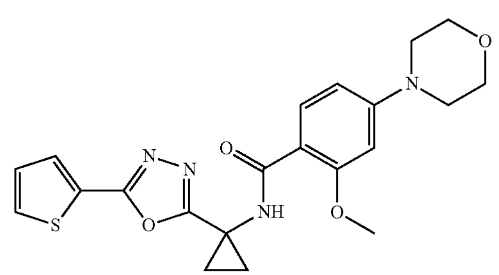 [SMILES: COc1cc(N2CCOCC2)ccc1C(=O)NC1(c2nnc(-c3cccs3)o2)CC1] | 2-methoxy-4-morpholino-N-(1-(5-(thiophen-2-yl)-1,3,4-oxadiazol-2-yl)cyclopropyl)benzamide |

-continued

| No | Structure | Name |
|---|---|---|
| 67 | 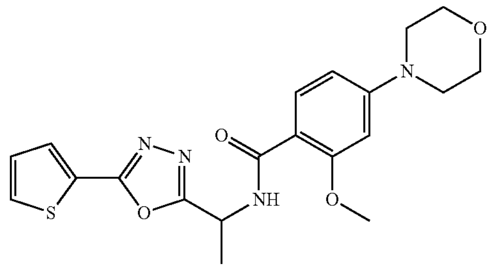 [SMILES: COc1cc(N2CCOCC2)ccc1C(=O)NC(C)c1nnc(-c2cccs2)o1] | 2-methoxy-4-morpholino-N-(1-(5-(thiophen-2-yl)-1,3,4-oxadiazol-2-yl)ethyl)benzamide |
| 68 | 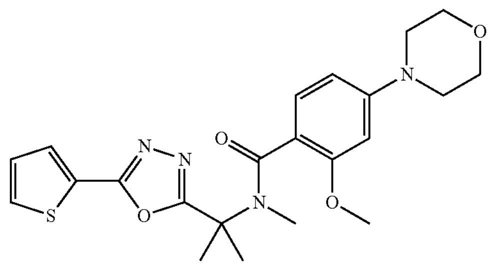 [SMILES: COc1cc(N2CCOCC2)ccc1C(=O)N(C)C(C)(C)c1nnc(-c2cccs2)o1] | 2-methoxy-N-methyl-4-morpholino-N-(2-(5-(thiophen-2-yl)-1,3,4-oxadiazol-2-yl)propan-2-yl)benzamide |
| 69 | 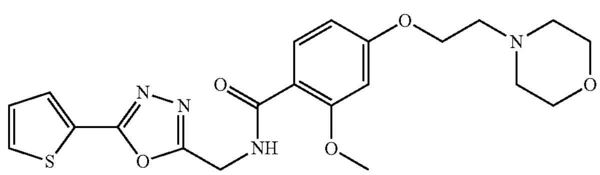 [SMILES: COc1cc(OCCN2CCOCC2)ccc1C(=O)NCc1nnc(-c2cccs2)o1] | 2-methoxy-4-(2-morpholinoethoxy)-N-((5-(thiophen-2-yl)-1,3,4-oxadiazol-2-yl)methyl)benzamide |
| 70 | 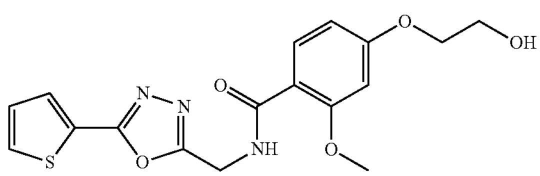 [SMILES: COc1cc(OCCO)ccc1C(=O)NCc1nnc(-c2cccs2)o1] | 4-(2-hydroxyethoxy)-2-methoxy-N-((5-(thiophen-2-yl)-1,3,4-oxadiazol-2-yl)methyl)benzamide |
| 71 | 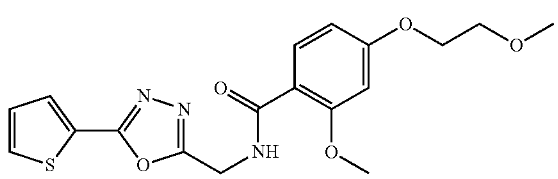 [SMILES: COCCOc1ccc(C(=O)NCc2nnc(-c3cccs3)o2)c(OC)c1] | 2-methoxy-4-(2-methoxyethoxy)-N-((5-(thiophen-2-yl)-1,3,4-oxadiazol-2-yl)methyl)benzamide |
| 72 | 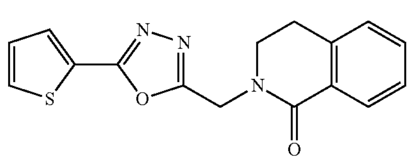 [SMILES: O=C1c2ccccc2CCN1Cc1nnc(-c2cccs2)o1] | 2-((5-(thiophen-2-yl)-1,3,4-oxadiazol-2-yl)methyl)-3,4-dihydroisoquinolin-1(2H)-one |
| 73 | 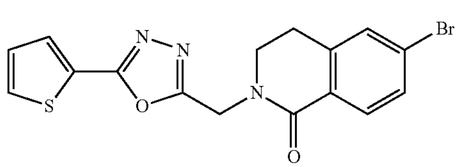 [SMILES: O=C1c2ccc(Br)cc2CCN1Cc1nnc(-c2cccs2)o1] | 6-bromo-2-((5-(thiophen-2-yl)-1,3,4-oxadiazol-2-yl)methyl)-3,4-dihydroisoquinolin-1(2H)-one |

-continued

| No | Structure | Name |
|---|---|---|
| 74 | 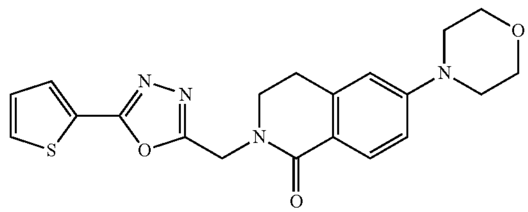 [SMILES: O=C1c2ccc(N3CCOCC3)cc2CCN1Cc1nnc(-c2cccs2)o1] | 6-morpholino-2-((5-(thiophen-2-yl)-1,3,4-oxadiazol-2-yl)methyl)-3,4-dihydroisoquinolin-1(2H)-one |
| 75 | 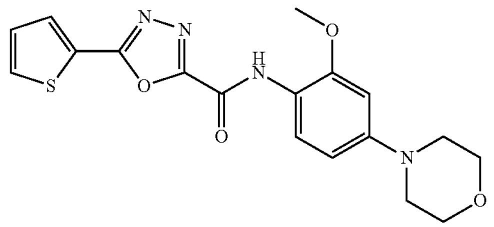 [SMILES: COc1cc(N2CCOCC2)ccc1NC(=O)c1nnc(-c2cccs2)o1] | N-(2-methoxy-4-morpholinophenyl)-5-(thiophen-2-yl)-1,3,4-oxadiazole-2-carboxamide |
| 76 | 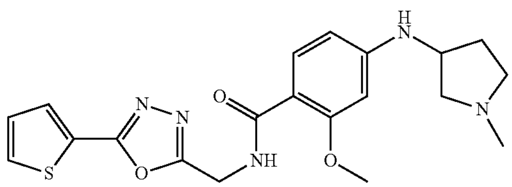 [SMILES: COc1cc(NC2CCN(C)C2)ccc1C(=O)NCc1nnc(-c2cccs2)o1] | 2-methoxy-4-((1-methylpyrrolidin-3-yl)amino)-N-((5-(thiophen-2-yl)-1,3,4-oxadiazol-2-yl)methyl)benzamide |
| 77 | 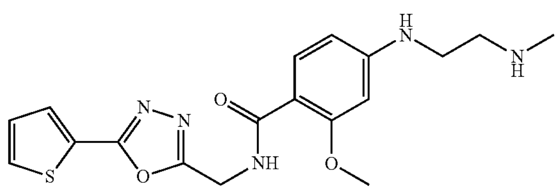 [SMILES: CNCCNc1ccc(C(=O)NCc2nnc(-c3cccs3)o2)c(OC)c1] | 2-methoxy-4-((2-(methylamino)ethyl)amino)-N-((5-(thiophen-2-yl)-1,3,4-oxadiazol-2-yl)methyl)benzamide |
| 78 | 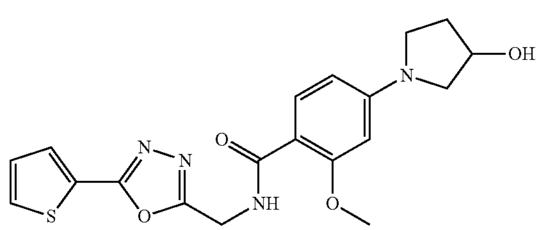 [SMILES: COc1cc(N2CCC(O)C2)ccc1C(=O)NCc1nnc(-c2cccs2)o1] | 4-(3-hydroxypyrrolidin-1-yl)-2-methoxy-N-((5-(thiophen-2-yl)-1,3,4-oxadiazol-2-yl)methyl)benzamide |
| 79 | 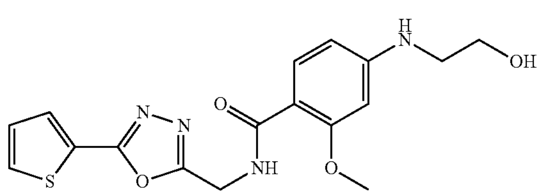 [SMILES: COc1cc(NCCO)ccc1C(=O)NCc1nnc(-c2cccs2)o1] | 4-((2-hydroxyethyl)amino)-2-methoxy-N-((5-(thiophen-2-yl)-1,3,4-oxadiazol-2-yl)methyl)benzamide |
| 80 | 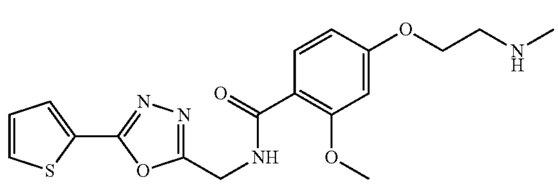 | 2-methoxy-4-(2-(methylamino)ethoxy)-N-((5-(thiophen-2-yl)-1,3,4-oxadiazol-2-yl)methyl)benzamide |
| 81 | 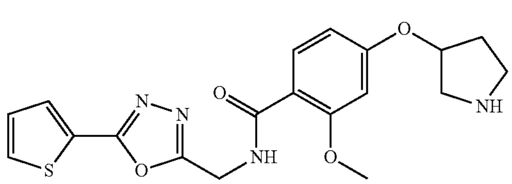 [SMILES: COc1cc(OC2CCNC2)ccc1C(=O)NCc1nnc(-c2cccs2)o1] | 2-methoxy-4-(pyrrolidin-3-yloxy)-N-((5-(thiophen-2-yl)-1,3,4-oxadiazol-2-yl)methyl)benzamide |

| No | Structure | Name |
|---|---|---|
| 87 | 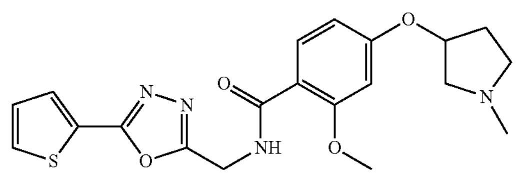 [SMILES: COc1cc(OC2CCN(C)C2)ccc1C(=O)NCc1nnc(-c2cccs2)o1] | 2-methoxy-4-((1-methylpyrrolidin-3-yl)oxy)-N-((5-(thiophen-2-yl)-1,3,4-oxadiazol-2-yl)methyl)benzamide |
| 83 | 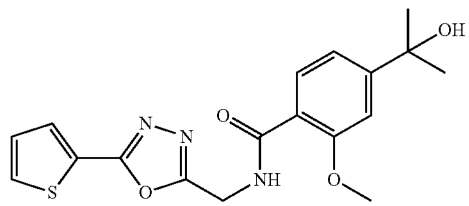 [SMILES: COc1cc(C(C)(C)O)ccc1C(=O)NCc1nnc(-c2cccs2)o1] | 4-(2-hydroxypropan-2-yl)-2-methoxy-N-((5-(thiophen-2-yl)-1,3,4-oxadiazol-2-yl)methyl)benzamide |
| 84 | 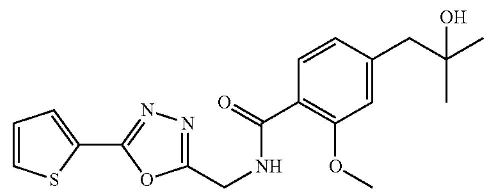 [SMILES: COc1cc(CC(C)(C)O)ccc1C(=O)NCc1nnc(-c2cccs2)o1] | 4-(2-hydroxy-2-methylpropyl)-2-methoxy-N-((5-(thiophen-2-yl)-1,3,4-oxadiazol-2-yl)methyl)benzamide |
| 85 | 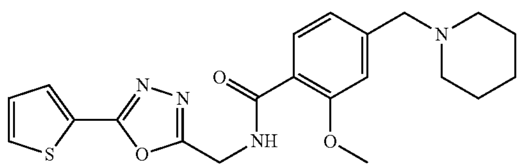 [SMILES: COc1cc(CN2CCCCC2)ccc1C(=O)NCc1nnc(-c2cccs2)o1] | 2-methoxy-4-(piperidin-1-ylmethyl)-N-((5-(thiophen-2-yl)-1,3,4-oxadiazol-2-yl)methyl)benzamide |
| 86 | 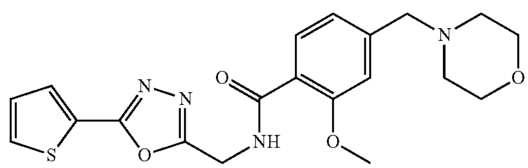 [SMILES: COc1cc(CN2CCOCC2)ccc1C(=O)NCc1nnc(-c2cccs2)o1] | 2-methoxy-4-(morpholinomethyl)-N-((5-(thiophen-2-yl)-1,3,4-oxadiazol-2-yl)methyl)benzamide |

In another aspect, the invention provides a pharmaceutical composition, comprising a compound of formula I described above, or a pharmaceutically acceptable salt thereof; and a pharmaceutically acceptable carrier or excipient.

In yet another aspect, the invention provides the use of a compound of formula I or a pharmaceutical composition described above, for the treatment of a disease mediated by MIF, Preferably, the disease mediated by MIF is
tumor selected from glioblastomas, lung cancer, breast cancer, gastric cancer, bladder cancer, melanoma;
inflammatory disease such as chronic obstructive pulmonary disease (COPD) and pneumonia;
autoimmune disease selected from rheumatoid arthritis (RA), multiple sclerosis (MS) and systemic lupus erythematosus (SLE).

In yet another aspect, the invention provides the use of a compound of formula I or a pharmaceutical composition described above, for the production of a medicine for the treatment of a disease mediated by MIF.

Preferably, the disease mediated by MIF is
tumor selected from glioblastomas, lung cancer, breast cancer, gastric cancer, bladder cancer, melanoma;
inflammatory disease such as chronic obstructive pulmonary disease (COPD) and pneumonia;
autoimmune disease selected from rheumatoid arthritis (RA), multiple sclerosis (MS) and systemic lupus erythematosus (SLE).

In yet another aspect, the invention provides a method of treating a disease mediated by MIF in a subject in need thereof, comprising administering to the subject, a therapeutically effective amount of a compound of formula I described above, or a pharmaceutically acceptable salt thereof.

Preferably, the disease mediated by MIF is
tumor selected from glioblastomas, lung cancer, breast cancer, gastric cancer, bladder cancer, melanoma;
inflammatory disease such as chronic obstructive pulmonary disease (COPD) and pneumonia;
autoimmune disease selected from rheumatoid arthritis (RA), multiple sclerosis (MS) and systemic lupus erythematosus (SLE).

Preferably, the subject is human.

In yet another aspect, the invention provides a method of inhibiting MIF expression, production and/or secretion in a subject in need thereof, the method comprising administering to the subject, a pharmaceutically effective amount of a compound of formula I described above, or a pharmaceutically acceptable salt thereof.

Preferably, the subject is human.

In yet another aspect, the invention provides a method of inhibiting MIF tautomerase catalytic activity in a subject in need thereof, the method comprising administering to the subject, a pharmaceutically effective amount of a compound of formula I described above, or a pharmaceutically acceptable salt thereof.

Preferably, the subject is human.

In yet another aspect, the invention provides a method of inhibiting MIF expression, production and/or secretion in a cell, comprising contacting the cell with a pharmaceutically effective amount of a compound of formula I described above, or a pharmaceutically acceptable salt thereof.

In yet another aspect, the invention provides a method of inhibiting MIF tautomerase catalytic activity in a cell, comprising contacting the cell with a pharmaceutically effective amount of a compound of formula I described above, or a pharmaceutically acceptable salt thereof.

DETAILED DESCRIPTION OF THE INVENTION

Definitions

In the invention, the following definitions are applicable:

The term "MIF inhibitor" includes any and all possible isomers, stereoisomers, enantiomers, diastereomers, tautomers, pharmaceutically acceptable salts, hydrates, solvates, and prodrugs of the MIF inhibitors described in this invention.

The articles "a" and "an" are used in this invention to refer to one or more than one (i.e., to at least one) of the grammatical object of the article. By way of example, "an element" means one element or more than one element.

The term "and/or" is used in this invention to mean either "and" or "or" unless indicated otherwise.

The term "carbocycle" as used in this invention refers to a 3-10 membered aromatic or nonaromatic cyclic carbon chain. Examples of nonaromatic carbocycles include cyclopropyl, cyclobutyl, cyclopentyl and the like. Examples of aromatic carbocycles include benzene, naphthalene, anthracene, phenanthrene and the like.

The term "heterocycle" as used in this invention refers to a cyclic hydrocarbon containing 3-10 atoms wherein at least one of the atoms is an O, N, or S wherein a monocyclic heterocycle may contain up to two double bonds. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

The term "$C_{1-6}$ alkyl", alone or in combination with other groups, refers to straight-chained or branched alkyl group having 1 to 6 carbon atoms. Examples of a $C_{1-6}$ alkyl group include, but are not limited to, methyl, ethyl, propyl, butyl, pentyl, hexyl, isopropyl, isobutyl, sec-butyl, tert-butyl, isopentyl, and neopentyl.

The term "$C_{3-6}$ cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl. It is understood that any of the substitutable hydrogens on a cycloalkyl can be substituted with halogen, $C_1$-$C_3$ alkyl, hydroxyl, alkoxy and cyano groups.

The term "$C_{1-6}$ alkoxy", alone or in combination with other groups, refers to the group R'—O—, wherein R' is a $C_{1-6}$ alkyl. Examples of a $C_{1-6}$ alkoxy group include, but are not limited to, methoxy, ethoxy, propoxy, isopropoxy, butoxy, isobutoxy, sec-butoxy, tert-butoxy, pentyloxy, isopentyloxy, neopentyloxy, tert-pentyloxy, and hexyloxy.

The term "halogen" or "halo" refers to fluoro, chloro, bromo or iodo. Preferred "halogen" groups are fluoro, chloro or bromo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described in this invention as being attached to a second group and the site of attachment is not explicit, the given group may be attached at any available site of the given group to any available site of the second group. For example, a "$C_{1-6}$ alkyl-substituted phenyl", where the attachment sites are not explicit, may have any available site of the $C_{1-6}$ alkyl attached to any available site of the phenyl group. In this regard, an "available site" is a site of the group at which a hydrogen of the group may be replaced with a substituent.

"Pharmaceutically acceptable salts" refers to those salts which retain the biological effectiveness and properties of the free bases and which are obtained by reaction with inorganic acids, for example, acid, hydrobromic acid, sulfuric acid, nitric acid, and phosphoric acid or organic acids such as sulfonic acid, carboxylic acid, organic phosphoric acid, methanesulfonic acid, ethanesulfonic acid, toluenesulfonic acid, citric acid, fumaric acid, maleic acid, succinic acid, benzoic acid, salicylic acid, lactic acid, tartaric acid (e, (+) or (−)-tartaric acid or mixtures thereof), amino acids (e.g., (+) or (−)-amino acids or mixtures thereof), and the like. These salts can be prepared by methods known to those skilled in the art. "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

The term "carrier", as used in this invention, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a therapeutically effective amount. An effective amount can be determined by methods known to those of skill in the art.

A compound of a given formula (e.g. compound of Formula I) is intended to encompass the compounds of the invention, and the pharmaceutically acceptable salts, pharmaceutically acceptable esters, isomers, tautomers, solvates, isotopes, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of a given formula depends upon the number of asymmetric centers present (there are 2" stereoisomers possible where n is the number of asymmetric centers). The individual stereoisomers may be obtained by resolving a racemic or non-racemic mixture of an intermediate at some appropriate stage of the synthesis or by resolution of the compound by conventional means.

The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(f)" is used to designate a racemic mixture where appropriate.

"Diastereoisomers" are stereoisomers that have at least two asymmetric atoms, but which are not mirror-images of each other.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of the present invention and a solvent.

The term "hydrate" refers to the complex formed by the combining of a compound of the present invention and water.

The term "prodrug" refers to compounds of the present invention that include chemical groups which, in vivo, can be converted and/or can be split off from the remainder of the molecule to provide for the active drug, a pharmaceutically acceptable salt thereof or a biologically active metabolite thereof.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably in this invention.

The term "inhibition", "inhibit" or "inhibiting" indicates a significant decrease in the baseline activity of a biological activity or process.

The term "disease" is used in this invention to mean, and is used interchangeably with, the terms disorder, condition, or illness, unless otherwise indicated.

The term "tumor", as used in this invention, refers to an abnormal growth of tissue. A tumor may be benign or malignant. Generally, a malignant tumor is referred to as a cancer. Cancers differ from benign tumors in the ability of malignant cells to invade other tissues, either by direct growth into adjacent tissue through invasion or by implantation into distant sites by metastasis (i.e., transport through the blood or lymphatic system).

The term "autoimmune disease", as used in this invention, refers to a disease which arises from an inappropriate immune response of the body against substances and tissues normally present in the body (autoimmunity) of a patient. The symptoms of autoimmune diseases can range from fatigue and mild rashes to rare, serious warning signs, like seizures. Preferably, the autoimmune disease is selected from the group consisting of rheumatoid arthritis (RA), multiple sclerosis (MS), sarcoidosis, psoriasis, Crohn's disease, systemic lupus erythematosus (SLE), and diabetes mellitus type 1, and more preferably the autoimmune disease is selected from the group consisting of rheumatoid arthritis (RA), multiple sclerosis (MS), and systemic lupus erythematosus (SLE).

The term "inflammatory disease", as used in this invention, refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory disease preferably is chronic obstructive pulmonary disease (COPD), pneumonia.

The term "treating", with regard to a subject, refers to improving at least one symptom of the subject's disease. Treating can be curing, improving, or at least partially ameliorating the disease.

The term "administer", "administering", or "administration", as used in this invention, refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

Pharmaceutical Compositions and Administration

The invention also includes pharmaceutical compositions useful for treating a disease mediated by MIF, or for inhibiting MIF expression, production and/or secretion, or for inhibiting MIF tautomerase catalytic activity, or more than one of these activities. The compositions can be suitable for internal use and comprise an effective amount of compounds of the invention as MIF inhibitors and a pharmaceutically acceptable carrier. The MIF inhibitors are especially useful in that they demonstrate very low systemic toxicity or no systemic toxicity.

The MIF inhibitors can each be administered in amounts that are sufficient to treat or prevent but are not limited to cardiovascular and cerebrovascular diseases, autoimmune diseases and inflammatory disorders, fibrotic diseases, metabolic disorders, and tumors or prevent the development thereof in subjects.

Administration of the MIF inhibitors can be accomplished via any mode of administration for therapeutic agents. These modes include systemic or local administration such as oral, nasal, parenteral (intravenous), intramuscular, intrathecal, intra-vitreal, transdermal, subcutaneous, vaginal, buccal, rectal, topical administration modes or as a drug-eluting stent.

Depending on the intended mode of administration, the compositions can be in solid, semi-solid or liquid dosage form, such as injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, intrathecal, intra-vitreal injection, subcutaneous or intramuscular form, all using forms well known to those skilled in the pharmaceutical arts.

Illustrative pharmaceutical compositions are tablets and gelatin capsules comprising a MIF inhibitor and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxy-propyl-cyclodextrin, PEG400, PEG200.

Liquid, particularly injectable, compositions can, for example, be prepared by dissolution, dispersion, etc. For example, the MIF inhibitor is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the MIF inhibitors.

The MIF inhibitors can be also formulated as a suppository that can be prepared from fatty emulsions or suspensions; using polyalkylene glycols such as propylene glycol, as the carrier.

In further embodiments, the pharmaceutical formulations described in this invention include, but are not limited to, aqueous liquid dispersions, self-emulsifying dispersions, solid solutions, liposomal dispersions, aerosols, solid dosage forms, powders, immediate release formulations, controlled release formulations, fast melt formulations, delayed release formulations, extended release formulations, pulsatile release formulations, multiparticulate formulations, and mixed immediate and controlled release formulations The MIF inhibitors can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

MIF inhibitors can also be delivered by the use of monoclonal antibodies as individual carriers to which the MIF inhibitors are coupled. The MIF inhibitors can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the MIF inhibitors can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, MIF inhibitors are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the MIF inhibitor by weight or volume.

The dosage regimen utilizing the MIF inhibitor is selected in accordance with a variety of factors including type, species, age, weight, sex, race, diet, and medical condition of the patient; the severity of the condition to be treated; the route of administration; the renal or hepatic function of the patient; and the particular MIF inhibitor employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 0.1 mg to about 5000 mg of the active ingredient per unit dose which could be administered. In one embodiment, the compositions are in the form of a tablet that can be scored. Appropriate dosages of the MIF inhibitors can be determined as set forth in Goodman, L. S.; Gilman, A. The Pharmacological Basis of Therapeutics, 5th ed.; MacMillan: New York, 1975, pp. 201-226.

MIF inhibitors can be administered in a single daily dose, or the total daily dosage can be administered in divided doses of two, three or four times daily. Furthermore, MIF inhibitors can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the MIF inhibitor ranges from about 0.1% to about 15%, w/w or w/v.

Uses of Compounds and Compositions Thereof

The compounds as MIF inhibitors and compositions described above can be used to treat or prevent MIF-associated diseases. These diseases include, but are not limited to, autoimmune diseases, tumors, or chronic or acute inflammatory diseases. Examples of such diseases or conditions include:

- rheumatic diseases (including but not limited to rheumatoid arthritis, osteoarthritis, psoriatic arthritis) spondyloarthropathies (including but not limited to ankylosing spondylitis, reactive arthritis, Reiter's syndrome), crystal arthropathies (including but not limited to gout, pseudogout, calcium pyrophosphate deposition disease), Lyme disease, polymyalgia rheumatica;
- connective tissue diseases (Including but not limited to systemic lupus erythematosus, systemic sclerosis, polymyositis, dermatomyositis, Sjögren's syndrome);
- vasculitides (including but not limited to polyarteritis nodosa, Wegener's granulomatosis, Churg-Strauss syndrome);
- inflammatory diseases including chronic obstructive pulmonary disease (COPD), pneumonia, consequences of trauma or ischaemia;
- sarcoidosis;
- vascular diseases including atherosclerotic vascular disease and infarction, atherosclerosis, and vascular occlusive disease (including but not limited to atherosclerosis, ischaemic heart disease, myocardial infarction, stoke, peripheral vascular disease), and vascular stent restenosis;
- autoimmune diseases (including but not limited to diabetes mellitus, thyroiditis, myasthenia gravis, sclerosing cholangitis, primary biliary cirrhosis, rheumatoid arthritis (RA), multiple sclerosis (MS), systemic lupus erythematosus (SLE));
- pulmonary diseases (including but not limited to diffuse interstitial lung diseases, pneumoconioses, fibrosing alveolitis, asthma, bronchitis, bronchiectasis, chronic obstructive pulmonary disease, adult respiratory distress syndrome);
- tumors whether primary or metastatic (including but not limited to glioblastomas, prostate cancer, colon cancer, lymphoma, lung cancer, gastric cancer, bladder cancer, melanoma, multiple myeloma, breast cancer, stomach cancer, leukaemia, cervical cancer and metastatic cancer);
- renal diseases including glomerulonephritis, interstitial nephritis;
- disorders of the hypothalamic-pituitary-adrenal axis;
- nervous system disorders including multiple sclerosis, Alzheimer's disease;
- diseases characterised by modified angiogenesis (eg diabetic retinopathy, rheumatoid arthritis, cancer), endometrial function (menstruation, implantation, endometriosis);
- complications of infective disorders including endotoxic (septic) shock, exotoxic (septic) shock, infective (true septic) shock, malarial complications, other complications of infection, pelvic inflammatory disease;
- transplant rejection, graft-versus-host disease;
- allergic diseases including allergies, atopic diseases, allergic rhinitis;
- bone diseases (eg osteoporosis, Paget's disease);
- skin diseases including psoriasis, atopic dermatitis, UV(B)-induced dermal cell activation (eg sunburn, skin cancer); pain, testicular dysfunctions and wound healing;
- gastrointestinal diseases including inflammatory bowel disease (including but not limited to ulcerative colitis, Crohn's disease), peptic ulceration, gastritis, oesophagitis, liver disease (including but not limited to cirrhosis, hepatitis).

Combination Therapy

Compounds according to the present invention may be administered in combination with the following non-limiting examples of therapeutic agents and methods for treating and preventing these MIF-associated diseases in any combination that may include, but are not limited to any of the following: glucocorticoids, nonsteroidal antiinflammatory drugs (NSAIDs), cyclooxygenase (COX)-2 inhibitors, licofelone (ML3000), disease-modifying antirheumatic drugs (DMARDs), methotrexate, chloroquine, hydroxychloroquine, cyclophosphamide (Cytoxan), inosine monophosphate dehydrogenase (IMPDH) inhibitors, sirolimus, everolimus (rapamycin), purine nucleoside phosphorylase inhibitors, de novo purine synthesis inhibitors, dihydroorotate dehydrogenase inhibitors (malononitrilamides), prostaglandins PGE2 inhibitors, P2X7 receptor inhibitors, proteinase-activated receptor 2 (PAR-2) inhibitors, inhibitors of activated Complement, complement C3/C5 convertase inhibitors, active convertase inhibitors, complement C5aR antagonists, EP4 agonists, prostaglandin-12 analogs, Sulphasalazine (SASP), 5-aminosalicylic acid (5-ASA), immunomodulator drugs, calcineurin inhibitors, interleukin-10 (AGO 11), placenta-derived cells (PDA001), mucosal addressin cell adhesion molecule (MAdCAM) inhibitors (PF-00547659), GLP-2 agonists, anti-CD3, CCR9 inhibitors, lenalidomide (Revlimid), recombinant human interleukin-11, CXCR2 Antagonists, glucagon-like peptide-2 (GLP-2) analogue (Teduglutide), insulin-like growth factor-1 (IGF-1) (Increlex), synthetic guanylhydrazone semapimod (CPSI-2364), intracellular adhesion molecule-1 (ICAM-1) inhibitor (alicaforsen), stem cell therapeutics, activated protein C (aPC), vitamin D analogs, retinoids, phototherapy, methotrexate, cyclosporine, acitretin, CCR6 inhibitors, CCL20 inhibitors, deoxyspergualin, alkylate deoxyribonucleic acid (DNA) agents, tumor necrosis factor (TNF)-alpha inhibitors, inhibitors of TNF-alpha converting enzyme, Janus kinase (JAK) 1, 2 and/or 3 inhibitors, spleen tyrosine kinase (SYK) inhibitors, caspase inhibitor, chemokine receptor antagonists, protein kinase C (pkc) inhibitors, p38 mitogen-activated protein kinase (MAPK) inhibitors, caspase inhibitors, NF-κB modulators, B cell inhibitors, Hydroxychloroquine, B-lymphocyte stimulator (BLyS) inhibitors, membrane-bound and soluble B-cell activating factor inhibitors, inhibitors that antagonize the binding of BLyS and APRIL (a proliferation-inducing ligand) cytokines to B cells in order to prevent B-cell maturation and autoantibody production, anti-CD 19, CD20 inhibitors, CD22 inhibitors, T cell inhibitors, interferon inhibitors, toll-like receptor inhibitors, prasterone, estrogen receptor antagonist (fulvestrant), cytotoxic T-lymphocyte-associated antigen 4 (CTLA-4)-Ig, v-set domain containing T cell activation inhibitor 1 (VTCN1; B7-H4) agonists (AMP-110), interleukin-1 receptor antagonists (AMG 108, Anakinra [Kineret]), interleukin-1 beta antagonists, soluble IL-1 receptors, interleukin-2R antagonists, interleukin-6 receptor antagonists, calcipotriene/betamethasone (Taclonex), fumarate (Panaclar/BG-12), interleukin-15 inhibitors, interleukin-17 inhibitors (AIN457), DHODH inhibitors (Vidofludimus), interleukin-18 inhibitors, T helper (Th) 17 cell inhibitors, interleukin 12/interleukin 23 inhibitors, interleukin-22 inhibitors, interleukin-23 inhibitors, interleukin-12 inhibitors, alpha interferons, beta interferons [Interferon beta-1a (Avonex, Rebif), Interferon beta-1b (Betaseron/Betaferon), Glatiramer acetate (Copaxone), selective adhesion molecule inhibitors, integrin antagonists (Natalizumab [Tysabri], vedolizumab), sphingosine 1-phosphate receptor (S1P-R) agonists, fumarate derivative immunomodulators, laquinimod, anti-LFA-1, MBP-8298, cladribin, Novantrone, isoxanol dihydroorotate dehydrogenase (DHODH) and tyrosine kinase inhibitor, Revimmune (cyclophosphamide), Fampridine SR (4-aminopyridine), Panaclar (dimethylfumarate), MBP8298 (dirucotide, synthetic peptide version of a portion of human myelin basic protein), Campath (alemtuzumab), anti-CD52, Cladribine, purine analogs, Fingolimod (sphingosine 1-phosphate receptor agonists), Laquinimod, Teriflunomide, de novo pyrimidine synthesis inhibitors, active metabolites of leflunomide, photodynamic therapy [PDT] with verteporfin, Anti-angiogenic factors, CCR3 inhibitors, anti-CD48, beta 2-agonists, leukotriene modifiers, phosphodiesterase (PDE) inhibitors, selective phosphodiesterase-4 (PDE-4) inhibitors, inhibitors targeting IgE (Omalizumab), Th2 cytokine inhibitors, Macrolides, Ketolide, adenosine A2B antagonists, kappa B kinase 2 inhibitors, prostanoid and F2-isoprostane antagonists, Nitric oxide donors, inducible nitric oxide synthase inhibitors, toll-like receptor modulators, Lorcaserin, phentermine, topiramate, bupropion, naltrexone, Anti-CD3, Antithymocyte globulin, serine protease inhibitors, tyrosine kinase inhibitors, platelet-derived growth factor receptor (PDGFR) inhibitors, insulin, Antigen-Specific Tolerance inducting agents to Type I Diabetes, cannabinoid receptor 1 (CB1) antagonists, long-acting glucagon-like peptide 1 (GLP1) analogues, dipeptidyl peptidase 4 (DPP4) inhibitors, vasoactive intestinal peptide-pituitary adenylate cyclase-activating polypeptide receptor 2 (VPAC2) agonists, Glucokinase activators, Glucagon receptor antagonists, Cytosolic phosphoenolpyruvate carboxykinase (PEPCK) inhibitors, sodium-glucose co-transporter 2 (SGLT2) inhibitors, salsalate, IκB kinase-β (IKKβ)-inhibitors, nuclear factor kappa B inhibitors, interleukin-1 (IL-1) receptor antagonists, IL-1 beta-specific antibody, sirtuin 1 (SIRT1) activators, selective peroxisome proliferator-activated receptor (PPAR) modulators (SPPARMs), 11β-hydroxysteroid dehydrogenase type 1 (11βHSD1) inhibitors, PPARγ ligands, thiazolidinediones, glitazones, Warfarin, coumadin, pradaxa, anti-thrombotics, Statins, hydroxy-methylglutaryl-coenzyme A reductase (HMG-CoA reductase) inhibitors, ezetimibe, fenofibrates, niacin, amlodipine, Vascular cell-adhesion molecule (VCAM) antagonists, Thromboxane A2 antagonists, prostaglandin D2 receptor 1 antagonists, G-protein-coupled receptor (GPCR) modulators, cannabinoid receptor 1 (also known as CNR1) CB1 receptor antagonists (Rimonabant), cholesteryl ester transfer protein (CETP) inhibitors (JTT-705), chemokine (C—C motif) receptor 2 (CCR2) antagonists, Phospholipase A2 inhibitors, peroxisome proliferator-activated receptor (PPAR) agonists, RNA polymerase inhibitors, Leukotriene synthesis inhibitors, α7 nicotinic receptors (α7 nAChRs) agonists, donepezil, galantamine, rivastigmine, memantine, α-secretase cleavage stimulants, γ-secretase activity inhibitors, antioxidant therapy, estrogens, NO synthetase inhibitors, anti-β-amyloid (Aβ) (bapineuzumab), Abiraterone, ActRIIA signaling inhibitors (ACE-011), adriamycin, aldesleukin [Proleukin], alemtuzumab, alitretinoin, alkylating agents and microtubule inhibitors, allopurinol, allosteric Akt inhibitors (Akti) [MK-2206], altretamine, amifostine, anastrozole (Arimidex), triple angiokinase inhibitor that inhibits VEGF receptors (VEGFR) 1, 2, and 3, fibroblast growth factor receptors, and platelet-derived growth factor receptors (BIBF 1120), angiopoietin 1/2-neutralizing peptibody (AMG 386), anthracycline (amrubicin), antigen-specific cancer immunotherapeutics (ASCI), antimetabolites (Raltitrexed), Apaziquone (EOquin), aprepitant, aromatase inhibitors, arsenic trioxide, Asparaginase, anaplastic lymphoma kinase (ALK) inhibitor (crizotinib, AP26113), azacitidine (Vidaza), BCG Live, Bcl-2 family inhibitors, Bcr-Abl inhibitors, bendamustine, bexarotene capsules, bexarotene gel, bleomycin, BRAF signaling inhibitors, busulfan intravenous, busulfan oral, Cabazitaxel (Jevtana), calusterone, capecitabine (Xeloda), carboplatin, carmustine, carmustine with Polifeprosan 20 Implant, caspase inhibitors, anti-CD23, anti-CD30, anti-CD32, anti-CD33, anti-CD40, chlorambucil, cisplatin, cladribine, c-Met receptor tyrosine kinase inhibitors (ARQ197), clofarabine (Clolar), CS1 inhibitors, cytotoxic T-lymphocyte-associated antigen 4 (CTLA-4) inhibitors, cyclophosphamide, cytarabine, cytarabine liposomal, dacarbazine, dactinomycin, actinomycin D, Darbepoetin alfa (Aranesp), daunorubicin liposomal, daunorubicin, daunomycin, histone deacetylase (HDAC) inhibitors, decitabine (Dacogen), Delta-like 4 ligand (DLL4) inhibitors (OMP-21M18), Denileukin, diftitox, dexrazoxane, docetaxel (Taxotere), doxorubicin, doxorubicin liposomal, Dromostanolone propionate, DR5 agonists (LBY135), Elliott's B Solution, epidermal growth factor receptor (EGFR) inhibitors, epidermal growth factor receptor tyrosine kinase (EGFR-TK) inhibitors, EGFR inhibitor-protein-tyrosine kinase inhibitors, dual EGFR/HER2 receptor tyrosine kinase inhibitors, elsamitrucin, endothelin-B receptor agonists, epirubicin, Epoetin alfa and beta, etoposide phosphate, etoposide (VP-16), exemestane, famesyltransferase inhibitor (FTI), fentanyl, floxuridine (intraarterial), fludarabine, fluorouracil (5-FU), fulvestrant (Faslodex), G2 checkpoint abrogator (CBP501), GA101, gemcitabine (Gemzar), gemtuzumab ozogamicin, Gonadotropin-Releasing Hormone (GnRH) agonists, goserelin acetate, Granulocyte-Colony Stimulating Factor, granulocyte macrophage-colony stimulating factor (GM-CSF) (Sargramostim), heat shock protein 90 (Hsp90) inhibitors, hedgehog pathway inhibitor (RG3616), Pan-HER inhibitors (PF-00299804), Herceptin, HPV vaccines, human death receptor 5 agonists, hydroxyurea, Ibritumomab (Zevalin), idarubicin, ifosfamide, imatinib mesylate (Gleevec/Glivec), immunomodulatory drugs (IMiDs), type 1 insulin-like growth factor receptor (IGF-1R) inhibitors, dual kinase inhibitor of both insulin-like growth factor-1 receptor (IGF-1R) and insulin receptor (IR) (OSI-906), interleukin-2, ipilimumab, irinotecan, Istodax (romidepsin), lapatinib (Tykerb), leteprinim, leucovorin, levamisole, levoleucovorin, LOddC, lomustine (CCNU), leuprorelin, leutinizing hormone releasing hormone (LHRH) agonists and antagonists, lucanthone, MAGE-A3-inhibitors, MAPK/ERK kinase 1/2 inhibitors (AZD6244), meclorethamine (nitrogen mustard), megestrol acetate, melphalan (L-PAM), mercaptopurine (6-MP), mesna, MET inhibitors (XL184), methotrexate, methoxsalen, midostaurin (PKC412), mifamurtide (Mepact), mitomycin C, mitotane, mitoxantrone, mammalian target of rapamycin (mTOR) inhibitors, MEK inhibitors, microtubule inhibitors, Microtubule stabilizers (patupilone [EP0906]), multikinase inhibitors, multitargeted receptor tyrosine kinase inhibitors (TKI) (TKI258), nandrolone phenpropionate, Necitumumab, Neulasta, NK-1 receptor inhibitors, Nofetumomab, Noscapine (CB3304), ondansetron, Oprelvekin, oxaliplatin (Eloxatin), PI3K inhibitors, Dual PI3K/mTOR Inhibitors (BEZ235), paclitaxel (Abraxane), pamidronate, platelet-derived growth factor receptor alpha (PDGFR-α) inhibitors (IMC-3G3), pegademase, Pegaspargase, Pegfilgrastim, pentostatin, pertuzumab, pipobroman, plicamycin, polo-like kinase 1 (Plk-1) inhibitors, mithramycin, poly (ADP-ribose) polymerase-1 (PARPi) inhibitors, porfimer sodium, integrins αvβ3 and αvβ5 inhibitors (cilengitide [EMD121974]), Pemetrexed (Alimta), pralatrexate injection (Folotyn), plerixafor, dual pro-apoptotic receptor (PARA) DR4 and DR5 agonists, procarbazine, protein-tyrosine kinase inhibitors, proteasome inhibitors, quinacrine, raf and VEGFR inhibitors, Receptor activator of nuclear factor-κB ligand (RANKL) inhibitors, Rasburicase, multitargeted receptor tyrosine kinase (RTK) inhibitor, romidepsin (Istodax), Seocalcitol (CB1089), polyethyleneglycol-SN38 conjugates (EZN-2208), Satraplatin, dual Src and Bcr-Abl kinase inhibitors, streptozocin, talbuvidine (LDT), talc, tamoxifen (Nolvadex), T-DM1, temozolomide, teniposide (VM-26), testolactone, therapeutic vaccines (BiovaxID, IRX-2, Rindopepimut (CDX-110), sipuleucel-T [Provenge], TVA immunotherapy, Stimuvax [BLP25 liposome vaccine]), somatostatin analogues, taxane (Ortataxel), tasisulam, thalidomide [Thalomid], thioguanine (6-TG), thiotepa, topoisomerase I and II inhibitors, topoisomerase I inhibitors (gimatecan [LBQ707], irinotecan), topotecan (Hycamtin), toremifene, Trabectedin (Yondelis), Trastuzumab, tretinoin (ATRA), Tositumomab (Bexxar), TRPM8 agonists (D-3263), uracil mustard, recombinant urate-oxidase (Elitek), valrubicin, valtorcitabine (monoval LDC), antagonists of vascular endothelial growth factor receptors 1, 2 and 3 ("VEGFR1-3")/platelet-derived growth factor receptor ("PDGFR")/stem cell factor receptor ("c-kit") (motesanib), vascular endothelial growth factor receptor (VEGFR)/epidermal growth factor receptor (EGFR)/rearranged during transfection (RET) tyrosine kinase inhibitors (vandetanib), vascular endothelial growth factor (VEGF) inhibitors (Cediranib, Ramucirumab), VEGFR/EGFR/HER-2 inhibitors (AEE788), vinblastine, vinorelbine, Wnt signaling inhibitors (OMP-18R5), zoledronate, zoledronic acid and combinations thereof, among others.

General Synthesis

Typical embodiments of compounds in accordance with the present invention may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods. Compounds of the present invention can be prepared beginning with commercially starting materials and utilizing general synthetic techniques and procedures known to those skilled in the art. Outlined below are reaction schemes suitable for preparing such compounds. Further exemplification is found in the specific Examples detailed below.

The compounds disclosed in this invention may have chiral centers, e.g., chiral carbon atoms. Such compounds thus include racemic mixtures of all stereoisomers, including enantiomers, diastereomers, and atropisomers. In addition, the compounds disclosed in this invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

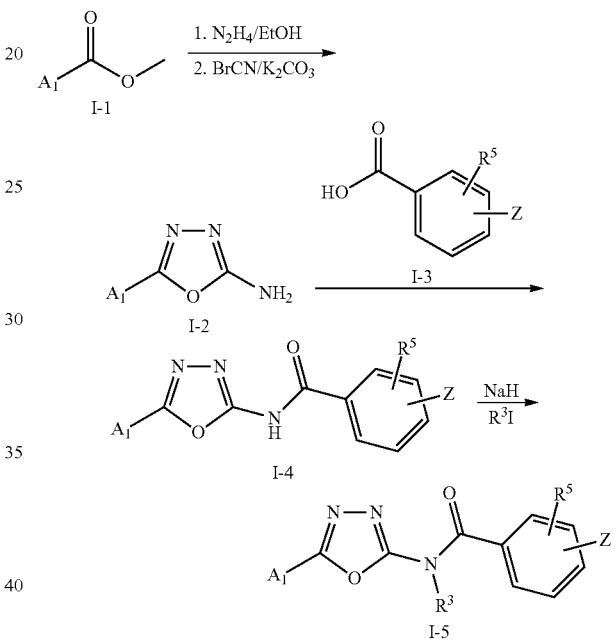

Scheme 1

In scheme 1, the amino-oxodiazole I-2 is made from a one-step procedure. In some embodiments, $A_1$ is a phenyl or heterocycle. The condensation of the amine with a carboxylic acid I-3 gives I-4. In some embodiments, the amide is converted to N-methyl amide using a suitable base and alkyl halide, under appropriate conditions, such as time and temperature. $A_1$ and $R^3$ are the same as described in this invention, and $R^5$ and/or Z may be the same as described in this invention for substituents on $A_3$ i.e. phenyl in this context).

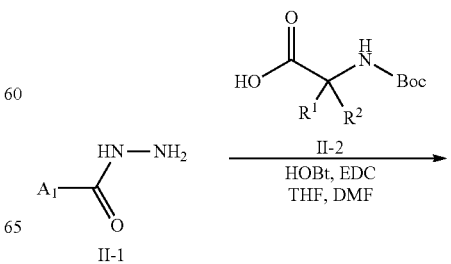

Scheme 2

-continued

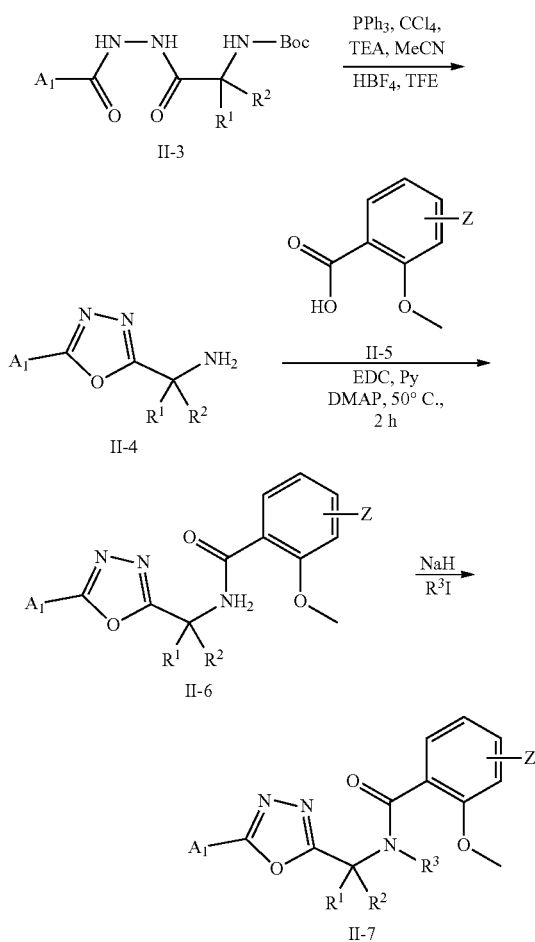

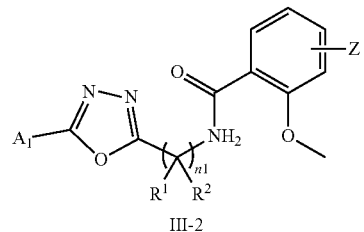

In scheme 2, methylamino-oxodiazole II-4 is made from a two-step procedure. The intramolecular cyclization of the intermediate II-3 followed by removing the tert-butoxycarbonyl protecting group gives the methylamine II-4. The condensation of the amine with the carboxylic acid IL-5 gives II-6. In some embodiments, II-6 is converted to II-7 using a suitable base (such as NaH) and alkyl halide (such as $R^3I$), under appropriate conditions, such as time and temperature. $A_1$, $R^1$, $R^2$ and $R^3$ are the same as described in this invention, and Z may be the same as described in this invention for substituents on $A_3$ i.e., phenyl in this context).

Scheme 3

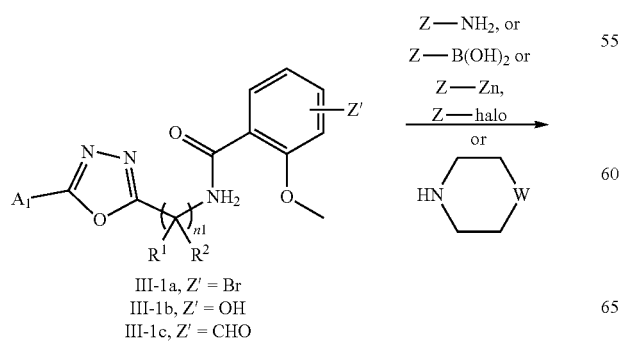

In scheme 3, Z is a substituent on $A_3$ (i.e., phenyl in this context) and can be introduced at the later stage using this method. In some embodiments, Z is connected with a nitrogen atom. In this case, a palladium catalyzed reaction between an amine Z—$NH_2$ and III-1a gives the product. In some embodiments, Z is connected with a carbon atom, a palladium catalyzed reaction between a boronic acid Z—B$(OH)_2$ and III-1a gives an alkene. The alkene is reduced using hydrogen gas to afford the product. Alternatively, the same transformation can be achieved by an organo zinc reagent as a coupled partner to afford the product. In some embodiments, Z is connected with an oxygen atom, the alkylation of III-1b with an alkyl halide (such as Z-halo) gives the product. In some embodiments, Z is connected with a linker such as a $CH_2$ unit. The linker was made by a reductive amination with an amine (such as piperidine, W=$CH_2$) and III-1c to afford the product. $A_1$, n1, $R^1$ and $R^2$ are the same as described in this invention, and Z may be the same as described in this invention for substituents on $A_3$ (i.e., phenyl in this context).

Scheme 4

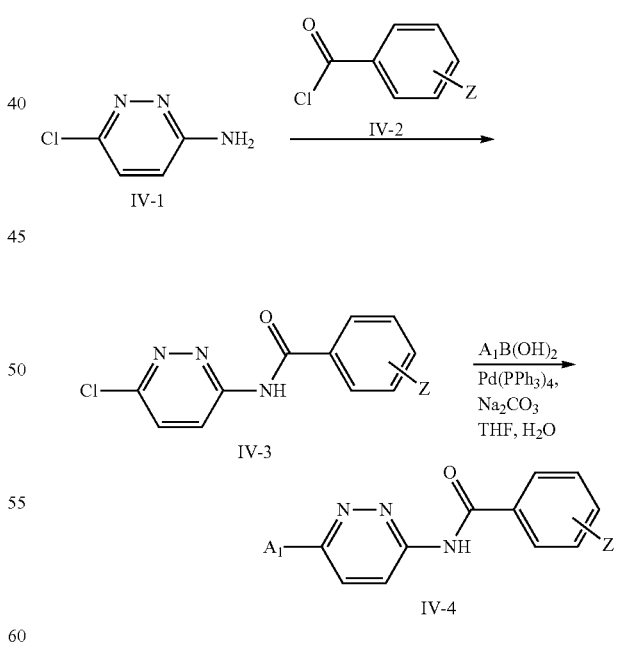

In some embodiments with pyridazine, the condensation of IV-1 and an acid chloride IV-2 followed by a palladium catalyzed reaction of the obtained IV-3 gives the product IV-4. $A_1$ is the same as described in this invention, and Z may be the same as described in this invention for substituents on $A_3$ (i.e., phenyl in this context).

Scheme 5

In some embodiments with cyclic amide, the corresponding chloromethyl oxadiazole V-3 is made by a two-step procedure starting from V-1 and V-2, followed by an intramolecular cyclization. $R^5$ is originally on V-4. V-4 is coupled with V-3 to give the product V-5. $A_1$ is the same as described in this invention, and $R^5$ may be the same as described in this invention for substituents on $A_3$ (i.e., phenyl in this context).

EXAMPLES

The present invention can be better understood according to the following examples. However, it would be easy for a person skilled in the art to understand that the contents described in the examples are merely intended to illustrate the present invention rather than limit the present invention described in detail in the claims.

Unless otherwise indicated, compounds of the present invention can be prepared beginning with commercially starting materials and utilizing general synthetic techniques and procedures known to those skilled in the art. Chromatography supplies and equipment may be purchased from such companies as for example AnaLogix, Inc, Burlington, WI; Analytical Sales and Services, Inc., Pompton Plains, NJ; Teledyne Isco, Lincoln, NE; VWR International, Bridgeport, NJ; and Rainin Instrument Company, Woburn, MA. Chemicals and reagents may be purchased from companies such as for example Aldrich, Argonaut Technologies, VWR and Lancaster, Invitrogen, Sigma, Promega, Solarbio, Cisbio, Signalchem, MCE. Consumables may be purchased from companies such as for example Corning, Labcyte, Greiner, Nunc. Instruments may be purchased from companies such as for example Labcyte, PerkinElmer, Eppendorf, ThermoFisher.

Example 1

2-chloro-N-(5-(furan-2-yl)-1,3,4-oxadiazol-2-yl)-4-methoxybenzamide

To a solution of 5-(2-furyl)-1,3,4-oxadiazol-2-amine (90 mg, 0.6 mmol) and DMAP (7 mg, 0.06 mmol) in pyridine (5.0 mL), was added 2-chloro-4-methoxybenzoyl chloride (369 mg, 1.8 mmol) at 10° C. The reaction mixture was stirred at 30° C. overnight. The mixture was poured into ice-water (6 mL) and then extracted with DCM (10 mL×2). The combined organic layers were washed with brine (6 mL), dried over anhydrous $Na_2SO_4$ and concentrated under reduced pressure. The residue was purified by column chromatography on silica gel (DCM/EtOAc=10 to 1:1) to afford the titled compound (11 mg, yield: 6%) as an off-white solid. LC-MS (ESI): m/z 320.1 $[M+H]^+$. $^1H$ NMR (400 MHz, DMSO-$d_6$): δ 12.35 (s, 1H), 8.06 (s, 1H), 7.84 (d, J=8.8 Hz, 1H), 7.65 (d, J=8.4 Hz, 1H), 7.27 (d, J=3.6 Hz, 1H), 7.17 (d, J=2.0 Hz, 1H), 7.03 (dd, J=2.4, 8.4 Hz, 1H), 3.85 (s, 3H).

Example 2

2,4-dimethoxy-N-(5-phenyl-1,3,4-oxadiazol-2-yl)benzamide

Following the same procedure for Example 1 using 5-phenyl-1,3,4-oxadiazol-2-amine (186 mg, 1.16 mmol) as the amine to afford the titled compound (45 mg, yield: 12%) as a white solid. LC-MS (ESI): m/z 326.2 $[M+H]^+$. $^1H$ NMR (400 MHz, DMSO-$d_6$): δ 11.13 (s, 1H), 7.98-7.96 (m, 2H), 7.77 (d, J=8.8 Hz, 1H), 7.63-7.61 (m, 3H), 6.73-6.69 (m, 2H), 3.93 (s, 3H), 3.87 (s, 3H).

Example 3

(S)-1-benzyl-N-(5-(furan-2-yl)-1,3,4-oxadiazol-2-yl)pyrrolidine-3-carboxamide

To a solution of 5-(2-furyl)-1,3,4-oxadiazol-2-amine (0.31 g, 2.0 mmol) in THF (30.0 mL) was added NaH (0.29 g, 7.2 mmol) at 0° C. The mixture was stirred for 15 min. A solution of (S)-1-benzylpyrrolidine-3-carbonyl chloride (0.8 g, 3.1 mmol) in THF (20 mL) was added at 0° C. The reaction mixture was stirred at 25° C. for 6 h. The mixture was poured into ice-water (20 mL) and then extracted with EtOAc (50 mL×2). The combined organic layers were washed with brine (40 mL), dried over anhydrous $Na_2SO_4$, filtered and concentrated under reduced pressure. The residue was purified by preparative HPLC to afford the titled compound in two batches (142 mg, 98.9/o purity and 178 mg, 86.6% purity, combined yield: 47%) as a white solid. LC-MS (ESI): m/z 339.2 $[M+H]^+$. $^1$H NMR (400 MHz, $DMSO_6$): δ 8.03 (s, 1H), 7.32-7.22 (m, 7H), 6.78 (dd, J=1.6, 3.2 Hz, 1H), 3.59 (s, 2H), 3.35 (m, 1H), 2.83 (t, J=8.4 Hz, 1H), 2.62-2.59 (m, 3H), 2.05-1.99 (m, 2H).

Example 4

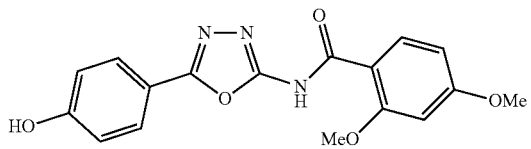

4

N-(5-(4-hydroxyphenyl)-1,3,4-oxadiazol-2-yl)-2,4-dimethoxybenzamide a) 2-(4-(benzyloxy)benzoyl)hydrazine-1-carbothioamide To a solution of 4-benzyloxybenzoyl chloride (1.0 g, 4.05 mmol) in THF (20 mL) was added portionwise thiosemicarbazide (554 mg, 6.07 mmol) at 15° C. The reaction mixture was stirred at room temperature for 3 hours. Saturated aqueous $NaHCO_3$ (10 mL) was added and the resulting precipitate was collected by filtration. The solid was washed with hot $H_2O$ (50° C., 100 mL) and dried to afford the titled compound (1.1 g, yield: 90%) as a white solid. LC-MS (ESI): m/z 302.2 $[M+H]^+$. $^1$H NMR (400 MHz, DMSO-$d_6$): δ 10.25 (br s, 1H), 9.30 (br s, 1H), 7.86 (d, J=8.8 Hz, 3H), 7.60 (br s, 1H), 7.47-7.32 (m, 5H), 7.08 (d, J=8.8 Hz, 2H), 5.19 (s, 2H).

b) 5-(4-(benzyloxy)phenyl)-1,3,4-oxadiazol-2-amine

To a solution of 2-(4-(benzyloxy)benzoyl)hydrazine-1-carbothioamide (1.1 g, 3.65 mmol) in i-PrOH (9 mL) was added a solution of KI (182 mg, 1.1 mmol) in $H_2O$ (2 mL) at room temperature. The solution was cooled to 5° C. and aqueous NaOH (5 M, 1.1 mL) was added. To the resulting mixture was added dropwise a solution of 1,3-dibromo-5,5-dimethylhydantoin (783 mg, 2.74 mmol) in acetonitrile (11 mL) at 5-10° C. The reaction mixture was stirred at 10° C. for 1 h. The reaction was quenched with aqueous $NaHSO_3$ (0.25 mL). EtOAc (30 mL) was added to the slurry and the precipitate was collected by filtration. The solid was washed with EtOAc (20 mL) and dried to afford the titled compound (0.6 g, yield: 60%) as a white solid. LC-MS (ESI): m/z 367.7 $[M+H]^+$. $^1$H NMR (400 MHz, DMSO-$d_6$): δ 7.76-7.72 (m, 2H), 7.46-7.35 (m, 5H), 7.17-7.15 (m, 4H), 5.18 (s, 2H).

c) N-(5-(4-(benzyloxy)phenyl)-1,3,4-oxadiazol-2-yl)-2,4-dimethoxybenzamide

To a solution of 5-(4-(benzyloxy)phenyl)-1,3,4-oxadiazol-2-amine (300 mg, 1.12 mmol) in pyridine (8 mL) was added dropwise a solution of 2,4-dimethoxybenzoyl chloride (269 mg, 1.34 mmol) in DCM (10 mL) at 10° C. The reaction mixture was stirred at room temperature for 3 hours. A solution of 2,4-dimethoxybenzoyl chloride (100 mg, 0.50 mmol) in DCM (3 mL) was added and the reaction mixture was stirred at room temperature overnight. The mixture was poured into ice-water (8 mL) and then extracted with DCM (10 mL×2). The combined organic layers were washed with brine (6 mL), dried over anhydrous $Na_2SO_4$, filtered and concentrated under reduced pressure. The residue was purified by column chromatography on silica gel (petroleum ether/EtOAc/DCM=3:1:1 to 0:1:1) to afford the titled compound (141 mg, yield: 29%) as a white solid. LC-MS (ESI): m/z 432.3 $[M+H]^+$. $^1$H NMR (400 MHz, DMSO-$d_6$): δ 11.03 (s, 1H), 7.91 (d, J=8.8 Hz, 2H), 7.77 (d, J=8.8 Hz, 1H), 7.50-7.40 (m, 5H), 7.24 (d, J=8.8 Hz, 2H), 6.72-6.71 (m, 2H), 5.22 (s, 2H), 3.93 (s, 3H), 3.87 (s, 3H).

d) N-(5-(4-hydroxyphenyl)-1,3,4-oxadiazol-2-yl)-2,4-dimethoxybenzamide

To a solution of N-(5-(4-(benzyloxy)phenyl)-1,3,4-oxadiazol-2-yl)-2,4-dimethoxybenzamide (70 mg, 0.16 mmol) in EtOH (150 mL) was added Pd/C (10%, 10 mg). The mixture was stirred under a balloon pressure of hydrogen gas at room temperature for 12 h. The catalyst was filtered off and the filtrate was concentrated under reduced pressure to afford the titled compound (32 mg, 58%) as a gray solid. LC-MS (ESI): m/z 340.1 $[M-H]^-$. $^1$H NMR (400 MHz, DMSO-$d_6$): δ 10.98 (s, 1H), 10.33 (s, 1H), 7.80-7.76 (m, 3H), 6.95 (d, J=8.4 Hz, 2H), 6.72-6.68 (m, 2H), 3.93 (s, 3H), 3.86 (s, 3H).

Example 5

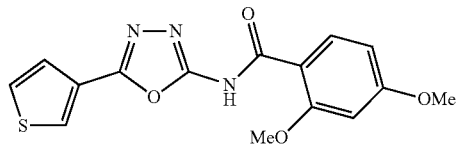

5

2,4-dimethoxy-N-(5-(thiophen-3-yl)-1,3,4-oxadiazol-2-yl)benzamide a) thiophene-3-carbohydrazide A mixture of methyl thiophene-3-carboxylate (0.5 g, 3.52 mmol, 1 eq) and hydrazine hydrate (1.85 g, 35.17 mmol, 1.80 mL, 10 eq) in ethanol (7 mL) was heated to 79° C. for 16 hours. The mixture was cooled to room temperature and concentrated in vacuo to give the title compound (0.46 g, yield: 82%) as a red solid which was used for next step. LC-MS (ESI): m/z 143.2 $[M+H]^+$.

b) 5-(thiophen-3-yl)-1,3,4-oxadiazol-2-amine

To a mixture of thiophene-3-carbohydrazide (0.46 g, 2.91 mmol) and $K_2CO_3$ (804 mg, 5.82 mmol) in $H_2O$ (20 mL) was added dropwise BrCN (0.4 mL, 2 eq) in $CH_3CN$ (1.2 mL) at 25° C. The mixture was stirred at 25° C. for 16 hours. The mixture was filtered. The solid was washed with water (5 mL) and dried in vacuo to give the titled compound (0.41 g, yield: 80%) as a white solid which was used for next step. LC-MS (ESI): m/z 168.1 $[M+H]^+$.

c) 2,4-dimethoxy-N-(5-(thiophen-3-yl)-1,3,4-oxadiazol-2-yl)benzamide

To a mixture of 5-(thiophen-3-yl)-1,3,4-oxadiazol-2-amine (106 mg, 0.6 mmol), 2,4-dimethoxybenzoic acid (0.1 g, 0.6 mmol) and TEA (0.3 mL, 2.20 mmol) in EtOAc (2 mL) was added T$_3$P (1.3 mL, 2.20 mmol, 50% in EA, v/v) and the mixture was heated to 80° C. for 16 hours. The reaction mixture was diluted with water (10 mL) and extracted with EtOAc (10 mL/3). The combined organic layers were dried over Na$_2$SO$_4$, filtered and concentrated in vacuo. The crude product was triturated with CH$_3$CN (1 mL) at 25° C. for 30 minutes, filtered and dried for drying oven (30 minutes) to give the titled compound (25 mg, yield: 13%) as a white solid. LC-MS (ESI): m/z 332.1 [M+H]$^+$; $^1$H NMR (DMSO-d$_6$, 400 MHz): δ 11.02 (s, 1H), 8.30 (dd, J=2.9, 1.2 Hz, 1H), 7.83 (dd, 1=5.0, 2.9 Hz, 1H), 7.78 (d, J=8.6 Hz, 1H), 7.61 (dd, J=5.1, 1.3 Hz, 1H), 6.66-6.77 (m, 2H), 3.94 (s, 3H), 3.87 (s, 3H), 3.83 (s, 1H), 3.81 (s, 1H).

The compounds below were synthesized following the procedures described in Example 5.

| No. | Structure | Name | MS: m/z [M + H]$^+$ | $^1$H NMR (400 MHz, DMSO-d$_6$) |
|---|---|---|---|---|
| 6 | 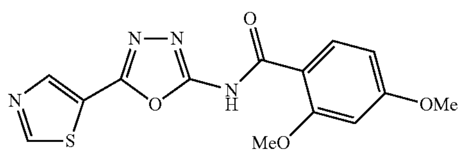 [SMILES: COc1ccc(C(=O)Nc2nnc(-c3cncs3)o2)c(OC)c1] | 2,4-dimethoxy-N-(5-(thiazol-5-yl)-1,3,4-oxadiazol-2-yl)benzamide | 333.1 | δ 10.44-11.68 (m, 1H), 9.40 (d, J = 0.6 Hz, 1H), 8.55 (s, 1H), 7.75 (d, J = 8.6 Hz, 1H), 6.62-6.74 (m, 2H), 3.93 (s, 3H), 3.87 (s, 3H). |
| 7 | 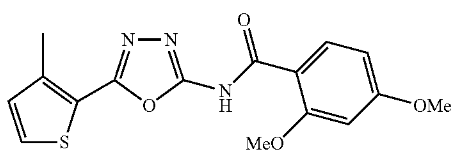 [SMILES: COc1ccc(C(=O)Nc2nnc(-c3sccc3C)o2)c(OC)c1] | 2,4-dimethoxy-N-(5-(3-methylthiophen-2-yl)-1,3,4-oxadiazol-2-yl)benzamide | 346.0 | δ 11.11 (br s, 1H), 7.80 (d, J = 5.0 Hz, 1H), 7.76 (d, J = 8.5 Hz, 1H), 7.15 (d, J = 5.0 Hz, 1H), 6.63-6.75 (m, 2H), 3.92 (s, 3H), 3.87 (s, 3H), 2.54 (br s, 3H). |
| 8 | 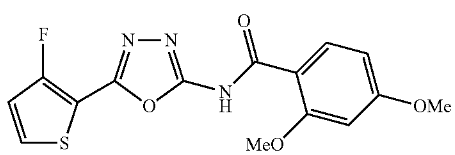 | N-(5-(3-fluorothiophen-2-yl)-1,3,4-oxadiazol-2-yl)-2,4-dimethoxybenzamide | 350.0 | δ 11.13 (br s, 1H), 7.96 (dd, J = 5.6, 4.2 Hz, 1H), 7.75 (d, J = 8.5 Hz, 1H), 7.28 (d, J = 5.5 Hz, 1H), 6.57-6.80 (m, 2H), 3.93 (s, 3H), 3.87 (s, 3H). |
| 9 | 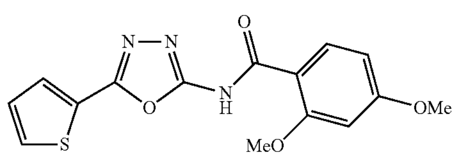 [SMILES: COc1ccc(C(=O)Nc2nnc(-c3cccs3)o2)c(OC)c1] | 2,4-dimethoxy-N-(5-(thiophen-2-yl)-1,3,4-oxadiazol-2-yl)benzamide | 332.1 | δ 11.08 (s, 1H), 7.95-7.93 (m, 1H), 7.78-7.75 (m, 2H), 7.31-7.28 (m, 1H), 6.72-6.68 (m, 2H), 3.93 (s, 3H), 3.86 (s, 3H). |
| 10 | 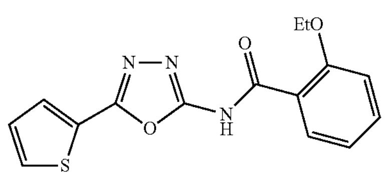 [SMILES: CCOc1ccccc1C(=O)Nc1nnc(-c2cccs2)o1] | 2-ethoxy-N-(5-(thiophen-2-yl)-1,3,4-oxadiazol-2-yl)benzamide | 316.2 | δ 11.62 (s, 1H), 7.93 (d, J = 4.8 Hz, 1H), 7.71 (d, J = 3.2 Hz, 1H), 7.65 (d, J = 8.0 Hz, 1H), 7.55 (t, J = 7.2 Hz, 1H), 7.29 (t, J = 4.8 Hz, 1H), 7.18 (d, J = 8.4 Hz, 1H), 7.08 (t, J = 7.2 Hz, 1H), 4.15 (q, J = 6.8 Hz, 2H), 1.35 (t, J = 6.8 Hz, 3H). |
| 11 | 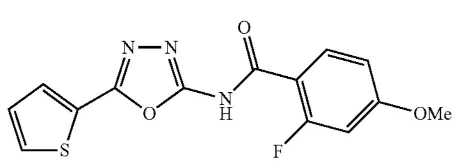 [SMILES: COc1ccc(C(=O)Nc2nnc(-c3cccs3)o2)c(F)c1] | 2-fluoro-4-methoxy-N-(5-(thiophen-2-yl)-1,3,4-oxadiazol-2-yl)benzamide | 320.0 | δ 11.98 (s, 1H), 7.93 (d, J = 4.0 Hz, 1H), 7.77-7.72 (m, 2H), 7.31-7.28 (m, 1H), 7.01-6.92 (m, 2H), 3.86 (s, 3H). |
| 12 | 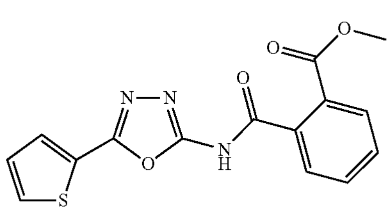 [SMILES: COC(=O)c1ccccc1C(=O)Nc1nnc(-c2cccs2)o1] | methyl 2-((5-(thiophen-2-yl)-1,3,4-oxadiazol-2-yl)carbamoyl)benzoate | 330.6 | δ 8.06-8.03 (m, 1H), 7.79-7.70 (m, 3H), 7.68-7.66 (m, 2H), 7.26 (t, J = 4.0 Hz, 1H), 3.91 (s, 3H). |

| No. | Structure | Name | MS: m/z [M + H]+ | $^1$H NMR (400 MHz, DMSO-$d_6$) |
|---|---|---|---|---|
| 13 | 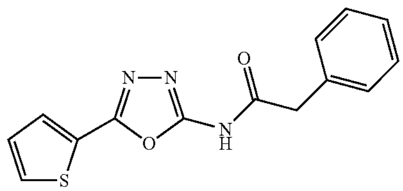 [SMILES: O=C(Cc1ccccc1)Nc1nnc(-c2cccs2)o1] | 2-phenyl-N-(5-(thiophen-2-yl)-1,3,4-oxadiazol-2-yl)acetamide | 286.2 | δ 12.04 (s, 1H), 7.91 (d, J = 5.2 Hz, 1H), 7.69 (d, J = 3.2 Hz, 1H), 7.35-7.26 (m, 7H), 3.78 (s, 2H). |

Example 6

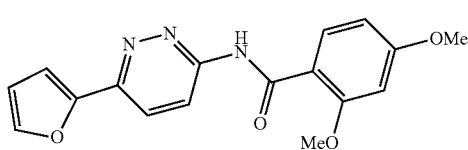

14

N-(6-(furan-2-yl)pyridazin-3-yl)-2,4-dimethoxybenzamide a) N-(6-chloropyridazin-3-yl)-2,4-dimethoxybenzamide To a solution of 6-chloropyridazin-3-amine (350 mg, 2.7 mmol) in pyridine (10 mL) was added dropwise a solution of 2,4-dimethoxybenzoyl chloride (813 mg, 4.05 mmol) in dichloromethane (5 mL) at room temperature. The reaction mixture was stirred at room temperature overnight. The mixture was poured into ice-water (10 mL) and then extracted with DCM (10 mL×2). The combined organic layers were washed with brine (10 mL), dried over anhydrous Na$_2$SO$_4$ and concentrated under reduced pressure. The residue was purified by column chromatography on silica gel (petroleum ether/EtOAc=3:1 to 1:1) to afford the titled compound (261 mg, yield: 32%).

b) N-(6-(furan-2-yl)pyridazin-3-yl)-2,4-dimethoxybenzamide

To a mixture of N-(6-chloropyridazin-3-yl)-2,4-dimethoxybenzamide (401 mg, 1.37 mmol) and furan-2-ylboronic acid (183 mg, 1.64 mmol) in DMF/H$_2$O (3.2, 10 mL) were added Na$_2$CO$_3$ (173 mg, 1.64 mmol) and Pd(PPh$_3$)$_4$ (31 mg, 0.3 mmol) under nitrogen atmosphere. The reaction mixture was stirred at 90° C. for overnight. Water (10 mL) was added and the resulting mixture was extracted with EtOAc (20 mL×2). The combined organic layers were washed with brine (20 mL), dried over anhydrous Na$_2$SO$_4$, filtered and concentrated under reduced pressure. The residue was purified by column chromatography on silica gel (petroleum ether/EtOAc/DCM=2:1:0.5) to afford the titled compound (95 mg, yield: 21%) as a white solid. LC-MS (ESI): m/z 326.1 [M+H]+. $^1$H NMR (400 MHz, DMSO-$d_6$): δ 10.85 (s, 1H), 8.55 (d, J=9.2 Hz, 1H), 8.08 (d, J=9.6 Hz, 1H), 7.98-7.95 (m, 2H), 7.27 (d, J=3.2 Hz, 1H), 6.80-6.74 (m, 3H), 4.07 (s, 3H), 3.88 (s, 3H).

Example 7

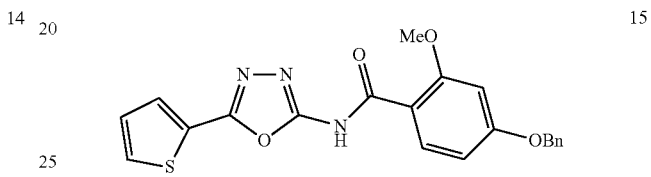

15

4-(benzyloxy)-2-methoxy-N-(5-(thiophen-2-yl)-1,3,4-oxadiazol-2-yl)benzamide a) Methyl 4-(benzyloxy)-2-hydroxybenzoate To a solution of methyl 2,4-dihydroxybenzoate (2.0 g, 11.9 mmol) in DMF (20 mL) at 5° C. was added K$_2$CO$_3$ (4.94 g, 35.7 mmol). The mixture was stirred at room temperature for 1 hour and BnBr (2.43 g, 14.2 mmol) was added dropwise at 5° C. The reaction mixture was stirred at room temperature for overnight. The mixture was diluted with ethyl acetate (20 mL) and was washed with brine (50 mL×3), the combined organic layers were dried over Na$_2$SO$_4$, filtered and evaporated. The residue was purified by column chromatography on silica gel (PE/EA=100:1 to 10:1) to afford the titled compound (2.3 g, yield: 74%) as a white solid.

b) Methyl 4-(benzyloxy)-2-methoxybenzoate

To a solution of methyl 4-(benzyloxy)-2-hydroxybenzoate (2.3 g, 8.9 mmol) in anhydrous DMF (10 mL) at 0° C. was added NaH (60% in mineral oil, 535 mg, 13.8 mmol) in portions and the mixture was stirred at 0° C. for 10 min. Iodomethane (3.16 g, 22.3 mmol) was added dropwise at 0° C. The reaction mixture was stirred at room temperature for overnight. The reaction was quenched with ice-water (50 mL) to obtain a solid. Collected the solid by filtration, washed the solid with water and dried under vacuum to afford the titled compound (2.4 g, yield: 97%) as a white solid.

c) 4-(benzyloxy)-2-methoxybenzoic Acid

To a solution of methyl 4-(benzyloxy)-2-methoxybenzoate (2.4 g 8.8 mmol) in THF (10 mL) was added aqueous NaOH (4 M, 7 mL, 22 mmol) at 0° C. The reaction mixture was refluxed for 4 hours. THF was evaporated and the pH of the mixture was adjusted to 3-4 with aqueous diluted HCl. The mixture was extracted with ethyl acetate (20 mL×3). The combined organic layers were washed with 0.6 N aqueous HCl (20 mL), dried over Na$_2$SO$_4$, filtered and evaporated to afford the titled compound (2.2 g, yield: 96%) as a white solid.

d) 2-methoxy-4-((4-methoxybenzyl)oxy)benzoyl Chloride

To a solution of 2-methoxy-4-((4-methoxybenzyl)oxy) benzoic acid (491 mg 1.9 mmol) in DCM (30 mL) was added DMF (2 mL) and oxalyl chloride (4.0 g, 38 mmol) at 0° C. under N2. The reaction mixture stirred at room temperature for 30 minutes. Solvent was evaporated to provide the titled compound and used in the next step without further purification.

e) 4-(benzyloxy)-2-methoxy-N-(5-(thiophen-2-yl)-1,3,4-oxadiazol-2-yl)benzamide

To a solution of 5-(thiophen-2-yl)-1,3,4-oxadiazol-2-amine (200 mg 1.19 mmol) in THF (15 mL) was added NaH (191 mg, 4.76 mmol) at 0° C. under $N_2$. The reaction mixture stirred at room temperature for 30 minutes, 4-(benzyloxy)-2-methoxybenzoyl chloride (509 mg, 1.89 mmol) was added into the mixture under 0° C. The reaction mixture was stirred at room temperature for overnight. The mixture was quenched with water (15 mL) and was extracted with ethyl acetate (15 mL×2). The combined organic layers were washed with brine (40 mL), dried over $Na_2SO_4$ filtered and evaporated. The residue was purified by preparative HPLC to obtain the titled compound (24 mg, yield: 15%) as a white solid. LCMS (ESI): m/z 406.0 [M+H]$^+$. $^1$HNMR (300 MHz, DMSO-$d_6$): δ 7.93 (d, J=6.8 Hz, 1H), 7.77-7.74 (m, 2H), 7.50-7.28 (m, 6H), 6.82-6.76 (m, 2H), 5.23 (s, 2H), 3.91 (s, 3H).

Example 8

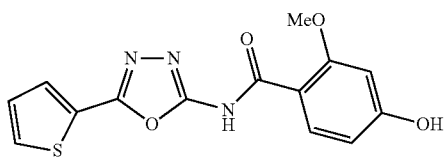

16

4-hydroxy-2-methoxy-N-(5-(thiophen-2-yl)-1,3,4-oxadiazol-2-yl)benzamide a) Methyl 2-hydroxy-4-((4-methoxybenzyl)oxy)benzoate To a solution of methyl 2,4-dihydroxybenzoate (10.0 g 59.5 mmol) in DMF (150 mL) at 5° C. was added $K_2CO_3$ (9.0 g 65.5 mmol). The mixture was stirred at room temperature for 1 hour and PMBCl (9.32 g, 59.5 mmol) was added dropwise at 5° C. The reaction mixture was stirred at room temperature for overnight. The mixture was diluted with ethyl acetate (200 mL) and washed with brine (25 mL×3). The organic layer was dried over $Na_2SO_4$, filtered and evaporated. The residue was purified by column chromatography on silica gel (PE/EA=100:1 to 10:1) to afford the titled compound (3.12 g, yield: 16%) as a gray solid. LCMS (ESI-MS): m/z 289.1 [M+H]$^+$.

b) Methyl 2-methoxy-4-((4-methoxybenzyl)oxy)benzoate

To a solution of methyl 2-hydroxy-4-((4-methoxybenzyl)oxy)benzoate (3.0 g, 10.40 mmol) in anhydrous DMF (40 mL) at 0° C. was added NaH (625 mg, 15.6 mmol) in portions and the mixture was stirred at 0° C. for 10 minutes. Iodomethane (3.7 g 26 mmol) was added dropwise at 0° C. and the reaction mixture was stirred at room temperature for overnight. The reaction was quenched with ice-water (50 mL) and the resulting solid was collected by filtration. The solid was washed with water and dried under vacuum to afford the titled compound (2.6 g, yield: 86%) as a white solid. LCMS (ESI-MS): m/z 303.1 [M+H]$^+$.

c) 2-methoxy-4-((4-methoxybenzyl)oxy)benzoic Acid

To a solution of methyl 2-methoxy-4-((4-methoxybenzyl)oxy)benzoate (2.6 g, 8.6 mmol) in THF (10 mL) was added aqueous NaOH (4 M, 2 mL, 34.4 mmol) at 0° C. The reaction mixture was refluxed for 4 hours. Solvent was evaporated and the pH of the mixture was adjusted to 5-6 with aqueous diluted HCl. The mixture was extracted with ethyl acetate (50 mL×3). The combined organic layers were washed with 0.6 N aqueous HCl (100 mL), dried over $Na_2SO_4$, filtered and evaporated to afford the titled compound (1.6 g, yield: 65%) as a white solid. LCMS (ESI-MS): m/z 289.1 [M+H]$^+$.

d) 2-methoxy-4-((4-methoxybenzyl)oxy)benzoyl Chloride

To a solution of 2-methoxy-4-((4-methoxybenzyl)oxy) benzoic acid (200 mg 1.03 mmol) in dichloromethane (20 mL) was added DMF (2 μL) and oxalyl chloride (1.7 g, 13.8 mmol) at 0° C. under $N_2$. The reaction mixture stirred at room temperature for 30 minutes. Solvent was evaporated to provide the titled compound to use in the next step without further purification.

e) 2-methoxy-4-((4-methoxybenzyl)oxy)-N-(5-(thiophen-2-yl)-1,3,4-oxadiazol-2-yl)benzamide To a solution of 5-(thiophen-2-yl)-1,3,4-oxadiazol-2-amine (116 mg, 0.69 mmol) in THF (5 mL) was added NaH (60% in mineral oil, 110 mg, 2.76 mmol) at 0° C. under $N_2$. The reaction mixture was stirred at room temperature for 30 minutes, 2-methoxy-4-((4-methoxybenzyl)oxy) benzoyl chloride (211 mg, 0.69 mmol) was added into the mixture under 0° C. The reaction mixture was stirred at room temperature for overnight. The mixture was quenched with water (10 mL) and was extracted with ethyl acetate (10 mL×2). The combined organic layers were washed with brine (20 mL), dried over $Na_2SO_4$, filtered and evaporated. The residue was purified by preparative HPLC to afford the titled compound (60 mg, yield: 20%) as a white solid. LCMS (ESI-MS): m/z 438.1 [M+H]$^+$.

f) 4-hydroxy-2-methoxy-N-(5-(thiophen-2-yl)-1,3,4-oxadiazol-2-yl)benzamide

To a solution of 2-methoxy-4-((4-methoxybenzyl)oxy)-N-(5-(thiophen-2-yl)-1,3,4-oxadiazol-2-yl) benzamide (60 mg, 0.14 mmol) in DCM (2 mL) was added trifluoroacetic acid (2 mL) at room temperature. The reaction mixture was stirred at room temperature for 1 hour. DCM was evaporated under reduced pressure to give the titled compound (18 mg, yield: 42%) as a white solid. LCMS (ESI-MS): m/z 318.1 [M+H]$^+$; $^1$HNMR (300 MHz, DMSO-$d_6$): 610.89 (s, 1H), 10.41 (s, 1H), 7.94-7.92 (m, 1H), 7.77-7.69 (m, 2H), 7.31-7.26 (m, 1H), 6.58-6.49 (m, 2H), 3.89 (s, 3H).

Example 9

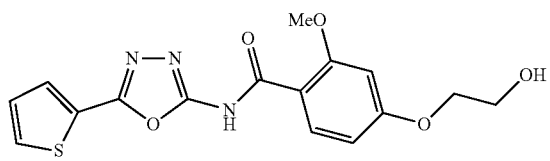

17

4-(2-hydroxyethoxy)-2-methoxy-N-(5-(thiophen-2-yl)-1,3,4-oxadiazol-2-yl)benzamide a) methyl 4-(2-(benzyloxy)ethoxy)-2-hydroxybenzoate To a solution of methyl 2,4-dihydroxybenzoate (5.0 g, 30 mmol) in DMF (100 mL) at 5° C. was added $K_2CO_3$ (4.3 g, 30 mmol). The mixture was stirred at room temperature for 1 hour and ((2-bromoethoxy)methyl)benzene (6.4 g 30 mmol) was added dropwise at 5° C. The reaction mixture was stirred at room temperature for overnight. The mixture was diluted with ethyl acetate (60 mL) and then washed with brine (200 mL×3). The combined the organic layers were dried over $Na_2SO_4$, filtered and evaporated. The residue was purified by column chromatography on silica gel (PE/EA=100:1 to 10:1) to afford the titled compound (2.16 g, yield: 24%) as a white solid.

b) methyl 4-(2-(benzyloxy)ethoxy)-2-methoxybenzoate

To a solution of methyl 4-(2-(benzyloxy)ethoxy)-2-hydroxybenzoate (1.8 g 5.7 mmol) in MeOH (5 mL) was added Pd/C (5%, 180 mg, 0.57 mmol) at room temperature. The reaction mixture was stirred at room temperature under a balloon pressure of hydrogen gas for 12 hours. Filter the reaction mixture and collect the filtrate. Evaporate the solvent in the filtrate and to afford the titled compound (900 mg, yield: 70%) as a white solid and was used in the next step without further purification.

c) Methyl 4-(2-((tert-butyldimethylsilyl)oxy)ethoxy)-2-methoxybenzoate

To a solution of methyl 4-(2-(benzyloxy)ethoxy)-2-methoxybenzoate (900 mg, 3.96 mmol) in anhydrous THF (30 mL) at 0° C. was added imidazole (320 mg, 4.7 mmol). TBSCl (661 mg, 4.38 mmol) was added and the mixture was stirred at room temperature for overnight. The reaction was quenched with water (10 mL) and was extracted with EA (10 mL-2). The combined organic layers were washed with brine (20 mL), dried over $Na_2SO_4$, filtered and concentrated in vacuo to afford the titled compound (680 mg, yield: 50%) as a white solid. LCMS (ESI-MS): m/z 327.1 $[M+H]^+$.

d) 4-(2-((tert-butyldimethylsilyl)oxy)ethoxy)-2-methoxybenzoic Acid

To a solution of methyl 4-(2-((tert-butyldimethylsilyl)oxy)ethoxy)-2-methoxybenzoate (680 mg, 2 mmol) in THF (10 mL) was added aqueous NaOH (4M, 2 mL, 8 mmol) at 0° C. The reaction mixture was refluxed for 4 hours. Solvent was evaporated and the pH of the mixture was adjusted to 5-6 with diluted aqueous HCl. The mixture was extracted with ethyl acetate (10 mL×3). The combined organic layers were washed with 0.6 N aqueous HCl (20 mL), dried over $Na_2SO_4$, filtered and evaporated to afford the titled compound (450 mg, yield: 66%) as a white solid and was used in the next step without further purification.

e) 4-(2-((tert-butyldimethylsilyl)oxy)ethoxy)-2-methoxybenzoyl Chloride

To a solution of 4-(2-((tert-butyldimethylsilyl)oxy)ethoxy)-2-methoxybenzoic acid (350 mg 1.07 mmol) in DCM (10 mL) at 0° C., was added DMF (2 mL) and oxalyl chloride (2.73 g, 21.5 mmol) under $N_2$. The reaction mixture stirred at room temperature for 30 minutes. Evaporate solvent under reduced pressure to provide title compound and was used in the next step without further purification.

f) 4-(2-((tert-butyldimethylsilyl)oxy)ethoxy)-2-methoxy-N-(5-(thiophen-2-yl)-1,3,4-oxadiazol-2-yl)benzamide To a solution of 5-(thiophen-2-yl)-1,3,4-oxadiazol-2-amine (112 mg, 0.68 mmol) in THF (5 mL) was added NaH (60% in mineral oil, 70 mg, 2.72 mmol) at 0° C. under $N_2$. The reaction mixture was stirred at room temperature for 30 minutes, 4-(2-((tert-butyldimethylsilyl)oxy)ethoxy)-2-methoxy benzoyl chloride (370 mg, 1.07 mmol) was added into the mixture under 0° C. The reaction mixture was stirred at room temperature for overnight. The mixture was quenched with water (5 mL) and the mixture was extracted with ethyl acetate (10 mL×2). The combined organic layers were washed with brine (30 mL), dried over $Na_2SO_4$, filtered and evaporated. The residue was purified by preparative HPLC to obtain the titled compound (20 mg, yield: 17%) as a white solid.

g) 4-(2-hydroxyethoxy)-2-methoxy-N-(5-(thiophen-2-yl)-1,3,4-oxadiazol-2-yl)benzamide To a solution of 4-(2-((tert-butyldimethylsilyl)oxy)ethoxy)-2-methoxy-N-(5-(thiophen-2-yl)-1,3,4-oxadiazol-2-yl)benzamide (20 mg, 0.04 mmol) in DCM (2 mL) was added TFA (2 mL) at room temperature for 12 hours. The reaction was filtered and solvent in the filtrate was evaporated under reduced pressure to give the titled compound (7 mg, yield: 46%) as a white solid. LCMS (ESI-MS): m/z 360.1 $[M+H]^+$. $^1$HNMR (400 MHz, DMSO-$d_6$): δ 11.06 (s, 1H), 7.95 (s, 1H), 7.78-7.75 (m, 2H), 7.31-7.29 (m, 1H), 6.72-6.69 (m, 2H), 4.92 (t, J=5.6 Hz, 1H), 4.12 (t, J=4.8 Hz, 2H), 3.93 (s, 3H), 3.77-3.74 (m, 2H).

Example 10

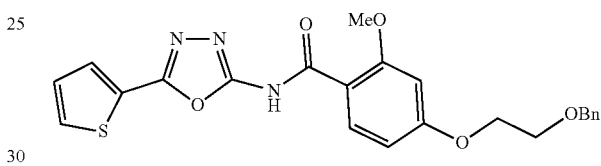

18

4-(2-(benzyloxy)ethoxy)-2-methoxy-N-(5-(thiophen-2-yl)-1,3,4-oxadiazol-2-yl)benzamide a) Methyl 4-(2-(benzyloxy)ethoxy)-2-hydroxybenzoate To a solution of methyl 2,4-dihydroxybenzoate (5.0 g, 30 mmol) in DMF (100 mL) at 5° C., was added $K_2CO_3$ (4.3 g, 3 mmol). The mixture was stirred at room temperature for 1 hour and ((2-bromoethoxy)methyl)benzene (6.4 g, 30 mmol) was added dropwise at 5° C. The reaction mixture was stirred at room temperature overnight. The mixture was diluted with ethyl acetate (60 mL) and then washed with brine (200 mL×3), the combined organic layers were dried over $Na_2SO_4$, filtered and solvent was evaporated. The residue was purified by column chromatography on silica gel (PE/EA=100:1 to 10:1) to afford the titled compound (2.16 g, yield: 24%) as a white solid.

b) 4-(2-(benzyloxy)ethoxy)-2-methoxybenzoic Acid

To a solution of methyl 4-(2-(benzyloxy)ethoxy)-2-methoxybenzoate (2.16 g 7.1 mmol) in THF (50 mL) was added aqueous NaOH (5 mL, 1.14 g 28.5 mmol) at 0° C. The reaction mixture was refluxed for 4 hours. THF was evaporated under reduced pressure, the pH of the mixture was adjusted to 5-6 with diluted HCl. The mixture was extracted with EA (50 mL×3). The combined organic layers were washed with aqueous HCl (0.6 N, 100 mL), dried over $Na_2SO_4$, filtered and evaporated to afford the titled compound (1.8 g, yield: 63%) as a white solid. LCMS (ESI-MS): m/z 303.1 $[M+H]^+$.

c) 4-(2-(benzyloxy)ethoxy)-2-methoxybenzoyl Chloride

To a solution of 4-(2-(benzyloxy)ethoxy)-2-methoxybenzoic acid (300 mg 1.03 mmol) in DCM (20 mL) was added DMF (2 mL) and $(COCl)_2$ (2.5 g, 20.7 mmol) at 0° C. under $N_2$. The reaction mixture stirred at room temperature for 30 min. DCM was evaporated to provide the titled compound and used in the next step without further purification.

d) 4-(2-(benzyloxy)ethoxy)-2-methoxy-N-(5-(thiophen-2-v)-1,3,4-oxadiazol-2-yl)benzamide To a solution of 5-(thiophen-2-yl)-1,3,4-oxadiazol-2-amine (534 mg 1.67 mmol) in THF (20 mL) was added NaH (60% in mineral oil, 166 mg, 4.16 mmol) at 0° C. under $N_2$. The reaction mixture stirred at room temperature for 30 minutes and 4-(2-(benzyloxy)ethoxy)-2-methoxybenzoyl chloride (280 mg, 1.67 mmol) was added into the mixture under 0° C. After addition, the reaction mixture was stirred at room temperature overnight. The mixture was quenched with water (10 mL), which was extracted with EA (20 mL×2). The combined organic layer was washed with brine (40 mL), dried over $Na_2SO_4$, filtered and evaporated. The residue was purified by preparative HPLC, to afford the titled compound (40 mg, yield: 5%) as a white solid. LCMS (ESI-MS): m/z 452.1 [M+H]$^+$; $^1$HNMR (300 MHz, DMSO-$d_6$): δ11.08 (s, 1H), 7.93 (d, J=4.5 Hz, 1H), 7.78-7.75 (m, 2H), 7.37-7.27 (m, 6H), 6.74-6.68 (m, 2H), 4.58 (s, 2H), 4.45-4.39 (m, 2H), 3.92 (s, 3H), 3.82-3.76 (m, 2H).

Example 11

19

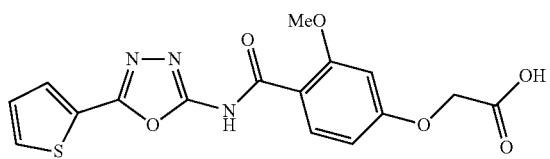

2-(3-methoxy-4-((5-(thiophen-2-yl)-1,3,4-oxadiazol-2-yl)carbamoyl)phenoxy)acetic Acid a) 2-methoxy-4-(2-oxoethoxy)-N-(5-(thiophen-2-yl)-1,3,4-oxadiazol-2-yl)benzamide To a solution of 4-(2,3-dihydroxypropoxy)-2-methoxy-N-(5-(thiophen-2-yl)-1,3,4-oxadiazol-2-yl)benzamide (47 mg, 0.12 mmol) in dichloromethane (2 mL), $NaIO_4$ (34 mg, 0.16 mmol) were added and the mixture was stirred overnight at room temperature. The reaction mixture was extracted with ethyl acetate (30 mL×3). The combined organic layers were washed with brine, dried over $Na_2SO_4$, filtered and concentrated under vacuum to give the titled compound (60 mg, 100%) as a white solid which was used in the next step without further purification.

b) 2-(3-methoxy-4-((5-(thiophen-2-yl)-1,3,4-oxadiazol-2-yl)carbamoyl)phenoxy)acetic Acid To a solution of 2-methox-4-(2-oxoethoxy)-N-(5-(thiophen-2-yl)-1,3,4-oxadiazol-2-yl)benzamide (60 mg, 0.17 mmol) in acetone (2 mL), $NaClO_2$ (104 mg, 0.92 mmol) and $NaH_2PO_4$ (61 mg, 0.50 mmol) were added. The mixture was stirred for 12 hours at room temperature. The reaction mixture was extracted with ethyl acetate (30 mL×3). The combined organic layers were washed with brine, dried over $Na_2SO_4$, filtered and concentrated under vacuum. The residue was purified by preparative HPLC to give the titled compound (4 mg, yield: 6%) as a white solid. LCMS (ESI-MS): m/z 376.0 [M+H]$^+$; $^1$H NMR (400 MHz, DMSO-dr): δ 13.10 (s, br, 1H), 11.40 (s, 1H), 7.93 (d, J=8 Hz, 1H), 7.60 (d, J=8 Hz, 1H), 7.20 (d, J=8 Hz, 1H), 7.29 (d, J=8.0 Hz, 1H), 6.74 (s, 1H), 6.70-6.64 (m, 1H), 4.80 (s, 2H), 3.91 (s, 3H).

Example 12

20

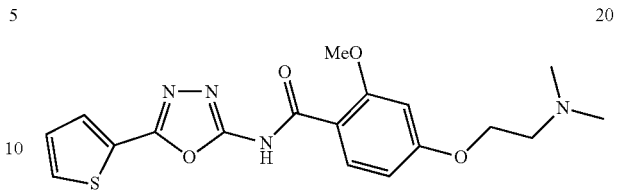

4-(2-(dimethylamino)ethoxy)-2-methoxy-N-(5-(thiophen-2-yl)-1,3,4-oxadiazol-2-yl)benzamide To a solution of 2-methoxy-4-(2-oxoethoxy)-N-(5-(thiophen-2-yl)-1,3,4-oxadiazol-2-yl)benzamide (50 mg, 0.14 mmol) in DCM (2 mL). Dimethylamine (0.4 mL, 0.70 mmol) and acetic acid (0.1 mL) were added. The mixture was allowed to react for 1 hour at room temperature. NaBH(OAc)$_3$ (45 mg, 0.21 mmol) were added and the mixture was stirred for overnight at room temperature. The reaction mixture was extracted with ethyl acetate (30 mL×3). The combined organic layers were washed with brine, dried over $Na_2SO_4$ and concentrated under vacuum. The residue was purified by preparative HPLC to give the titled compound (4 mg, yield: 7%) as a white solid. LCMS (ESI-MS): m/z 388.9 [M+H]$^+$; $^1$H NMR (400 MHz, CD$_3$OD): δ 8.04 (d, J=8.4 Hz, 1H), 7.85-7.79 (m, 2H), 7.28 (t, J=4.8 Hz, 1H), 6.83-6.81 (m, 2H), 4.51 (t, J=4.4 Hz, 1H), 4.10 (s, 3H), 3.68 (t, J=4.4 Hz, 2H), 3.05 (s, 6H).

Example 13

21

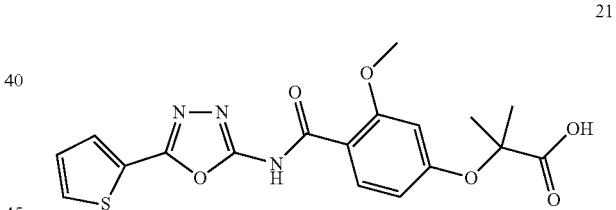

2-(3-methoxy-4-((5-(thiophen-2-yl)-1,3,4-oxadiazol-2-yl)carbamoyl)phenoxy)-2-methylpropanoic Acid a) Ethyl 2-(4-formyl-3-methoxyphenoxy)-2-methylpropanoate To a suspension of 4-hydroxy-2-methoxybenzaldehyde (0.04 mL, 0.3 mmol) and ethyl 2-bromo-2-methylpropanoate (0.14 mL, 0.99 mmol) in DMF (1 mL) was added $Cs_2CO_3$ (321.22 mg, 0.99 mmol) at 25° C. The reaction was stirred at 50° C. for 16 hours. The mixture was diluted with $H_2O$ (5 mL) and extracted with ethyl acetate (5 mL×3). The combined organic layers were dried over $MgSO_4$ and filtered. The filtrate was concentrated in vacuo. The residue was dissolved with DCM (1 mL) and washed with NaOH (1 M, 1 mL×3), the combined organic layers was separated and the solvent was removed in vacuo to give the titled compound (50 mg, 51%) as a yellow oil. LC-MS (ESI): m/z 267.0 [M+H]$^+$.

b) 4-((1-ethoxy-2-methyl-1-oxopropan-2-yl)oxy)-2-methoxybenzoic Acid

To a solution of ethyl 2-(4-formyl-3-methoxyphenoxy)-2-methylpropanoate (50 mg, 0.17 mmol) in t-BuOH (1.50 mL) was added NaClO$_2$ (141 mg, 1.6 mmol) and NaH$_2$PO$_4$ (120 mg, 1.1 mmol) in H$_2$O (0.67 mL) at 25° C., the mixture was stirred at 25° C. for 16 hours. The mixture was a yellow solution. The mixture was diluted with H$_2$O (5 mL) and extracted with EtOAc (5 mL×3). The combined organic layers were dried over MgSO$_4$, filtered and filtrate was concentrated in vacuo to give the titled compound (35 mg, yield: 66%) as a yellow solid. LC-MS (ESI): m/z 238.2 [M+H]$^+$.

c) Ethyl 2-(3-methoxy-4-((5-(thiophen-2-yl)-1,3,4-oxadiazol-2-yl)carbamoyl)phenoxy)-2-methyl Propanoate To a suspension of 4-((1-ethoxy-2-methyl-1-oxopropan-2-yl)oxy)-2-methoxybenzoic acid (35 mg, 0.11 mmol), 5-(thiophen-2-yl)-1,3,4-oxadiazol-2-amine (28 mg, 0.17 mmol) and TEA (60 mL, 0.45 mmol) in ethyl acetate (1 mL), was added T$_3$P (266 mL, 0.45 mmol) at 25° C. and the reaction mixture was stirred at 80° C. for 16 hours. The mixture was diluted with H$_2$O (1 mL) and extracted with ethyl acetate (2 mL×3). The combined organic layers were dried over MgSO$_4$ and filtered, the filtrate was concentrated in vacuo to give the titled compound (65 mg, yield: 68%) as a yellow oil. LC-MS (ESI): m/z 432.2 [M+H]$^+$.

d) 2-(3-methoxy-4-((5-(thiophen-2-yl)-1,3,4-oxadiazol-2-Yl)carbamoyl)phenoxy)-2-methylpropanoic Acid To a solution of ethyl 2-(3-methoxy-4-((5-(thiophen-2-yl)-1,3,4-oxadiazol-2-yl)carbamoyl) phenoxy)-2-methylpropanoate (65 mg, 0.075 mmol) in THF (0.5 mL) and H$_2$O (0.5 mL) was added UGH (7.33 μL, 0.26 mmol) at 25° C. The mixture was stirred at 50° C. for 16 hours. The solvent was removed in vacuo. The residue was dissolved with H$_2$O (3 mL) and the pH of the mixture was adjusted to 4 using aqueous 1N HCl. The mixture was purified by preparative HPLC (Column: Phenomenex Gemini C18 250*50 mm*10 um; mobile phase: [water (0.225% FA)-ACN]; B %: 38%-58%, 10 min) to give the titled compound (5 mg, yield: 16%) as a white solid. LC-MS (ESI): m/z 404.1 [M+H]$^+$; $^1$H NMR (400 MHz, DMSO-d$_6$) δ 11.17 (br s, 1H), 7.94 (d, J=4.0 Hz, 1H), 7.76 (d, J=2.7 Hz, 1H), 7.69 (d, J=8.7 Hz, 1H), 7.29 (dd, J=3.8, 4.9 Hz, 1H), 6.61 (d, J=2.1 Hz, 1H), 6.48 (dd, J=2.2, 8.7 Hz, 1H), 3.87 (s, 3H), 1.59 (s, 6H).

Example 14

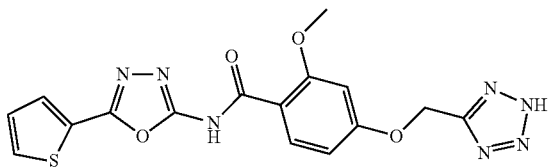

22

4-((2H-tetrazol-5-yl)methoxy)-2-methoxy-N-(5-(thiophen-2-yl)-1,3,4-oxadiazol-2-yl)benzamide a) Methyl 4-(cyanomethoxy)-2-hydroxybenzoate To a solution of methyl 2,4-dihydroxybenzoate (5.0 g, 30 mmol) and K$_2$CO$_3$ (4.32 g, 31 mmol) in DMF (50 mL) was added 2-bromoacetonitrile (3.57 g, 30 mmol) at 0° C. The mixture was stirred under an atmosphere of nitrogen at 25° C. for 12 hours. The mixture was filtered, and the solvent was concentrated in vacuo. The residue was purified by flash silica gel chromatography (ISCO®; 80 g sepaFlash® silica flash column, eluent of 0-50% ethyl acetate/petroleum ether gradient @ 30 mL/min) to obtain the titled compound (1.6 g, yield: 26%) as a white solid. LC-MS (ESI): m/z 207.9 [M+H]$^+$.

b) Methyl 4-(cyanomethoxy)-2-methoxybenzoate

To a solution of methyl 4-(cyanomethoxy)-2-hydroxybenzoate (1.0 g, 4.8 mmol) in DMF (20 mL) was added NaH (60% in mineral oil, 0.25 g, 6.3 mmol) at 0° C. The solution was stirred at 25° C. for 0.5 hour and iodomethane (0.89 g, 6.3 mmol) was added dropwise at 0° C. The reaction was stirred under N$_2$ at 25° C. for 12 hours. Water (60 mL) was added and the mixture was extracted with EtOAc (60 mL×3). The combined organic layers were washed with brine (20 mL), dried over Na$_2$SO$_4$, filtered and concentrated to give the titled compound (1.05 g, 98%) was obtained as a brown oil. LC-MS (ESI): m/z 222.1 [M+H]$^+$.

c) Methyl 4-((2H-tetrazol-5-yl)methoxy)-2-methoxybenzoate

To a solution of methyl 4-(cyanomethoxy)-2-methoxybenzoate (1.0 g, 4.5 mmol) and trimethylsilylazide (1.0 g, 9.0 mmol) in toluene (20 mL) was added dibutylstannanone (225 mg, 0.90 mmol) at 0° C. The mixture was stirred under N$_2$ at 120° C. for 12 hours. The mixture was concentrated to about 3 mL, PE (12 mL) and MTBE (3 mL) was added and stirred at 25° C. for 3 hours to obtain a white suspension. The solid was filtered to obtain the titled compound (1.0 g, 84%) as a white solid. LC-MS (ESI): m/z 264.9 [M+H]$^+$.

d) 4-((2H-tetrazol-5-yl)methoxy)-2-methoxybenzoic Acid

To a solution of methyl 4-((2H-tetrazol-5-yl)methoxy)-2-methoxybenzoate (100 mg, 0.38 mmol) in THF (1 mL) was added 1M aqueous LiOH (0.8 mL, 0.8 mmol). The reaction was stirred under N$_2$ at 50° C. for 12 hr. The mixture was concentrated and the pH of the residue was adjusted to 3~4 with aqueous 1M HCl to afford a solid. The solid was filtered to give the titled compound (70 mg, 73.9%) as a white solid. LC-MS (ESI): m/z 251.1 [M+H]$^+$.

e) 4-((2H-tetrazol-5-yl)methoxy)-2-methoxy-N-(5-(thiophen-2-yl)-1,3,4-oxadiazol-2-yl) Benzamide To a solution of 4-((2H-tetrazol-5-yl)methoxy)-2-methoxybenzoic acid (50 mg, 0.20 mmol), 5-(thiophen-2-yl)-1,3,4-oxadiazol-2-amine (67 mg, 0.40 mmol) and TEA (0.11 mL, 0.8 mmol) in ethyl acetate (5 mL) was added T$_3$P (50% in EA, 1.0 mL, 1.6 mmol) at 0° C. The mixture was stirred under N$_2$ at 80° C. for 12 hours. Water (20 mL) was added and the mixture was extracted with EtOAc (30 mL/3). The combined organic layers were dried over Na$_2$SO$_4$, filtered and concentrated. The residue was purified by preparative HPLC (column: Boston Uni C18 40*150*5 um; mobile phase: water (0.225% FA)-ACN; B %: 18%-58%. 10 min) to afford the titled compound (6 mg, yield: 7.5%) as a yellow solid. LC-MS (ESI): m/z 400.0 [M+H]$^+$; $^1$H NMR (400 MHz, DMSO-d$_6$) δ 7.99-7.91 (m, 1H), 7.76 (d, J=3.5 Hz, 1H), 7.38 (d, J=3.1 Hz, 1H), 7.33-7.26 (m, 2H), 7.17 (d, J=9.0 Hz, 1H), 5.45 (s, 2H), 3.85 (s, 3H).

Example 15

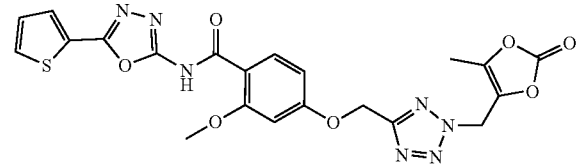

23

2-methoxy-4-((2-((5-methyl-2-oxo-1,3-dioxol-4-yl)methyl)-2H-tetrazol-5-yl)methoxy)-N-(5-(thiophen-2-yl)-1,3,4-oxadiazol-2-yl)benzamide

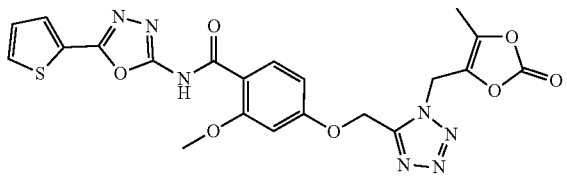

24

2-methoxy-4-((1-((5-methyl-2-oxo-1,3-dioxol-4-yl)methyl)-1H-tetrazol-5-yl)methoxy)-N-(5-(thiophen-2-yl)-1,3,4-oxadiazol-2-yl)benzamide To a solution of 4-((2H-tetrazol-5-yl)methoxy)-2-methoxy-N-(5-(thiophen-2-yl)-1,3,4-oxa-diazol-2-yl)benzamide (20 mg, 0.05 mmol), and 4-(chloromethyl)-5-methyl-1,3-dioxol-2-one (5 μL, 0.045 mmol) in acetonitrile (1 mL) was added $K_2CO_3$ (8 mg, 0.06 mmol) and KI (5 mg, 0.03 mmol). The mixture was allowed to stir under $N_2$ at 50° C. for 1.5 hours. Second portion of 4-(chloromethyl)-5-methyl-1,3-dioxol-2-one (5 μL, 0.045 mmol) in acetonitrile (1 mL) was added and the reaction was allowed to stir at 50° C. for another 1.5 hours. Third portion of 4-(chloromethyl)-5-methyl-1,3-dioxol-2-one (5 μL, 0.045 mmol) in acetonitrile (1 mL) was added and the reaction was allowed to stir at 50° C. for 16 hours. The mixture was diluted with acetonitrile (10 mL) and filtered. The solvent was removed under $N_2$. The residue was purified by preparative HPLC (Column: YMC-Actus Triart C18 150*30 mm*7 um; mobile phase: [water (0.225% FA)-ACN]; B %: 38%-58%, 10 min) to give the product as two isomers as in two fractions. Isomer 1: (HPLC: RT=3.97 min, 4 mg, yield: 15%), LC-MS (ESI): m/z 512.2 [M+H]$^+$; $^1$H NMR (400 MHz, DMSO-$d_6$) δ 7.93 (d, J=5.1 Hz, 1H), 7.73 (br d, J=3.1 Hz, 1H), 7.40 (d, J=2.6 Hz, 1H), 7.33-7.23 (m, 2H), 7.21-7.13 (m, 1H), 5.80 (s, 2H), 5.57 (s, 2H), 3.84 (s, 3H), 2.18 (s, 3H); and isomer 2 (HPLC: RT=4.08 min, 3 mg, yield 12%) as white solid, LC-MS (ESI): m/z 512.2 [M+H]$^+$; $^1$H NMR (400 MHz, DMSO-$d_6$) δ 7.92 (br d, J=4.9 Hz, 1H), 7.73 (br s, 1H), 7.34 (br s, 1H), 7.31-7.20 (m, 2H), 7.17-7.11 (m, 1H), 6.03 (s, 2H), 5.41 (s, 2H), 3.83 (s, 3H), 2.27 (s, 3H).

Example 16

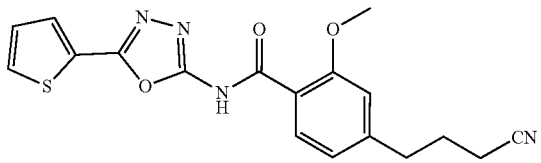

25

4-(3-cyanopropyl)-2-methoxy-N-(5-(thiophen-2-yl)-1,3,4-oxadiazol-2-yl)benzamide
a) 5-(thiophen-2-yl)-1,3,4-oxadiazol-2-amine To a mixture of thiophene-2-carbohydrazide (10.5 g, 66.5 mmol) in $H_2O$ (500 mL) was added BrCN (9.78 mL, 133 mmol) in acetonitrile (20 mL) dropwise at 25° C. The mixture was stirred at 25° C. for 16 hours. The mixture was filtered, and the white solid was washed with water to give the titled compound (4.8 g, yield: 30%) as a yellow solid. LC-MS (ESI): m/z 168.0 [M+H]$^+$.

b) 4-bromo-2-methoxy-N-(5-(thiophen-2-yl)-1,3,4-oxadiazol-2-yl)benzamide

To a suspension of 5-(thiophen-2-yl)-1,3,4-oxadiazol-2-amine (500 mg, 2.84 mmol), 4-bromo-2-methoxybenzoic acid (984 mg, 4.26 mmol) and trimethylamine (1.58 mL, 11.4 mmol) in ethyl acetate (20 mL), was added $T_3P$ (3.38 mL, 11.4 mmol) at 25° C., and the reaction mixture was stirred at 80° C. for 16 hours. The mixture was diluted with $H_2O$ (10 mL) and was extracted with ethyl acetate (10 mL×3). The combined organic layers were dried over $MgSO_4$, filtered and concentrated under reduced pressure. The residue was washed with ethyl acetate (3 mL) and the solid was collected to give the titled compound (730 mg, yield: 64%) as a yellow solid. LC-MS (ESI): m/z 380.0 [M+H]$^+$.

c) 4-(3-cyanopropyl)-2-methoxy-N-(5-(thiophen-2-yl)-1,3,4-oxadiazol-2-yl)benzamide To a mixture of 4-bromo-2-methoxy-N-(5-(thiophen-2-yl)-1,3,4-oxadiazol-2-yl)benzamide (200 mg, 0.5 mmol) and (3-cyanopropyl)zinc(II) bromide (1 mL, 0.5 M solution in THF, 1.05 mmol) in THF (4 mL) was added Pd(PPh$_3$)$_4$ (30 mg, 0.03 mmol) at 25° C. under $N_2$. The mixture was stirred at 100° C. for 30 min in microwave. The mixture was filtered by silica and solvent was removed in vacuo. The residue was purified by preparative HPLC (Column: Phenomenex Gemini-NX 150*30 mm*5 um; mobile phase: [water (0.05% ammonia hydroxide v/v)-ACN]; B %: 30%-70%, 10 min) to give a solid. The solid was washed with ethyl acetate (3 mL) and collected the solid to give the titled compound (21 mg, yield: 11%) as a white solid. LC-MS (ESI): m/z 369.0 [M+H]$^+$, $^1$H NMR (DMSO-$d_6$, 400 MHz): δ 11.40 (br s, 1H), 7.93 (d, J=4.9 Hz, 1H), 7.74 (d, J=3.0 Hz, 1H), 7.63 (d, J=8.0 Hz, 1H), 7.28 (t, J=4.3 Hz, 1H), 7.08 (s, 1H), 6.95 (br d, J=8.3 Hz, 1H), 3.90 (s, 3H), 2.74 (br t, J=7.7 Hz, 2H), 2.54 (br s, 2H), 1.84-1.99 (m, 2H).

Example 17

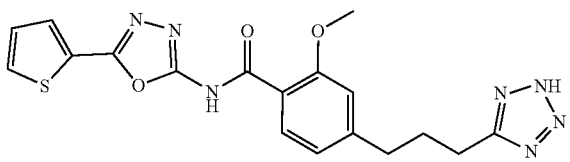

26

4-(3-(2H-tetrazol-5-yl)propyl)-2-methoxy-N-(5-(thiophen-2-yl)-1,3,4-oxadiazol-2-yl)benzamide To a solution of 4-(3-cyanopropyl)-2-methoxy-N-(5-(thiophen-2-yl)-1,3,4-oxadiazol-2-yl)benzamide (200 mg, 0.2 mmol) and $Bu_2SnO$ (7.21 mL, 43 mmol) in toluene (2 mL) was added TMSN$_3$ (50 mg, 0.4 mmol) at 25° C. The mixture was stirred at 120° C. for 16 hours. The mixture remove solvent in vacuo, and dissolved with DMSO (2 mL), and purified by preparative HPLC (Column: Phenomenex Gemini-NX 150*30 mm*5 um; mobile phase: [water (0.05% ammonia hydroxide v/v)-ACN]; B %: 30%-70%, 10 min) to give the titled compound (4.6 mg, 5.1%) as a white solid. LC-MS (ESI): m/z 412.1 [M+H]$^+$; $^1$H NMR (DMSO-de, 400 MHz): δ 7.93 (d, J=5.0 Hz, 1H), 7.75 (d, J=3.3 Hz, 1H), 7.64 (d, J=8.0 Hz, 1H), 7.24-7.34 (m, 1H), 7.07 (s, 1H), 6.96 (d, J=8.0 Hz, 1H), 3.90 (s, 3H), 2.90 (br, t, J=7.5 Hz, 2H), 2.64-2.76 (m, 2H), 2.01-2.12 (m, 2H).

Example 18

27

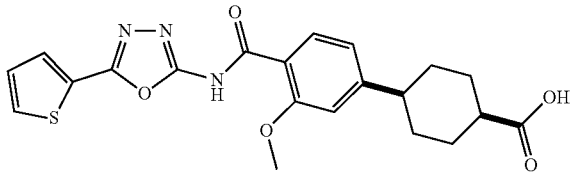

Cis-4-(3-methoxy-4-((5-(thiophen-2-yl)-1,3,4-oxadiazol-2-yl)carbamoyl)phenyl)cyclohexane-1-carboxylic Acid

28

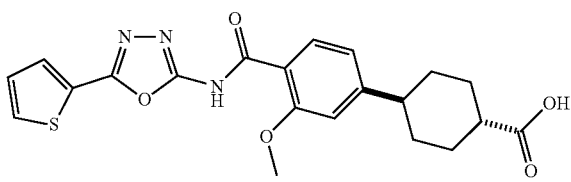

Trans-4-(3-methoxy-4-((5-(thiophen-2-yl)-1,3,4-oxadiazol-2-yl)carbamoyl)phenyl)cyclohexane-1-carboxylic Acid a) 4'-(ethoxycarbonyl)-3-methoxy-2',3',4',5'-tetrahydro-[1,1'-biphenyl]-4-carboxylic Acid To a suspension of 4-bromo-2-methoxybenzoic acid (300 mg, 1.3 mmol), ethyl 4-(4,4,5,5-tetramethyl-1,3,2-dioxaborolan-2-yl)cyclohex-3-ene-1-carboxylate (437 mg, 1.56 mmol) and $K_2CO_3$ (0.40 mL, 3.9 mmol) in dioxane (13 mL) and $H_2O$ (1.3 mL) was added Pd(dppf)Cl$_2$ CH$_2$Cl$_2$ (530 mg, 0.65 mmol) at 25° C. under $N_2$. The mixture was stirred at 105° C. for 16 hours. The mixture was filtered and the cake washed with ethyl acetate (5 mL×2). The filtrate was extracted with ethyl acetate (5 mL×3) and the combined organic layers were dried over MgSO$_4$, filtered and concentrated in vacuo. The residue was washed with ethyl acetate (3 mL) and the solid was obtained by filtration to give the titled compound (200 mg, yield: 38%) as a brown solid. LC-MS (ESI): m/z 305.2 [M+H]$^+$.

b) 4-(4-(ethoxycarbonyl)cyclohexyl)-2-methoxybenzoic Acid

To a suspension of 4'-(ethoxycarbonyl)-3-methoxy-2',3',4',5'-tetrahydro-[1,1'-biphenyl]-4-carboxylic acid (20 mg, 0.05 mmol) in DCM (3 mL) was added triethyl silane (74 mL, 0.46 mmol), trifluoroacetic acid (17 mL, 0.23 mmol) and Pd(OAc)$_2$ (15 mg, 0.07 mmol) at 25° C., and stirred at 25° C. for 16 hours. The mixture was filtered and washed with DCM (2 mL). The solvent was removed in vacuo to give the titled compound (26 mg, yield: 92%) as a yellow oil. LC-MS (ESI): m/z 307.2 [M+H]$^+$.

c) Ethyl 4-(3-methoxy-4-((5-(thiophen-2-yl)-1,3,4-oxadiazol-2-yl)carbamoyl)phenyl)cyclohexane-1-carboxylate To a suspension of 5-(thiophen-2-yl)-1,3,4-oxadiazol-2-amine (20 mg, 0.12 mmol), 4-(4-(ethoxycarbonyl)cyclohexyl)-2-methoxybenzoic acid (55 mg, 0.14 mmol) and triethyl amine (66 mL, 0.5 mmol) in ethyl acetate (1 mL), was added T$_3$P (285 mL, 0.5 mmol) at 25° C. The reaction mixture was stirred at 80° C. for 16 hours. The mixture was diluted with $H_2O$ (3 mL) and the mixture was extracted with ethyl acetate (3 mL×3), the combined organic layers were dried over MgSO$_4$, filtered and concentrated in vacuo to give the titled compound (80 mg, yield: 88%) as a yellow oil. LC-MS (ESI): m/z 456.2 [M+H]$^+$.

d) 4-(3-methoxy-4-((5-(thiophen-2-yl)-1,3,4-oxadiazol-2-yl)carbamoyl)phenyl)cyclohexane-1-carboxylic Acid To a solution of ethyl 4-(3-methoxy-4-((5-(thiophen-2-yl)-1,3,4-oxadiazol-2-yl)carbamoyl) phenyl)cyclohexane-1-carboxylate (80 mg, 0.11 mmol) in THF (0.5 mL) and $H_2O$ (0.5 mL) was added LiOH (1 mg, 0.367 mmol) at 25° C. The mixture was stirred at 50° C. for 16 hours. The solvent was removed in vacuo and the residue was dissolved with $H_2O$ (3 mL). Adjusted the pH of the mixture to 4~5 by adding aqueous 1N HCl and mixture was purified by preparative HPLC (Column: Phenomenex Gemini-NX 150*30 mm*5 um; mobile phase: [water (0.05% ammonia hydroxide v/v)-ACN]; B %: 0%-40%, 10 min) to give the titled compound as a separated pair of regioisomer: Isomer 1 (HPLC: RT=4.06 min, 5.8 mg, yield: 11%) as a white solid: LC-MS (ESI): m/z 428.2 [M+H]$^+$; $^1$H NMR (400 MHz, DMSO-d$_6$) δ=7.84 (br s, 1H), 7.70 (br s, 1H), 7.62 (s, 1H), 7.26 (t, J=4.4 Hz, 1H), 6.95 (s, 2H), 3.87 (s, 3H), 2.10-2.10 (m, 1H), 2.07 (br s, 1H), 1.91 (s, 1H), 1.63-1.42 (m, 6H), 1.27 (s, 2H); and isomer 2 (HPLC: RT=4.16 min, 5 mg, yield: 10%) as a white solid. LC-MS (ESI): m/z 428.2 [M+H]$^+$; $^1$H NMR (400 MHz, DMSO-d$_6$) δ 7.85 (s, 1H), 7.71 (s, 1H), 7.64 (s, 1H), 7.26 (d, J=5.0 Hz, 1H), 6.94 (s, 2H), 3.90 (br s, 3H), 2.15 (br s, 2H), 1.79-1.63 (m, 6H), 1.27 (br s, 2H).

Example 19

29

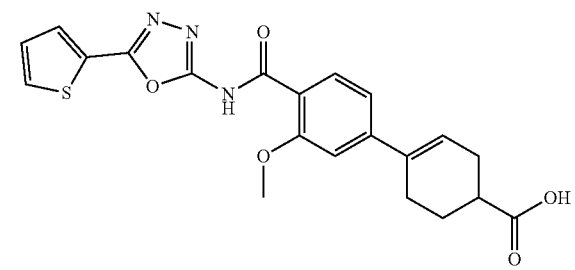

3'-methoxy-4'((5-(thiophen-2-yl)-1,3,4-oxadiazol-2-yl)carbamoyl)-2,3,4,5-tetrahydro-[1,1-biphenyl]-4-carboxylic Acid To a solution of ethyl 3'-methoxy-4'-((5-(thiophen-2-yl)-1,3,4-oxadiazol-2-yl)carbamoyl)-2,3,4,5-tetrahydro-[1,1'-biphenyl]-4-carboxylate (20 mg, 0.04 mmol) in $H_2O$ (0.25 mL) and THF (0.25 mL) was added LiOH (5.18 mg, 0.12 mmol) at 25° C., the mixture was stirred at 50° C. for 16 hours. The solvent was evaporated in vacuo and the residue was dissolved with $H_2O$ (3 mL). The pH of the mixture was adjusted to pH=4 and the mixture was purified by preparative HPLC (Column: Diamonsil C18 150*30 mm*5 um; mobile phase: [water (0.225% FA)-ACN]; B %: 38%-78%, 10 min) to give the titled compound (3.2 mg, yield: 21%) as a white solid. LC-MS (ESI): m/z 426.0 [M+H]$^+$; $^1$H NMR (DMSO-d$_6$, 400 MHz): δ 7.94 (d, J=3.9 Hz, 1H), 7.76 (d, J=2.6 Hz, 1H), 7.67 (d, J=7.9 Hz, 1H), 7.27-7.33 (m, 1H), 7.12-7.19 (m, 2H), 6.33-6.43 (m, 1H), 3.94 (s, 3H), 2.56-

2.65 (m, 1H), 2.46 (br s, 2H), 2.36-2.42 (m, 1H), 2.11 (br d, J=12.0 Hz, 1H), 1.73 (br s, 1H).

Example 20

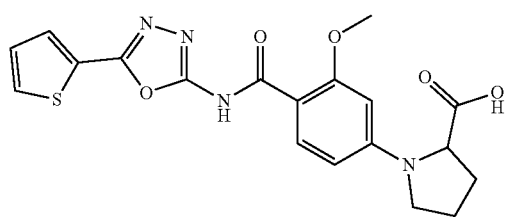

(3-methoxy-4-((5-(thiophen-2-yl)-1,3,4-oxadiazol-2-yl)carbamoyl)phenyl)proline

To a suspension of 4-bromo-2-methoxy-N-(5-(thiophen-2-yl)-1,3,4-oxadiazol-2-yl)benzamide (20 mg, 0.053 mmol) and proline (0.02 mL, 0.16 mmol) in DMSO (0.5 mL) was added CuI (1 mg, 0.005 mmol) and $Cs_2CO_3$ (34 mg, 0.1 mmol) under $N_2$. The mixture was stirred at 120° C. for 16 hours. The mixture was diluted with $H_2O$ (2 mL) and extracted with EtOAc (3 mL×3), and combined organic layers were dried over $MgSO_4$ and concentrated in vacuo. The residue was purified by preparative HPLC (Column: YMC-Actus Triart C18 150*30 mm*7 um; mobile phase: [water (0.225% FA)-ACN]; B %: 35%-55%, 10 min) to give the titled compound (3.6 mg, yield: 16%) as a yellow solid. LC-MS (ESI): m/z 415.1 [M+H]$^+$; $^1$H NMR (400 MHz, DMSO-$d_6$) δ 8.37 (br s, 3H), 8.02-7.79 (m, 1H), 7.79-7.59 (m, 2H), 7.28 (br s, 1H), 6.43-5.93 (m, 2H), 3.93 (br s, 3H), 3.75 (br s, 1H), 2.21-1.86 (m, 6H).

Example 21

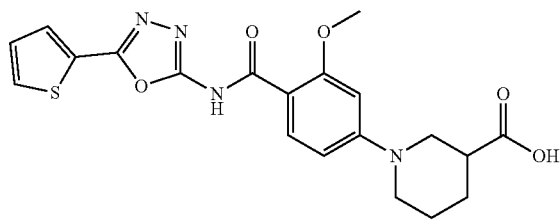

1-(3-methoxy-4-((5-(thiophen-2-yl)-1,3,4-oxadiazol-2-yl)carbamoyl)phenyl)piperidine-3-carboxylic Acid To a solution of 4-bromo-2-methoxy-N-(5-(thiophen-2-yl)-1,3,4-oxadiazol-2-yl)benzamide (80 mg, 0.21 mmol), methyl piperidine-3-carboxylate (45 mg, 0.32 mmol) and $Cs_2CO_3$ (206 mg, 0.63 mmol) in t-Amyl alcohol (2.5 mL) was added RuPhos-Pd-G3 (176 mg, 0.21 mmol) at 25° C. under $N_2$. The mixture was stirred at 120° C. for 16 hours. The solvent was removed in vacuo and the residue was purified by preparative HPLC (Column: Phenomenex Gemini-NX 150*30 mm*5 um; mobile phase: [water (water (0.225% FA)-ACN]; B %: 26%-66%, 10 min) to give the titled compound (6 mg, yield: 6%) as a gray solid. LC-MS (ESI): m/z 429.0 [M+H]$^+$; $^1$H NMR (DMSO-$d_6$, 400 MHz); δ 7.94 (d, J=5.0 Hz, 1H), 7.68-7.82 (m, 2H), 7.30 (t, J=4.3 Hz, 1H), 6.65 (br d, J=8.5 Hz, 1H), 6.56 (s, 1H), 3.96 (s, 3H), 3.91 (br d, J=12.4 Hz, 1H), 3.75 (br d, J=14.0 Hz, 1H), 3.00-3.24 (m, 3H), 1.94 (br s, 1H), 1.49-1.78 ppm (m, 3H).

Example 22

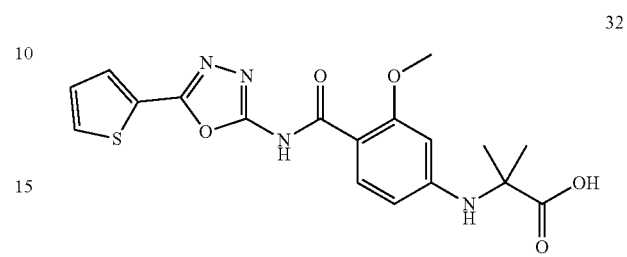

2-((3-methoxy-4-((5-(thiophen-2-yl)-1,3,4-oxadiazol-2-yl)carbamoyl)phenyl)amino)-2-methylpropanoic Acid To a suspension of 4-bromo-2-methoxy-N-(5-(thiophen-2-yl)-1,3,4-oxadiazol-2-yl)benzamide (80 mg, 0.210 mmol) and 2-amino-2-methylpropanoic acid (0.04 mL, 0.421 mmol) in DMSO (2 mL) was added CuI (1.00 mg, 0.021 mmol), pyrrolidine-2-carboxylic acid (1.2 mg, 0.042 mmol) and $Cs_2CO_3$ (137.11 mg, 0.421 mmol) under $N_2$, and stirred at 110° C. for 16 hours. The mixture was a yellow solution. The mixture was filtered and washed with DMSO (1 mL) and the filtrate was purified by preparative HPLC (Column: YMC-Actus Triart C18 150*30 mm*7 um; mobile phase: [water (0.225% FA)-ACN]; B %: 23%-63%, 10 min) to give the titled compound (19 mg, yield: 21%) as a white solid. LC-MS (ESI): m/z 403.1 [M+H]$^+$; $^1$H NMR (400 MHz, DMSO-$d_6$) δ 10.60 (br s, 1H), 7.93 (d, J=5.1 Hz, 1H), 7.77 (d, J=3.8 Hz, 1H), 7.64 (d, J=8.9 Hz, 1H), 7.29 (t, J=4.5 Hz, 1H), 6.28-6.14 (m, 2H), 3.86 (s, 3H), 1.48 (s, 6H).

Example 23

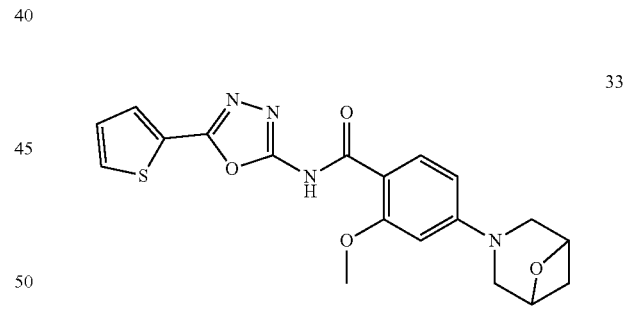

4-(6-oxa-3-azabicyclo[3.1.1]heptan-3-yl)-2-methoxy-N-(5-(thiophen-2-yl)-1,3,4-oxadiazol-2-yl)benzamide To a solution of 4-bromo-2-methoxy-N-(5-(thiophen-2-yl)-1,3,4-oxadiazol-2-yl)benzamide (65 mg, 0.17 mmol), 6-oxa-3-azabicyclo[3.1.1]heptane 4-methylbenzenesulfonate TSOH salt (70 mg, 0.26 mmol), and $Cs_2CO_3$ (392 mg, 1.2 mmol) in t-amyl alcohol (2 mL) was added RuPhos-Pd-G3 (144 mg, 0.17 mmol) at 25° C. under $N_2$. The mixture was stirred at 120° C. for 16 hours. The solvent was removed in vacuo and the residue was purified by preparative HPLC (Column: Xtimate C18 100*30 mm*3 um; mobile phase: [water (0.05% ammonia hydroxide v/v)-ACN; B %: 41%-81%, 10 min) to give the titled compound (17 mg, yield: 24%) as a yellow solid. LC-MS (ESI): m/z 399.0 [M+H]$^+$; $^1$H NMR (DMSO-$d_6$, 400 MHz): δ 7.65 (d, J=5.0 Hz, 1H), 7.52 (d, J=8.3 Hz, 1H), 7.45 (d, J=3.6 Hz, 1H), 7.13-7.20 (m, 1H), 6.12-6.36 (m, 2H), 4.71 (br d, J=6.3 Hz, 2H), 3.73 (s, 3H), 3.57 (br d, J=11.4 Hz, 2H), 3.44 (br, s, 2H), 3.07-3.17 (m, 1H), 2.08 (s, 1H), 1.93 (d, J=8.8 Hz, 1H).

Example 24

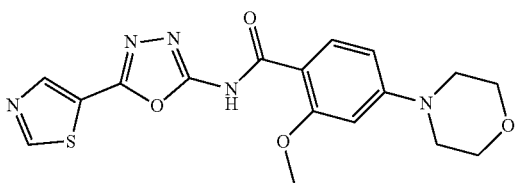

34

2-methoxy-4-morpholino-N-(5-(thiazol-5-yl)-1,3,4-oxadiazol-2-yl)benzamide a) Methyl 2-methoxy-4-morpholinobenzoate To a solution of methyl 4-fluoro-2-methoxybenzoate (10 g, 54 mmol) in morpholine (38 mL, 434 mmol) and NMP (30 mL) at 25° C. under $N_2$. The mixture was stirred at 145° C. for 16 hours. The mixture was freeze drying to remove solvent to give a residue. The residue was purified by flash silica gel chromatography (ISCO®: 120 g SepaFlash® Silica Flash Column, Eluent of 0~30% ethyl acetate/petroleum ether gradient=1:2) to give the titled compound (3.5 g, yield: 18%) as a white solid. LC-MS (ESI): m/z 252.0 [M+H]+.

b) 2-methoxy-4-morpholinobenzoic acid

To a solution of methyl 2-methoxy-4-morpholinobenzoate (3.0 g, 8.5 mmol) in a mixed solvent of THF (40 mL) and $H_2O$ (40 mL) was added LiOH.$H_2O$ (12.59 mg, 0.3 mmol) in one portion at 25° C. The reaction mixture was heated to 40° C. for 16 hours. The solvent was removed and the residue was acidified to pH=2 with 1 N HCl. A solid was formed and collected the solid by filtration. The solid was washed with $H_2O$ (10 mL×3) and dried in vacuum to give the titled compound (1.2 g, yield: 52%) as a white solid. LC-MS (ESI): m/z 238.1 [M+H]+.

c) 2-methoxy-4-morpholino-N-(5-(thiazol-5-yl)-1,3,4-oxadiazol-2-yl)benzamide

To a suspension of 2-methoxy-4-morpholinobenzoic acid (300 mg, 1.3 mmol) and 5-(thiazol-5-yl)-1,3,4-oxadiazol-2-amine (319 mg, 1.9 mmol) in EtOAc (2 mL) was added $T_3P$ (1.50 mL, 5.1 mmol) and TEA (0.70 mL, 5.1 mmol) at 25° C. Heated the reaction mixture at 80° C. for 16 hours. The mixture was diluted with $H_2O$ (10 mL) and extracted with EtOAc (10 mL×3). The combined organic layers were dried over $MgSO_4$, filtered and concentrated under reduced pressure. The residue was titrated with DMSO (4 mL), filtered and washed with $H_2O$ (5 mL×3) to give crude product. The crude was washed with MTBE (5 mL) to give the titled compound (110 mg, yield: 20%) as a yellow solid. LC-MS (ESI): m/z 388.1 [M+H]+; 1H NMR (DMSO-$d_6$, 400 MHz): δ 10.87 (s, 1H), 9.40 (s, 1H), 8.56 (s, 1H), 7.73 (d, J=8.9 Hz, 1H), 6.67 (dd, J=8.8, 1.8 Hz, 1H), 6.59 (s, 1H), 3.96 (s, 3H), 3.69-3.80 (m, 4H), 3.35-3.38 (m, 4H).

Example 25

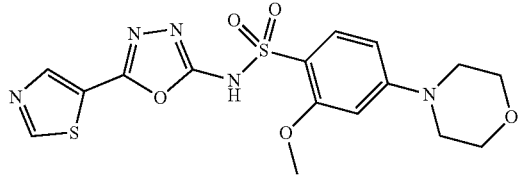

35

2-methoxy-4-morpholino-N-(5-(thiazol-5-yl)-1,3,4-oxadiazol-2-yl)benzenesulfonamide To a suspension of 5-(thiazol-5-yl)-1,3,4-oxadiazol-2-amine (50 mg, 0.3 mmol) in THF (3 mL) was added NaH (36 mg, 0.9 mmol, 60% purity in mineral oil) in one portion at 0° C. and then the reaction mixture was stirred at 0° C. for 15 min. 2,4-dimethoxybenzenesulfonyl chloride (120 mg, 0.5 mmol) was added in one portion and the reaction mixture was stirred at 25° C. for 16 hours. $H_2O$ (1 mL) was added to the reaction mixture at 0° C. to quench the reaction and then the reaction mixture was concentrated under reduced pressure to give a residue. The residue was purified by preparative HPLC (column: Daisogel SP ODS RPS 150*25 mm*5 um; mobile phase: [water (0.225% FA)-ACN]; B %: 18%-58%, 11 min) to give the titled compound (56 mg, yield: 51%) as a white solid. LC-MS (ESI): m/z 369.0 [M+H]+; 1H NMR (DMSO-$d_6$, 400 MHz): δ 9.38 (s, 1H), 8.48 (s, 1H), 7.78 (d, J=8.7 Hz, 1H), 6.60-6.70 (m, 2H), 3.83 (s, 3H), 3.75 (s, 3H).

Example 26

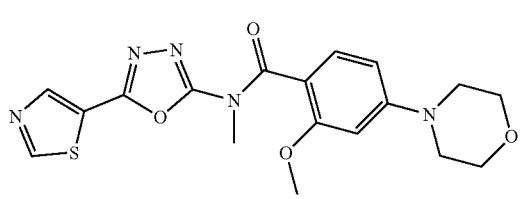

36

2-methoxy-N-methyl-4-morpholino-N-(5-(thiazol-5-yl)-1,3,4-oxadiazol-2-yl)benzamide a) 2,4-dimethoxy-N-(5-(thiazol-5-yl)-1,3,4-oxadiazol-2-yl)benzamide To a suspension of 5-(thiazol-5-yl)-1,3,4-oxadiazol-2-amine (100 mg, 0.60 mmol) in EtOAc (0.6 mL) was added 2,4-dimethoxybenzoic acid (162.48 mg, 0.90 mmol) and TEA (0.33 mL, 2.38 mmol) in one portion at 25° C. and stirred for 10 mins, then $T_3P$ (1.51 g, 2.38 mmol, 1.41 mL, 50% purity) was added, then the reaction mixture was heated to 80° C. and stirred at 80° C. for 16 hours, the reaction mixture was a brown solution. The reaction mixture was cooled to 25° C., water (2 mL) was added to the reaction mixture and was extracted with EtOAc (1 mL×2). The combined organic layers were separated, dried with $Na_2SO_4$, filtered, was concentrated under reduced pressure. The residue was purified by preparative HPLC (column: Daisogel SP ODS RPS 150*25 mm*5 um; mobile phase: [water (0.225% FA)-ACN]; B %: 28%-68%, 30 min) to give the titled compound (0.1 g, yield: 51%) as a white solid. LC-MS (ESI): m/z 333.1 [M+H]$^+$.

b) 2,4-dimethoxy-N-methyl-N-(5-(thiazol-5-yl)-1,3,4-oxadiazol-2-yl)benzamide

To a solution of 2,4-dimethoxy-N-(5-(thiazol-5-yl)-1,3,4-oxadiazol-2-yl)benzamide (10 mg, 0.030 mmol) in DMF (0.3 mL) was add K$_2$CO$_3$ (16.59 mg, 0.120 mmol) in one portion at 25° C. and stirred for 10 mins, then CH$_3$I (3.75 µL, 0.060 mmol) was added, the reaction mixture was heated to 55° C. and stirred at 55° C. for 30 minutes. The reaction mixture was filtered and the filtrate was purified by preparative HPLC (column: YMC-Triart Prep C18 150*40 mm*7 um; mobile phase: [water (0.05% ammonia hydroxide v/v)-ACN; B %: 25%-65%, 11 min) to give the titled compound (1.5 mg, yield: 14%) as a white solid. LC-MS (ESI): m/z 347.1 [M+H]$^+$; $^1$H NMR (CDCl$_3$, 400 MHz) δ 8.92 (s, 1H), 8.03 (s, 1H), 7.56 (d, J=8.4 Hz, 1H), 6.62 (dd, J=8.4, 1.8 Hz, 1H), 6.35 (s, 1H), 3.87 (s, 3H), 3.66 (s, 3H), 3.59 ppm (s, 3H).

Example 27

37

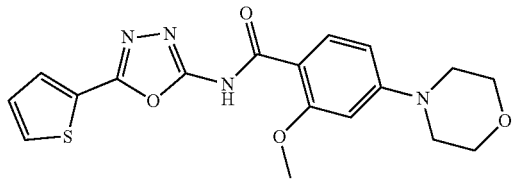

2-methoxy-4-morpholino-N-(5-(thiophen-2-yl)-1,3,4-oxadiazol-2-yl)benzamide

To a suspension of 2-methoxy-4-morpholinobenzoic acid (40 mg, 0.17 mmol) and 5-(thiophen-2-yl)-1,3,4-oxadiazol-2-amine (42 mg, 0.25 mmol) in ethyl acetate (0.4 mL) was added T$_3$P (75 mL, 0.25 mmol) and TEA (35 mL, 0.25 mmol) at 25° C., and the reaction mixture was stirred at 80° C. for 16 hours. The mixture was diluted with H$_2$O (3 mL) and extracted with ethyl acetate (3 mL-3). The combined organic layers were dried over MgSO$_4$, filtered and concentrated under reduced pressure. The residue was purified by preparative HPLC Column: (Phenomenex Gemini-NX 150*30 mm*5 um; mobile phase: [water (0.225% FA)-ACN]; B %: 26%-66%, 10 min) to give the tided compound (17 mg, yield: 25%) as a yellow solid. LC-MS (ESI): m/z 387.0 [M+H]$^+$; $^1$H NMR (DMSO-d$_6$, 400 MHz): δ 10.79 (br s, 1H), 7.92 (br d, J=4.8 Hz, 1H), 7.71-7.82 (m, 2H), 7.29 (t, J=4.3 Hz, 1H), 6.66 (br d, J=8.5 Hz, 1H), 6.57 (s, 1H), 3.95 (s, 3H), 3.73 (br d, J=4.5 Hz, 4H), 3.55-3.57 (m, 4H).

Example 28

38

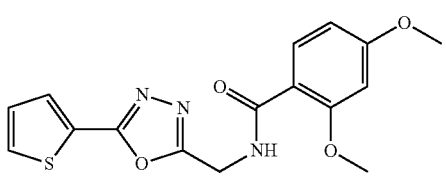

2,4-dimethoxy-N-((5-(thiophen-2-yl)-1,3,4-oxadiazol-2-yl-methyl)benzamide a) tert-butyl (2-oxo-2-(2-(thiophene-2-carbonyl)hydrazino)ethylcarbamate To a suspension of thiophene-2-carboxylic acid (0.50 g, 3.90 mmol) and tert-butyl (2-oxo-2-(2-(thiophene-2-carbonyl)hydrazino)ethyl)carbamate (0.96 g, 5.07 mmol) in DMF (40 mL) was added HATU (1.93 g, 5.07 mmol) and DIEA (1.94 mL, 11.7 mmol) at 25° C., and the reaction mixture was stirred at 25° C. for 16 hours. The mixture was removed solvent in vacuo to give the titled compound (2.7 g, 81%) as yellow oil which was used in the next step without purification. LC-MS (ESI): m/z 244.1 [M+H]$^+$.

b) tert-butyl ((5-(thiophen-2-yl)-1,3,4-oxadiazol-2-yl)methyl)carbamate

To a solution of tert-butyl (2-oxo-2-(2-(thiophene-2-carbonyl)hydrazino)ethyl)carbamate (2.7 g, 3.16 mmol) and PPh$_3$ (2.48 g, 9.47 mmol) in acetonitrile (50 mL) was added triethyl amine (1.31 mL, 9.47 mmol), and stirred at 25° C. for 20 min. Carbon tetrachloride (0.92 mL, 9.47 mmol) was added in the mixture and stirred at 25° C. for 16 hours. The solvent was removed in vacuo. The residue was purified by flash silica gel chromatography (ISCO®; 40 g SepaFlash® Silica Flash Column, Eluent of 0~50% Ethyl acetate/Petroleum ether gradient) to give the titled compound (800 mg, 81%) as a light yellow solid. LC-MS (ESI): m/z 282.1 [M+H]$^+$.

c) (5-(thiophen-2-yl)-1,3,4-oxadiazol-2-yl)methanamine TFA Salt

To a solution of tert-butyl ((5-(thiophen-2-yl)-1,3,4-oxadiazol-2-yl)methyl)carbamate (150 mg, 0.48 mmol) in DCM (1.5 mL) was added dropwise TFA (1.5 mL) at 25° C. The mixture was stirred at 25° C. for 2 hours. The solvent was removed in vacuo under N$_2$ to give the titled compound (130 mg, 0.47 mmol, 94%) as a light yellow solid. LC-MS (ESI): m/z 182.2 [M+H]$^+$.

d) 2,4-dimethoxy-N-((5-(thiophen-2-yl)-1,3,4-oxadiazol-2-yl)methyl)benzamide

To a suspension of (5-(thiophen-2-yl)-1,3,4-oxadiazol-2-yl)methanamine TFA salt (65 mg, 0.25 mmol) and 2,4-dimethoxybenzoic acid (68.61 mg, 0.38 mmol) in EtOAc (2 mL) was added T$_3$P (0.6 mL, 1.0 mmol) and TEA (0.3 mL, 2.0 mmol) at 25° C. The mixture was stirred at 80° C. for 16 hours. The mixture was diluted with H$_2$O (3 ml) and extracted with ethyl acetate (5 mL×3), The combined organic layers were dried over MgSO$_4$, filtered and concentrated in vacuo. The residue was purified by preparative HPLC (Column: Boston Green ODS 150*30 mm*5 um; mobile phase: [water (0.225% FA)-ACN]; B %: 26%-66%, 10 min) to give the titled compound (17.8 mg, 21%) as a white solid. LC-MS (ESI): m/z 346.1 [M+H]$^+$, $^1$H NMR (DMSO-d$_6$, 400 MHz): δ 8.77 (t, J=5.7 Hz, 1H), 7.93 (dd, J=5.0, 1.1 Hz, 1H), 7.85 (d, J=8.6 Hz, 1H), 7.78 (dd, J=3.7, 1.1 Hz, 1H), 7.28 (dd, J=4.9, 3.8 Hz, 1H), 6.58-6.73 (m, 2H), 4.76 (d, J=5.6 Hz, 2H), 3.94 (s, 3H), 3.83 (s, 3H).

The compounds below were synthesized following the procedures described in Example 28.

| No. | Structure | Name | MS: m/z [M + H]+ | 1H NMR (400 MHz, DMSO-d6) |
|---|---|---|---|---|
| 39 | 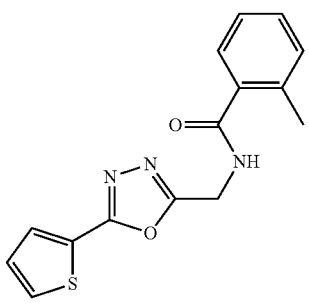 [SMILES: Cc1ccccc1C(=O)NCc1nnc(-c2cccs2)o1] | 2-methyl-N-((5-(thiophen-2-yl)-1,3,4-oxadiazol-2-yl)methyl)benzamide | 300.4 | 1H NMR (400 MHz, CDCl3) δ 9.05 (t, J = 5.6 Hz, 1H), 7.95 (dd, J = 5.0, 1.1 Hz, 1H), 7.79 (dd, J = 3.7, 1.1 Hz, 1H), 7.41-7.34 (m, 2H), 7.31-7.23 (m, 3H), 4.73 (d, J = 5.7 Hz, 2H), 2.37 (s, 3H). |
| 40 | 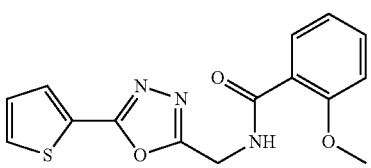 [SMILES: COc1ccccc1C(=O)NCc1nnc(-c2cccs2)o1] | 2-methoxy-N-((5-(thiophen-2-yl)-1,3,4-oxadiazol-2-yl)methyl)benzamide | 316.1 | δ 8.93 (t, J = 5.50 Hz, 1H), 7.93 (dd, J = 1.00, 5.00 Hz, 1H), 7.75-7.85 (m, 2H), 7.45-7.56 (m, 1H), 7.28 (dd, J = 3.75, 5.00 Hz, 1H), 7.18 (d, J = 8.25 Hz, 1H), 7.06 (t, J = 7.50 Hz, 1H), 4.78 (d, J = 5.63 Hz, 2H), 3.92 (s, 3H). |
| 41 | 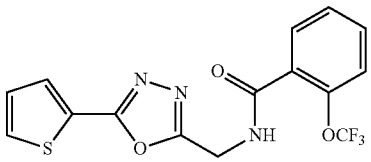 | N-((5-(thiophen-2-yl)-1,3,4-oxadiazol-2-yl)methyl)-2-(trifluoromethoxy)benzamide | 370.1 | δ 9.26 (t, J = 5.62 Hz, 1H), 7.95 (dd, J = 1.22, 5.01 Hz, 1H), 7.77 (dd, J = 1.22, 3.79 Hz, 1H), 7.60-7.67 (m, 2H), 7.44-7.54 (m, 2H), 7.31 (dd, J = 3.79, 5.01 Hz, 1H), 4.75 (d, J = 5.75 Hz, 2H). |
| 42 | 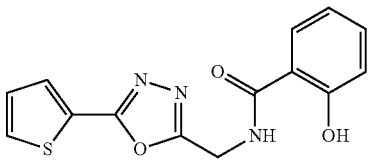 [SMILES: O=C(NCc1nnc(-c2cccs2)o1)c1ccccc1O] | 2-hydroxy-N-((5-(thiophen-2-yl)-1,3,4-oxadiazol-2-yl)methyl)benzamide | 302.1 | δ 12.01 (br s, 1H), 9.47 (br t, J = 5.25 Hz, 1H), 7.84-8.00 (m, 2H), 7.79 (dd, J = 1.06, 3.69 Hz, 1H), 7.39-7.50 (m, 1H), 7.28 (dd, J = 3.75, 4.88 Hz, 1H), 6.87-7.00 (m, 2H), 4.82 (d, J = 5.38 Hz, 2H). |
| 43 | 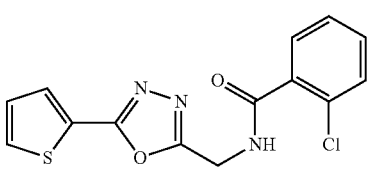 [SMILES: O=C(NCc1nnc(-c2cccs2)o1)c1ccccc1Cl] | 2-chloro-N-((5-(thiophen-2-yl)-1,3,4-oxadiazol-2-yl)methyl)benzamide | 320.0 | 1H NMR (400 MHz, CDCl3) δ 7.80-7.74 (m, 2H), 7.60-7.56 (m, 1H), 7.42 (dd, J = 8.1, 1.4 Hz, 3H), 7.38 (d, J = 7.5 Hz, 1H), 7.18 (dd, J = 5.0, 3.8 Hz, 1H), 6.93 (s, 1H), 4.98 (d, J = 5.6 Hz, 2H). |
| 44 | 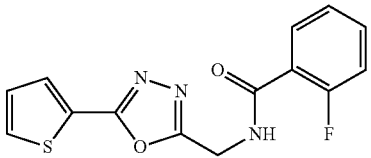 [SMILES: O=C(NCc1nnc(-c2cccs2)o1)c1ccccc1F] | 2-fluoro-N-((5-(thiophen-2-yl)-1,3,4-oxadiazol-2-yl)methyl)benzamide | 304.0 | δ 9.08 (s, 1H), 7.99-7.46 (m, 4H), 7.29 (s, 3H), 4.75 (s, 2H). |
| 45 | 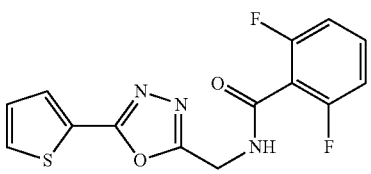 [SMILES: O=C(NCc1nnc(-c2cccs2)o1)c1c(F)cccc1F] | 2,6-difluoro-N-((5-(thiophen-2-yl)-1,3,4-oxadiazol-2-yl)methyl)benzamide | 322.0 | δ 9.55 (s, 1H), 7.96 (d, J = 4.6 Hz, 1H), 7.78 (d, J = 3.0 Hz, 1H), 7.56 (dd, J = 15.1, 7.8 Hz, 1H), 7.33-7.29 (m, 1H), 7.20 (t, J = 8.1 Hz, 2H), 4.78 (d, J = 5.6 Hz, 2H). |

| No. | Structure | Name | MS: m/z [M + H]+ | 1H NMR (400 MHz, DMSO-d6) |
|---|---|---|---|---|
| 46 | 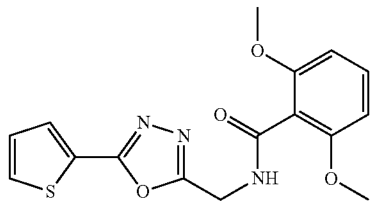 [SMILES: COc1cccc(OC)c1C(=O)NCc1nnc(-c2cccs2)o1] | 2,6-dimethoxy-N-((5-(thiophen-2-yl)-1,3,4-oxadiazol-2-yl)methyl)benzamide | 346.1 | δ 8.82 (t, J = 5.5 Hz, 1H), 7.96 (dd, J = 5.0, 1.1 Hz, 1H), 7.79 (dd, J = 3.7, 1.1 Hz, 1H), 7.26-7.35 (m, 2H), 6.66 (t, J = 9.2 Hz, 2H), 4.65 (d, J = 5.7 Hz, 2H), 3.71 (s, 6H). |
| 47 | 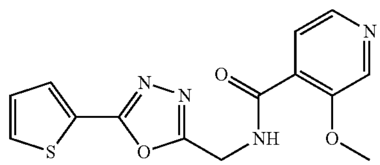 [SMILES: COc1cnccc1C(=O)NCc1nnc(-c2cccs2)o1] | 3-methoxy-N-((5-(thiophen-2-yl)-1,3,4-oxadiazol-2-yl)methyl)isonicotinamide | 317.1 | δ 9.10 (s, 1H), 8.58 (s, 1H), 8.33 (d, J = 4.7 Hz, 1H), 7.95 (d, J = 4.9 Hz, 1H), 7.79 (d, J = 3.4 Hz. 1H), 7.60 (d, J = 4.7 Hz, 1H), 7.32-7.26 (m, 1H), 4.78 (s, 2H), 4.01 (s, 3H). |
| 48 | 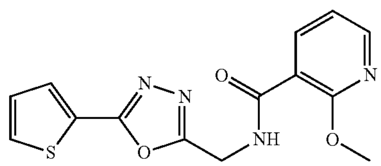 [SMILES: COc1ncccc1C(=O)NCc1nnc(-c2cccs2)o1] | 2-methoxy-N-((5-(thiophen-2-yl)-1,3,4-oxadiazol-2-yl)methyl)nicotinamide | 317.0 | δ 9.04 (s, 1H), 8.35 (d, J = 3.0 Hz, 1H), 8.19 (d, J = 5.8 Hz, 1H), 7.94 (d, J = 4.8 Hz, 1H), 7.79 (d, J = 2.6 Hz, 1H), 7.30-7.26 (m, 1H), 7.16 (dd, J = 7.3, 5.0 Hz, 1H), 4.79 (d, J = 5.6 Hz, 2H), 4.00 (s, 3H). |
| 49 | 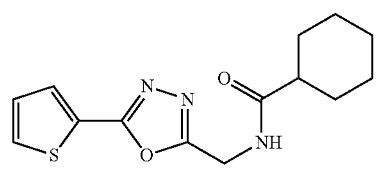 [SMILES: O=C(NCc1nnc(-c2cccs2)o1)C1CCCCC1] | N-((5-(thiophen-2-yl)-1,3,4-oxadiazol-2-yl)methyl)cyclohexane carboxamide | 292.1 | δ 8.50 (s, 1H), 7.94 (d, J = 4.2 Hz, 1H), 7.76 (d, J = 2.8 Hz, 1H), 7.31-7.27 (m, 1H), 4.52 (d, J = 5.6 Hz, 2H), 2.19 (t, J = 11.4 Hz, 1H), 1.71 (s, 4H), 1.40-1.12 (m, 6H). |
| 50 | 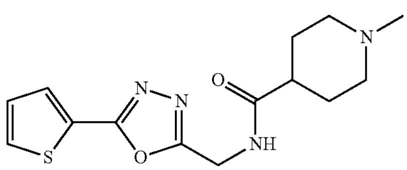 [SMILES: CN1CCC(C(=O)NCc2nnc(-c3cccs3)o2)CC1] | 1-methyl-N-((5-(thiophen-2-yl)-1,3,4-oxadiazol-2-yl)methyl)piperidine-4-carboxamide | 307.2 | δ 8.58 (s, 1H), 7.94 (d, J = 4.9 Hz, 1H), 7.76 (d, J = 2.6 Hz, 1H), 7.32-7.26 (m, 1H), 4.53 (d, J = 5.6 Hz, 2H), 2.75 (d, J = 11.4 Hz, 2H), 2.14 (d, J = 12.0 Hz, 4H), 1.82 (t, J = 10.7 Hz, 2H), 1.70-1.52 (m, 4H). |

Example 29

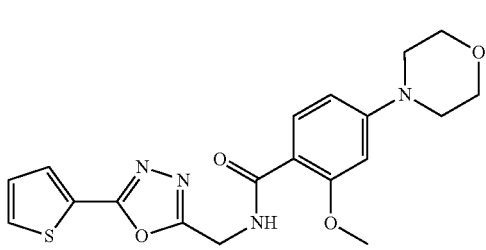

2-methoxy-4-morpholino-N-(5-(thiophen-2-yl)-1,3,4-oxadiazol-2-yl)methyl)benzamide a) (5-(thiophen-2-yl)-1,3,4-oxadiazol-2-yl)methanamine HBF4 Salt To a solution of tert-butyl ((5-(thiophen-2-yl)-1,3,4-oxadiazol-2-yl)methyl)carbamate (50 mg, 0.16 mmol) in TFE (0.5 mL) was added dropwise HBF4 (0.02 mL, 0.16 mmol) at 0° C. The mixture was stirred at 0° C. for 15 min. The mixture dissolved with H2O (2 mL) at 0° C. and freeze drying to give the titled compound (43 mg, yield: 73%) as a light yellow solid. LC-MS (ESI): m/z 182.2 [M+H]+.

b) 2-methoxy-4-morpholino-N-((5-(thiophen-2-yl)-1,3,4-oxadiazol-2-yl)methyl)benzamide To a suspension of 2-methoxy-4-morpholinobenzoic acid (19 mg, 0.083 mmol) and (5-(thiophen-2-yl)-1,3,4-oxadiazol-2-yl)methanamine (45 mg, 0.12 mmol) in ethyl acetate (0.5 mL) was added T3P (0.2 mL, 0.33 mmol) and TEA (0.1 mL, 0.66 mmol) at 25° C., and the reaction mixture was stirred at 80° C. for 16 hours. The mixture was diluted with H2O (2 mL) and extracted with ethyl acetate (3 mL×3). The combined organic layers were dried over MgSO4 and filtered and concentrated in vacuo to give a residue. The residue was purified by preparative HPLC (Column: YMC-Actus Triart C18 150*30 mm*7 um; mobile phase: [water (0.225% FA)-ACN]; B %: 23%-63%, 10 min) to give the titled compound (4.7 mg, yield: 14%) as a white solid. LC-MS (ESI): m/z 401.0 [M+H]+; 1H NMR (DMSO-d6, 400 MHz): δ 8.69 (t, J=5.4 Hz, 1H), 7.94 (dd, J=5.0, 1.0 Hz, 1H), 7.71-7.85 (m, 2H), 7.28 (dd, J=4.9, 3.8 Hz, 1H), 6.47-6.73 (m, 2H), 4.75 (d, J=5.6 Hz, 2H), 3.95 (s, 3H), 3.70-3.81 (m, 4H), 3.22-3.30 ppm (m, 4H).

Example 30

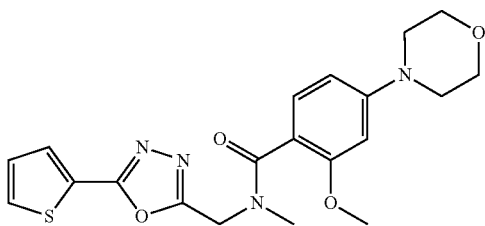

2-methoxy-N-methyl-4-morpholino-N-((5-(thiophen-2-yl)-1,3,4-oxadiazol-2-yl)methyl)benzamide To a solution of 2-methoxy-4-morpholino-N-((5-(thiophen-2-yl)-1,3,4-oxadiazol-2-yl)methyl) benzamide (100 mg, 0.25 mmol) in THF (1.5 mL) was added NaH (60%, 15.0 mg, 0.38 mmol) at 0° C. under $N_2$ and stirred for 0.5 hour. Iodomethane (78 mL, 1.25 mmol) was added to the mixture at 0° C. under $N_2$. The mixture was stirred at 25° C. for 1 hour. The mixture was diluted with $H_2O$ (5 mL) and extracted with EtOAc (5 mL×3). The organic layers were separated, dried over $MgSO_4$, filtered and filtrate was concentrated in vacuo. The residue was purified by preparative HPLC (Column: YMC Triart C18 150×25 mm×5 um; mobile phase: [water (0.225% FA)-ACN]; B %: 35%-55%, 10 min) to give the titled compound (14.1 mg, 13.6%) as a white solid. LC-MS (ESI): m/z 415.2 [M+H]$^+$; $^1$H NMR (400 MHz, DMSO-d$_6$) δ 7.97 (d, J=4.8 Hz, 1H), 7.86-7.73 (m, 1H), 7.35-7.24 (m, 1H), 7.06 (d, J=8.3 Hz, 1H), 6.56 (d, J=11.5 Hz, 2H), 4.94 (s, 1H), 4.64 (s, 1H), 3.81-3.64 (m, 7H), 3.19 (d, J=3.5 Hz, 4H), 3.09-2.86 (m, 3H).

The compound below was synthesized following the procedures described in Example 30.

2-methoxy-3-morpholino-N-((5-(thiophen-2-yl)-1,3,4-oxadiazol-2-yl)methyl)benzamide a) Methyl 2-methoxy-3-morpholinobenzoate A mixture of methyl 3-bromo-2-methoxybenzoate (1.10 g, 4.49 mmol), morpholine (0.79 mL, 8.98 mmol), Pd$_2$(dba)$_3$ (411 mg, 0.45 mmol), Cs$_2$CO$_3$ (4.39 g, 13.5 mmol), BINAP (559 mg, 0.898 mmol) and toluene (30 mL) was degassed with argon for 3 times, and heated to 100° C. for 6 hours. The mixture was mixed with water (100 mL) and was extracted with EA (50 mL×2). The organic layers were combined, washed with brine (50 mL×3), dried over anhydrous Na$_2$SO$_4$ and filtered. The filtrate was concentrated under reduced pressure. The residue was purified using silica gel column chromatography (PE/EA=100/1-4/1) to give the titled compound (303 mg, yield: 26.9%) as a yellow oil. LC-MS (ESI): m/z 252.1 [M+H]$^+$.

b) 2-methoxy-3-morpholinobenzoic Acid

To a solution of methyl 2-methoxy-3-morpholinobenzoate (331 mg, 1.32 mmol) in MeOH (15 mL) and H$_2$O (15 mL) was added LiOH H$_2$O (442 mg, 10.6 mmol), and the resulting mixture was heated to 80° C. for 2 hours. The mixture was concentrated under reduced pressure to remove most of MeOH and the resulting mixture was adjusted to pH 1~2 with aqueous HCl (1.0 M). The resulting suspension was filtered in vacuum. The residue was slurried with (EA/PE=1/10, 44 mL) to afford the title compound (89 mg, yield: 29%) as a white solid. LC-MS (ESI): m/z 238.2 [M+H]$^+$.

c) 2-methoxy-3-morpholino-N-((5-(thiophen-2-yl)-1,3,4-oxadiazol-2-yl)methyl)benzamide To a solution of 2-methoxy-3-morpholinobenzoic acid (52 mg, 0.22 mmol) in DMF (20 mL) were added (5-(thiophen-2-yl)-1,3,4-oxadiazol-2-yl)methanamine (20 mg, 0.11 mmol), DIEA (0.06 mL, 0.39 mmol) and HATU (44 mg, 0.12 mmol). The reaction mixture was stirred at room temperature for 30 minutes. The resulting mixture was diluted with water (50 mL) and was extracted with ethyl acetate (50 mL×2). The organic layers were combined, washed with brine (50 mL×3), dried over anhydrous Na$_2$SO$_4$ and filtered. The filtrate was concentrated under reduced pressure. The residue was purified by preparative HPLC (Method: Waters 2767/2545/2489/QDa, Waters Xbridge C18 10 um OBD 19*150 mm, Mobile Phase A: 0.1% NH$_4$HCO$_3$ in water, Mobile Phase B: CH$_3$CN, Flow: 20 mL/min, Column temp: room temperature) to give the titled compound (15 mg, yield: 34%) as a white solid. LC-MS (ESI): m/z 401.2 [M+H]$^+$; $^1$H NMR (400 MHz, DMSO-d$_6$) δ 8.98 (t, J=5.4 Hz, 1H), 7.94 (d, J=4.8 Hz, 1H), 7.79 (d,

| No. | Structure | Name | MS: m/z [M + H]$^+$ | $^1$H NMR (400 MHz, DMSO-d$_6$) |
|---|---|---|---|---|
| 53 | 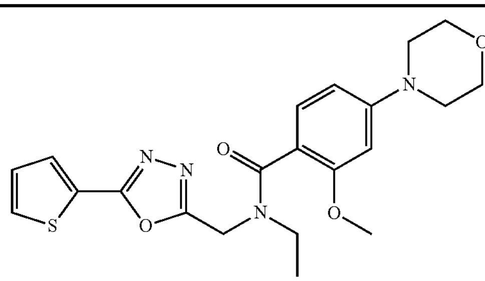 | N-ethyl-2-methoxy-4-morpholino-N-((5-(thiophen-2-yl)-1,3,4-oxadiazol-2-yl)metlayl)benzamide | 429 | δ 7.96 (d, J = 4.6 Hz, 1H), 7.78 (d, J = 16.1 Hz, 1H), 7.31 (s, 1H), 7.02 (d, J = 8.3 Hz, 1H), 6.60-6.49 (m, 2H), 4.91 (s, 1H), 4.63 (s, 1H), 3.79-3.66 (m, 7H), 3.55 (s, 1H), 3.26 (d, J = 6.2 Hz, 1H), 3.18 (s, 4H), 1.16-1.01 (m, 3H). |

Example 31

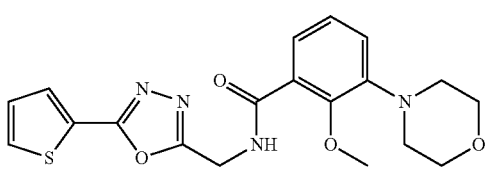

54

J=3.0 Hz, 1H), 7.27-7.32 (m, 1H), 7.25 (d, J=5.8 Hz, 1H), 7.08-7.17 (m, 2H), 4.76 (d, J=5.6 Hz, 2H), 3.86 (s, 3H), 3.77 (s, 4H), 3.00-3.07 (m, 4H).

Example 32

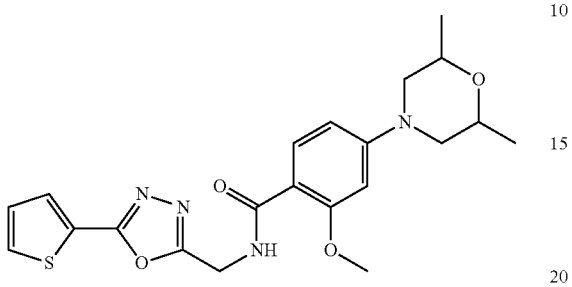

4-(2,6-dimethylmorpholino)-2-methoxy-N-((5-(thiophen-2-yl)-1,3,4-oxadiazol-2-yl)methyl)benzamide
a) Methyl 4-(2,6-dimethylmorpholino)-2-methoxybenzoate A suspension of methyl 4-fluoro-2-methoxybenzoate (500 mg, 2.715 mmol), 2,6-dimethylmorpholine (0.50 mL, 4.07 mmol) and $K_2CO_3$ (563 mg, 4.07 mmol) in DMSO (10 mL) was heated at 120° C. for 16 hours. The resulting mixture was diluted with water (40 mL) and was extracted with EtOAc (20 mL×3). The organic layers were combined, washed with brine (20 mL), dried over anhydrous $Na_2SO_4$, filtered and concentrated under reduced pressure. The residue was purified on silica gel chromatography (PE/EA=20/1-5/1) to give titled compound (115 mg, 15% yield) as a white solid. LC-MS (ESI): m/z 280.1 [M+H]$^+$; $^1$H NMR (400 MHz, DMSO-d$_6$) δ 7.62 (d, J=8.8 Hz, 1H), 6.55 (dd, J=8.9, 2.1 Hz, 1H), 6.51 (s, 1H), 2.42-2.31 (m, 2H), 1.17 (d, J=6.2 Hz, 6H).
b) 4-(2,6-dimethylmorpholino)-2-methoxybenzoic Acid A mixture of methyl 4-(2,6-dimethylmorpholino)-2-methoxybenzoate (115 mg, 0.412 mmol), LiOH.H$_2$O (34.6 mg, 0.823 mmol), THF (5.0 mL) and water (2.5 mL) was heated at 70° C. for 8 hours. The resulting mixture was adjusted to pH 5~6 with diluted HCl (1.0 M) and was extracted with EtOAc (10 mL×3). The organic layers were combined, washed with brine (20 mL), dried over anhydrous Na$_2$SO$_4$ and filtered in vacuum. The filtrate was concentrated under reduced pressure to afford the titled compound (100 mg, yield: 91%) as a light yellow solid. LC-MS (ESI): m/z 266.2 [M+H]$^+$; $^1$H NMR (400 MHz, DMSO-d$_6$) δ 7.69 (d, J=8.7 Hz, 1H), 6.60 (d, J=9.0 Hz, 1H), 6.57 (s, 1H), 3.88 (s, 3H), 3.83 (d, J=12.1 Hz, 3H), 3.71 (d, J=6.7 Hz, 3H), 2.42 (t, J=11.3 Hz, 2H), 1.23 (d, J=6.1 Hz, 5H).
c) 4-(2,6-dimethylmorpholino)-2-methoxy-N-((5-(thiophen-2-yl)-1,3,4-oxadiazol-2-yl)methyl)benzamide A mixture of 4-(2,6-dimethylmorpholino)-2-methoxybenzoic acid (100 mg, 0.377 mmol), DIEA (72.9 mg, 0.565 mmol) and HATU (172 mg, 0.452 mmol) in DMF (3.0 mL) was stirred at room temperature for 30 minutes before (5-(thiophen-2-yl)-1,3,4-oxadiazol-2-yl)methanamine TFA salt (68.3 mg, 0.377 mmol) was added. The resulting reaction mixture was stirred at room temperature for 1 hour. The resulting mixture was diluted with water (15 mL) and was extracted with EA (30 mL-3). The organic layers were combined, washed with brine (30 mL), dried over anhydrous Na$_2$SO$_4$ and filtered. The filtrate was concentrated under reduced pressure. The residue was purified on silica gel chromatography (PE/EA=10/1 to 1/1) to afford the titled compound (138 mg, yield: 85% yield) as a white solid. LC-MS (ESI): m/z 429.2 [M+H]$^+$; $^1$H NMR (400 MHz, DMSO-d$_6$) δ 8.66 (d, J=5.5 Hz, 1H), 7.93 (d, J=4.9 Hz, 1H), 7.76 (d, J=8.7 Hz, 2H), 7.31-7.25 (m, 1H), 6.61 (d, J=8.9 Hz, 1H), 6.56 (s, 1H), 4.75 (d, J=5.5 Hz, 2H), 3.95 (s, 3H), 3.78 (d, J=11.9 Hz, 2H), 3.66 (s, 2H), 2.36 (t, J=11.3 Hz, 2H), 1.17 (d, J=6.1 Hz, 6H).

Example 33

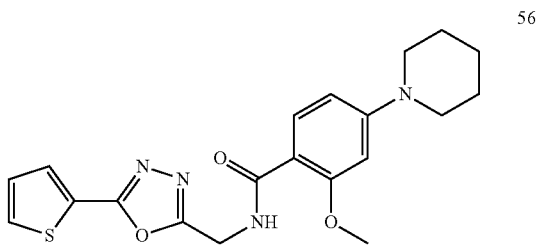 [SMILES: COc1cc(N2CCCCC2)ccc1C(=O)NCc1nnc(-c2cccs2)o1]

2-methoxy-4-(piperidin-1-yl)-N-((5-(thiophen-2-yl)-1,3,4-oxadiazol-2-yl)methyl)benzamide a) 4-bromo-2-methoxy-N-((5-(thiophen-2-yl)-1,3,4-oxadiazol-2-yl)methyl)benzamide To a suspension of 4-bromo-2-methoxybenzoic acid (92.0 mg, 0.40 mmol) and (5-(thiophen-2-yl)-1,3,4-oxadiazol-2-yl)methanamine (100 mg, 0.331 mmol) in pyridine (2 mL) was added EDC HCl (95.2 mg, 0.50 mmol) and DMAP (4.0 mg, 0.033 mmol) at 25° C., and the reaction mixture was stirred at 50° C. for 2 hours. The mixture was concentrated in vacuo. The residue was slurried with acetonitrile (3 mL) and H$_2$O (0.5 mL) to give the titled compound (80 mg, 0.18 mmol, 55.4%) as a white solid. LC-MS (ESI): m/z 394.0 [M+H]$^+$.

b) 2-methoxy-4-(piperidin-1-yl)-N-((5-(thiophen-2-yl)-1,3,4-oxadiazol-2-yl)methyl)benzamide To a solution of 4-bromo-2-methoxy-N-((5-(thiophen-2-yl)-1,3,4-oxadiazol-2-yl)methyl) benzamide (50 mg, 0.12 mmol), piperidine (10 mL, 0.1 mmol), Cs$_2$CO$_3$ (65.4 mg, 0.20 mmol) in t-AmylOH (5 mL) was added RuPhos-Pd-G3 (42.0 mg, 0.05 mmol) at 25° C. under N$_2$. The mixture was stirred at 120° C. for 16 hours. The mixture was diluted with H$_2$O (5 mL) and extracted by EtOAc (5 mL×3). The organic layers were separated, dried over MgSO$_4$, filtered and filtrate was concentrated in vacuo. The residue was purified by preparative mHPLC (Column: YMC Triart C18 150×25 mm×5 um; mobile phase: [water (0.05% ammonia hydroxide v/v)-ACN]; B %: 43%-63%, 10 min) to give the titled compound (9 mg, 21%) as a white solid. LC-MS (ESI): m/z 399.2 [M+H]$^+$; $^1$H NMR (400 MHz, DMSO-d$_6$) δ 7.93 (d, J=5.0 Hz, 1H), 7.81-7.70 (m, 2H), 7.32-7.22 (m, 1H), 6.93 (s, 1H), 6.61-6.46 (m, 2H), 4.75 (s, 2H), 3.94 (s, 3H), 3.30 (s, 4H), 1.59 (s, 6H).

The compounds below were synthesized following the procedures described in Example 33.

| No. | Structure | Name | MS: m/z [M + H]+ | 1H NMR (400 MHz, DMSO-d6) |
|---|---|---|---|---|
| 57 | 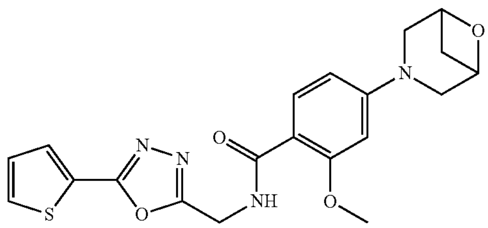 [SMILES: COc1cc(N2CC3CC(C2)O3)ccc1C(=O)NCc1nnc(-c2cccs2)o1] | 4-(6-oxa-3-azabicyclo[3.1.1]heptan-3-yl)-2-methoxy-N-((5-(thiophen-2-yl)-1,3,4-oxadiazol-7-yl)methyl)benzamide | 413.2 | δ 8.64 (t, J = 5.5 Hz, 1H) 7.99-7.89 (m, 1H), 7.85-7.75 (m, 2H), 7.28 (dd, J = 3.8, 5.0 Hz, 1H), 6.49-6.27 (m, 2H), 4.75 (dd, J = 6.1, 11.7 Hz, 4H), 3.98 (s, 3H), 3.68-3.58 (m, 2H), 3.56-3.48 (m, 2H), 3.20-3.10 (m, 1H) 1.90 (d, J = 8.6 Hz, 1H). |
| 58 | 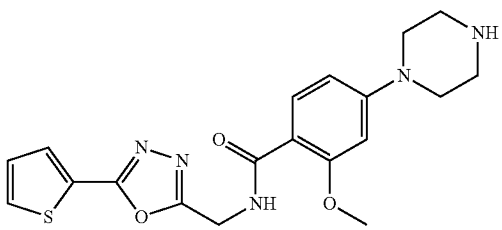 [SMILES: COc1cc(N2CCNCC2)ccc1C(=O)NCc1nnc(-c2cccs2)o1] | 2-methoxy-4-(piperazin-1-yl)-N-((5-(thiophen-2-yl)-1,3,4-oxadiazol-2-yl)methyl)benzamide | 400.2 | δ 8.65 (d, J = 5.4 Hz, 1H), 7.93 (d, J = 4.8 Hz, 1H), 7.76 (t, J = 6.3 Hz, 2H), 7.30-7.25 (m, 1H), 6.57 (d, J = 8.6 Hz, 1H), 6.52 (s, 1H), 4.74 (d, J = 5.5 Hz, 2H), 3.93 (s, 3H), 3.21 (s, 4H), 2.82 (s, 4H). |
| 59 | 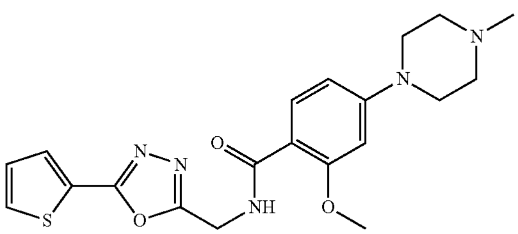 [SMILES: COc1cc(N2CCN(C)CC2)ccc1C(=O)NCc1nnc(-c2cccs2)o1] | 2-methoxy-4-(4-methylpiperazin-1-yl)-N-((5-(thiophen-2-yl)-1,3,4-oxadiazol-2-yl)methyl)benzamide | 414.2 | δ 8.67 (t, J = 5.4 Hz, 1H), 7.93 (d, J = 4.9 Hz, 1H), 7.75 (d, J = 8.7 Hz, 2H), 7.31-7.25 (m, 1H), 6.63-6.53 (m, 2H), 4.74 (d, J = 5.5 Hz, 2H), 3.94 (s, 3H), 3.30 (s, 4H), 2.44 (s, 4H), 2.23 (s, 3H). |

Example 34

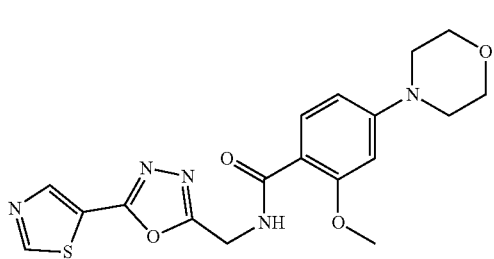

2-methoxy-4-morpholino-N-((5-(thiazol-5-yl)-1,3,4-oxadiazol-2-yl)methyl)benzamide a) tert-butyl (2-oxo-2-(2-(thiazole-5-carbonyl)hydrazino)ethyl)carbamate To a suspension of thiazole-5-carbohydrazide (0.2 g, 1.4 mmol) in THF (5.6 mL) and DMF (1.4 mL) was added HOBt (0.09 g, 0.698 mmol), EDC (0.35 g, 1.816 mmol) and (tert-butoxycarbonyl)glycine (0.88 g, 4.396 mmol) at 25° C., and stirred for 16 hours. The mixture was diluted with 1 N NaOH (18 mL) and extracted with DCM (15 mL×3). The aqueous layer was vacuum freeze dehydration to give the titled compound (4 g, 95%) as a yellow solid. LC-MS (ESI): m/z 301.1 [M+H]+.

b) tert-butyl ((5-(thiazol-5-yl)-1,3,4-oxadiazol-2-yl)methyl)carbamate

To a solution of tert-butyl (2-oxo-2-(2-(thiazole-5-carbonyl)hydrazino)ethyl)carbamate (3.3 g, 1.1 mmol) and PPh3 (0.86 g, 3.3 mmol) in acetonitrile (6 mL) was added TEA (0.5 mL, 3.3 mmol). The reaction was stirred at 25° C. for 20 min. CCl4 (0.3 mL, 3.3 mmol) was added in the mixture and stirred at 25° C. for 16 hours. The solvent was removed in vacuo. The residue was diluted with H2O (5 mL) and extracted with ethyl acetate (10 mL×3). The combined layers were dried over MgSO4, filtered and filtrate was concentrated in vacuo. The residue was purified by flash silica gel chromatography (ISCO®; 40 g SepaFlash® Silica Flash Column, Eluent of 0~30% Ethyl acetate/Petroleum ether gradient) to give a titled compound (0.6 g, 97%) as a white solid. LC-MS (ESI): m/z 283.1 [M+H]+.

c) tert-butyl ((5-(((thiazol-5-yl)-1,3,4-oxadiazol-2-yl)methyl)carbamate HBF4 Salt To a solution of tert-butyl ((5-(thiazol-5-yl)-1,3,4-oxadiazol-2-yl)methyl)carbamate (0.6 g, 1.1 mmol) in TFE (6 mL) was added HBF4 (0.14 mL, 1.06 mmol) dropwise at 0° C. The mixture was stirred at 25° C. for 2 hours. The white suspension mixture was dissolved with H2O (5 mL) at 0° C. and freeze drying. The solid was slurry by DCM (1 mL) to give the titled compound (47 mg, 17%) as a yellow solid. LC-MS (ESI): m/z 183.1 [M+H]+.

d) 2-methoxy-4-morpholino-N-((5-(thiazol-5-yl)-1,3,4-oxadiazol-2-yl)methyl)benzamide To a suspension of tert-butyl ((5-(thiazol-5-yl)-1,3,4-oxadiazol-2-yl)methyl)carbamate HBF4 salt (57.12 mg, 0.217 mmol) and 2-methoxy-4-morpholinobenzoic acid (47 mg, 0.181 mmol) in pyridine (1 mL) was added EDC HCl (52 mg, 0.27 mmol) and DMAP (2.21 mg, 0.018 mmol) at 25° C. The reaction mixture was stirred at 50° C. for 2 hours. The mixture was a yellow solution. The mixture was removed solvent in vacuo. The residue was purified by preparative HPLC (Column: YMC Triart C18 150*25 mm*5 mm; mobile phase: [water (0.05% ammonia hydroxide v/v)-ACN]; B %: 25%-45%, 10 min) to give the titled compound (36 mg, 49/6) as a white solid. LC-MS (ESI): m/z 402.1 [M+H]$^+$: $^1$H NMR (400 MHz, DMSO-d$_6$) δ 9.40 (s, 1H), 8.69 (t, J=5.5 Hz, 1H), 8.56 (s, 1H), 7.78 (d, J=8.8 Hz, 1H), 6.69-6.51 (m, 2H), 4.77 (d, J=5.5 Hz, 2H), 3.95 (s, 3H), 3.78-3.70 (m, 4H), 3.29-3.25 (m, 4H).

The compounds below were synthesized following the procedures described in Example 34.

| No. | Structure | Name | MS: m/z [M + H]$^+$ | $^1$H NMR (400 MHz, DMSO-d$_6$) |
|---|---|---|---|---|
| 61 | 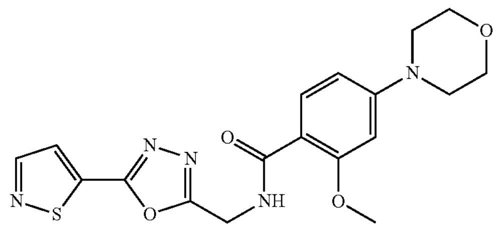 [SMILES: COc1cc(N2CCOCC2)ccc1C(=O)NCc1nnc(-c2ccns2)o1] | N-((5-(isothiazol-5-yl)-1,3,4-oxadiazol-2-yl)methyl)-7-methoxy-4-morpholinobenzamide | 402.1 | δ 8.78 (d, J = 1.8 Hz, 1H), 8.71 (s, 1H), 8.04 (d, J = 1.8 Hz, 1H), 7.77 (d, J = 8.8 Hz, 1H), 6.62-6.58 (m, 1H), 6.57 (d, J = 2.0 Hz, 1H), 4.79 (d, J = 5.6 Hz, 2H), 3.76-3.71 (m, 4H), 3.29-3.24 (m, 4H). |
| 62 | 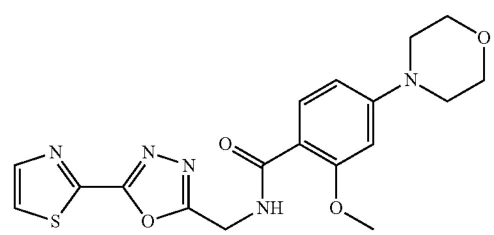 [SMILES: COc1cc(N2CCOCC2)ccc1C(=O)NCc1nnc(-c2nccs2)o1] | 2-methoxy-4-morpholino-N-((5-(thiazol-2-yl)-1,3,4-oxadiazol-2-yl)methyl)benzamide | 402.1 | δ 8.72 (d, J = 5.8 Hz, 1H), 8.15 (s, 2H), 7.78 (d, J = 8.8 Hz, 1H), 6.63-6.55 (m, 2H), 4.80 (d, J = 5.6 Hz, 2H), 3.94 (s, 3H), 3.73 (d, J = 4.5 Hz, 4H), 3.27 (s, 4H). |
| 63 | 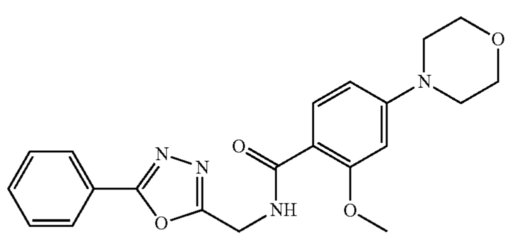 [SMILES: COc1cc(N2CCOCC2)ccc1C(=O)NCc1nnc(-c2ccccc2)o1] | 2-methoxy-4-morpholino-N-((5-phenyl-1,3,4-oxadiazol-2-yl)methyl)benzamide | 395.2 | δ 8.70 (s, 1H), 7.96 (d, J = 6.8 Hz, 2H), 7.78 (d, J = 8.6 Hz, 1H), 7.60 (d, J = 6.8 Hz, 3H), 6.66-6.54 (m, 2H), 4.78 (d, J = 5.1 Hz, 2H), 3.95 (s, 3H), 3.74 (s, 4H), 3.27 (s, 4H). |

Example 35

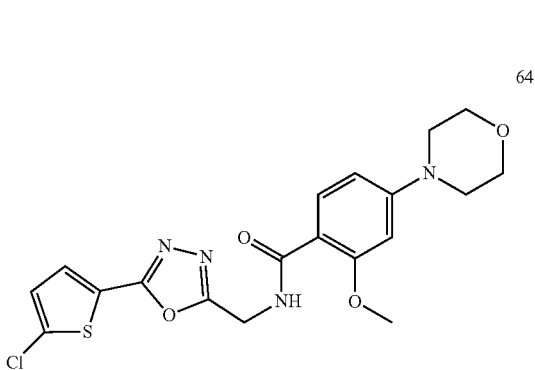 [SMILES: COc1cc(N2CCOCC2)ccc1C(=O)NCc1nnc(-c2ccc(Cl)s2)o1]

N-((5-(5-chlorothiophen-2-yl)-1,3,4-oxadiazol-2-yl)methyl)-2-methoxy-4-morpholinobenzamide a) tert-butyl ((5-(5-chlorothiophen-2-yl)-1,3,4-oxadiazol-2-yl)methyl)carbamate To a mixture of tert-butyl ((5-(thiophen-2-yl)-1,3,4-oxadiazol-2-yl)methyl)carbamate (50 mg, 0.18 mmol) in DMF (0.8 mL) was added NCS (36 mg, 0.3 mmol). The mixture was stirred at 20° C. for 16 hours under $N_2$. The mixture was diluted with 1 M NaOH (3 mL) and extracted with EtOAc (3 mL×3). The combined organic layers were dried over $MgSO_4$, filtered and concentrated to give the titled compound (56 mg, yield: 99%) as yellow oil. LC-MS (ESI): m/z 316.1 [M+H]$^+$.

b) (5-(5-chlorothiophen-2-yl)-1,3,4-oxadiazol-2-yl)methanamine $HBF_4$ Salt

To a solution of tert-butyl ((5-(5-chlorothiophen-2-yl)-1,3,4-oxadiazol-2-yl)methyl)carbamate (87 mg, 0.28 mmol) in TFE (1 mL) was added dropwise $HBF_4$ (37 μL, 0.28 mmol) at 0° C. The mixture was stirred at 25° C. for 2 hours. The mixture was a white suspension. The mixture was dissolved with $H_2O$ (2 mL) at 0° C. and freeze drying to give the titled compound (60 mg, yield: 91%) as a light yellow solid LC-MS (ESI): m/z 216.0 [M+H]$^+$.

c) N-((5-(5-chlorothiophen-2-yl)-1,3,4-oxadiazol-2-yl)methyl)-2-methoxy-4-morpholinobenzamide To a suspension of 2-methoxy-4-morpholinobenzoic acid (79 mg, 0.3 mmol) and (5-(5-chlorothiophen-2-yl)-1,3,4-oxadiazol-2-yl)methanamine (60 mg, 0.3 mmol) in pyridine (1.2 mL) was added EDC-HCl (72 mg, 0.38 mmol) and DMAP (3 mg, 0.03 mmol) at 25° C., and the reaction mixture was stirred at 50° C. for 2 hours. The solvent was removed in vacuo. The residue was slurry in MeCN (3 mL) and DMSO (1 mL). The solid was collected by filtration to give the titled compound (47 mg, yield: 41%) as a white solid. LC-MS (ESI): m/z 435.1 [M+H]$^+$; $^1$H NMR (400 MHz, DMSO-$d_6$) δ 8.68 (t, J=5.6 Hz, 1H), 7.77 (d, J=8.8 Hz, 1H), 7.66 (d, J=4.0 Hz, 1H), 7.34 (d, J=4.0 Hz, 1H), 6.65-6.50 (m, 2H), 4.80-4.65 (m, 2H), 3.94 (s, 3H), 3.77-3.70 (m, 4H), 3.30-3.25 (m, 4H), 1.99 (s, 1H).

Example 36

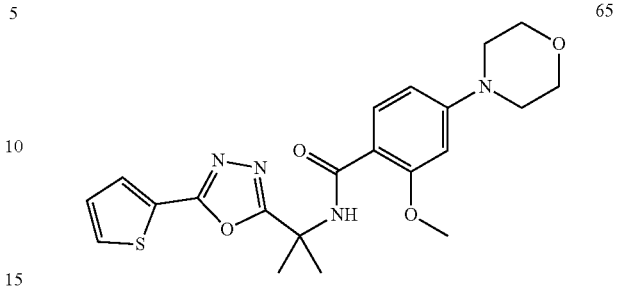

2-methoxy-4-morpholino-N-(2-(5-(thiophen-2-yl)-1,3,4-oxadiazol-2-yl)propan-2-yl)benzamide a) tert-butyl (2-methyl-1-oxo-1-(2-(thiophene-2-carbonyl)hydrazino)propan-2-yl)carbamate To a suspension of thiophene-2-carbohydrazide (0.5 g, 3.5 mmol) in THF (14 mL) and DMF (4 mL) was added HOBt (0.24 g, 1.8 mmol), EDC (0.84 g, 4.4 mmol) and 2-((tert-butoxycarbonyl) amino)-2-methylpropanoic acid (0.88 g, 4.4 mmol) at room temperature. The reaction was stirred for 16 hours. The mixture was diluted with 1 M NaOH (18 mL) and was extracted with DCM (15 mL×3). The combined organic layers was dried over $MgSO_4$, filtered and the solvent was removed in vacuo to give the titled compound (1.1 g, 48%) as a yellow oil. LC-MS (ESI): m/z 328.1 [M+H]$^+$.

b) tert-butyl (2-(5-(thiophen-2-yl)-1,3,4-oxadiazol-2-yl)propan-2-yl)carbamate

To a solution of tert-butyl (2-methyl-1-oxo-1-(2-(thiophene-2-carbonyl)hydrazino) propan-2-yl) carbamate (500 mg, 0.76 mmol) and $PPh_3$ (600 mg, 2.3 mmol) in acetonitrile (5 mL) was added triethyl amine (318 μL, 2.3 mmol). The reaction was stirred at 25° C. for 20 min. $CCl_4$ (221 ILL, 2.3 mmol) was added in the mixture and stirred at 25° C. for 16 hours. The solvent was removed in vacuo and the residue was purified by flash silica gel chromatography (ISCO®; 40 g SepaFlash® Silica Flash Column, Eluent of 0-50% Ethyl acetate/Petroleum ether gradient) to give the titled compound (100 mg, 35%) as a light yellow solid. LC-MS (ESI): m/z 310.0 [M+H]$^+$.

c) 2-(5-(thiophen-2-yl)-1,3,4-oxadiazol-2-yl)propan-2-amine

To a solution of tert-butyl (2-(5-(thiophen-2-yl)-1,3,4-oxadiazol-2-yl)propan-2-yl)carbamate (100 mg, 0.32 mmol) in TFE (1 mL) was added dropwise $HBF_4$ (44 μL, 0.33 mmol) at 0° C. The mixture was stirred at 25° C. for 2 hours. The mixture was dissolved with $H_2O$ (2 mL) and freeze drying to give the titled compound (90 mg, 93%) as a yellow solid. LC-MS (ESI): m/z 210.0 [M+H]$^+$.

d) 2-methoxy-4-morpholino-N-(2-(5-(thiophen-2-yl)-1,3,4-oxadiazol-2-yl)propan-2-yl)benzamide To a suspension of 2-methoxy-4-morpholinobenzoic acid (63 mg, 0.241 mmol) and 2-(5-(thiophen-2-yl)-1,3,4-oxadiazol-2-yl)propan-2-amine (60 mg, 0.20 mmol) in pyridine (1.2 mL), was added EDC HCl (58 mg, 0.30 mmol) and DMAP (2.5 mg, 0.02 mmol) at room temperature. The reaction mixture was stirred at 50° C. for 2 hours. The solvent was removed in vacuo. The residue was slurry in acetonitrile (3 mL) and DMSO (1 mL) to collect the solid by filtration to give the titled compound (18 mg, yield: 20/6) as a white solid. LC-MS (ESI): m/z 429.2 [M+H]$^+$; $^1$H NMR (400 MHz, DMSO-$d_6$) δ 8.39 (s, 1H), 7.91 (dd, J=1.1, 5.0 Hz, 1H), 7.72 (dd, J=1.1, 3.6 Hz, 1H), 7.63 (d, J=9.4 Hz, 1H), 7.25 (dd, J=3.8, 4.9 Hz, 1H), 6.62-6.55 (m, 2H), 3.99 (s, 3H), 3.77-3.71 (m, 4H), 3.28-3.24 (m, 4H), 1.76 (s, 6H).

The compounds below were synthesized following the procedures described in Example 36.

| No. | Structure | Name | MS: m/z [M + H]+ | $^1$H NMR (400 MHz, DMSO-d$_6$) |
|---|---|---|---|---|
| 66 | 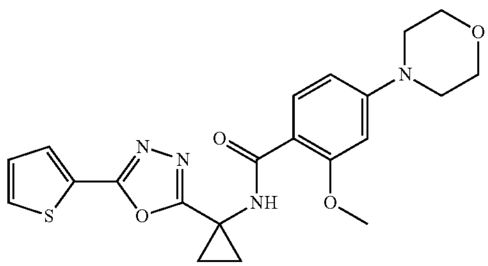 [SMILES: COc1cc(N2CCOCC2)ccc1C(=O)NC1(c2nnc(-c3cccs3)o2)CC1] | 2-methoxy-4-morpholino-N-(1-(5-(thiophen-2-yl)-1,3,4-oxadiazol-2-yl)cyclopropyl)benzamide | 427.2 | δ 8.71 (s, 1H), 7.91 (d, J = 5.0 Hz, 1H), 7.77-7.65 (m, 2H), 7.36-7.17 (m, 1H), 6.67-6.47 (m, 2H), 3.95 (s, 3H), 3.79-3.70 (m, 4H), 3.29-3.25 (m, 4H), 1.68-1.60 (m, 2H), 1.50-1.42 (m, 2H). |
| 67 | 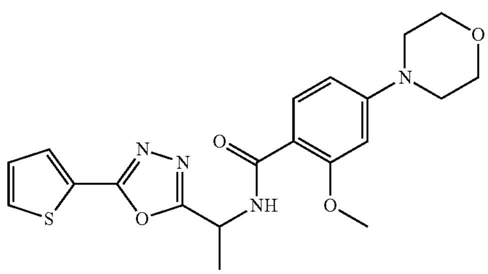 [SMILES: COc1cc(N2CCOCC2)ccc1C(=O)NC(C)c1nnc(-c2cccs2)o1] | 2-methoxy-4-morpholino-N-(1-(5-(thiophen-2-yl)-1,3,4-oxadiazol-2-yl)ethyl)benzamide | 415.4 | δ 8.53 (d, J = 7.3 Hz, 1H), 7.93 (d, J = 5.0 Hz, 1H), 7.75 (dd, J = 15.4, 5.8 Hz, 2H) 7.30-7.25 (m, 1H), 6.63-6.55 (m, 2H), 5.44-5.37 (m, 1H), 3.93 (s, 3H), 3.74 (s, 4H), 3.26 (s, 4H), 1.64 (d, J = 6.9 Hz, 3H). |

Example 37

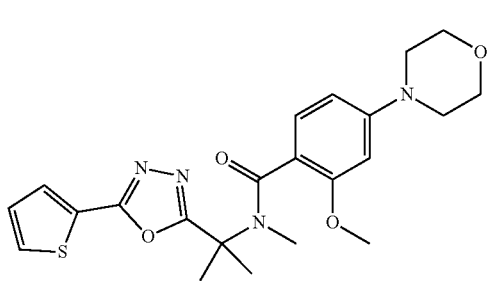

68

2-methoxy-N-methyl-4-morpholino-N-(2-(5-(thiophen-2-yl)-1,3,4-oxadiazol-2-yl)propan-2-yl)benzamide To a solution of 2-methoxy-4-morpholino-N-(2-(5-(thiophen-2-yl)-1,3,4-oxadiazol-2-yl) propan-2-yl)benzamide (400 mg, 0.14 mmol) in THF (1 mL) was added NaH (60% in mineral oil, 8.40 mg, 0.21 mmol) at 0° C. under N$_2$ and stirred for 0.5 hour. Iodomethane (44 μL, 0.7 mmol) was added in the mixture at 0° C. under N$_2$. The mixture was stirred at 25° C. for 1 hr. The mixture was diluted with H$_2$O (1 mL) and extracted with ethyl acetate (1 mL×3). The combined organic layers were dried over MgSO$_4$, filtered and was concentrated in vacuo. The residue purified by preparative HPLC (Column: YMC Triart C18 150*25 mm*5 mm; mobile phase: [water (0.225% FA)-ACN]; B %: 35%-55%, 10 min) to give the titled compound (4.74 mg, 6.6%) as a white solid. LC-MS (ESI): m/z 443.2 [M+H]+; $^1$H NMR (400 MHz, DMSO-d$_6$) δ 8.43 (br s, 1H), 7.92 (dd, J=1.2, 5.1 Hz, 1H), 7.73 (dd, J=1.2, 3.7 Hz, 1H), 7.29 (dd, J=3.7, 5.0 Hz, 1H), 6.97 (d, J=8.4 Hz, 1H), 6.64-6.44 (m, 2H), 3.83 (s, 3H), 3.77-3.68 (m, 4H), 3.26-3.11 (m, 4H), 2.92 (s, 3H), 1.72 (s, 6H).

Example 38

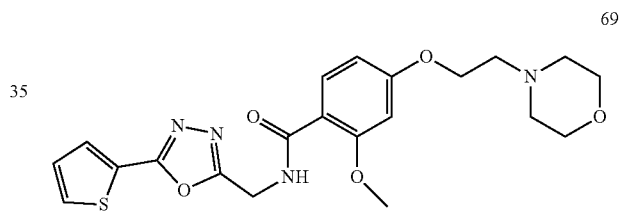

69

2-methoxy-4-(2-morpholinoethoxy)-N-((5-(thiophen-2-yl)-1,3,4-oxadiazol-2-yl)methyl)benzamide a) 4-hydroxy-2-methoxybenzoic Acid To a solution of 4-hydroxy-2-methoxybenzaldehyde (4.9 g, 32.2 mmol) in DMSO (100 mL) and water (75 mL) were added NaH$_2$PO$_4$ (394 mg, 161.025 mmol), NaClO$_2$ (11.7 g, 129 mmol) at 0° C. Then the reaction mixture was stirred at room temperature for 3 hours. The mixture was mixed with water (400 mL), then adjusted to pH 8~0.9 with NaHCO$_3$ powder. The whole was washed with EA (300 mL). The water phase was adjusted to 3-4 with aqueous HCl solution (1.0 M) and the resulting mixture was extracted with ethyl acetate (100 mL×3). The combined organic layers were washed with brine (200 mL), dried over anhydrous Na$_2$SO$_4$ and filtered. The filtrate was concentrated under reduced pressure to afford the title compound (5.39 g, yield: 97.1%) as a yellow oil. LC-MS (ESI): m/z 168.8 [M+H]+.

b) 4-hydroxy-2-methoxy-N-((5-(thiophen-2-yl)-1,3,4-oxadiazol-2-yl)methyl)benzamide To a solution of 4-hydroxy-2-methoxybenzoic acid (1.00 g, 5.95 mmol) in DMF (20 mL) were added BOP (3.95 g, 8.92 mmol), DIEA (3.94 mL, 23.8 mmol), and (5-(thiophen-2-yl)-1,3,4-oxadiazol-2-yl)methanamine (1.82 g, 6.54 mmol), and the reaction was stirred at room temperature for 1.5 hours. The reaction mixture was diluted with water (20 mL). The mixture was extracted with ethyl acetate (20 mL×2). The organic phases were combined, washed with brine (30 mL×2), dried over anhydrous Na$_2$SO$_4$ and filtered. The filtrate was concentrated under reduced pressure to afford the titled compound (1.8 g, yield: 63.9% yield) as a yellow solid. LC-MS (ESI): m/z 332.0 [M+H]$^+$.

c) 2-methoxy-4-(2-morpholinoethoxy)-N-((5-(thiophen-2-yl)-1,3,4-oxadiazol-2-yl)methyl)benzamide To a solution of 4-hydroxy-2-methoxy-N-((5-(thiophen-2-yl)-1,3,4-oxadiazol-2-yl)methyl)benzamide (200 mg, 0.42 mmol) in acetonitrile (3.0 mL) were added 4-(2-chloroethyl)morpholine hydrochloride (70.8 mg, 0.381 mmol), K$_2$CO$_3$ (175 mg, 1.27 mmol), and KI (7.0 mg, 0.042 mmol). And the resulting mixture was heated to 90° C. for 2 hr. The reaction mixture was purified by preparative HPLC (Method: Waters 2767/2545/2489, Inertsil ODS-3 10 um 20*250 nm, Mobile Phase A: 0.1% FA in water, Mobile Phase B: CH$_3$CN, Flow: 20 mL/min, Column temp: RT) to afford the title compound (13 mg, yield: 6.3%) as a white solid. LC-MS (ESI): m/z 445.1 [M+H]$^+$; $^1$H NMR (400 MHz, DMSO-d$_6$) δ 8.76 (t, J=5.5 Hz, 1H), 7.93 (d, J=4.3 Hz, 1H), 7.83 (d, J=8.6 Hz, 1H), 7.77 (d, J=2.8 Hz, 1H), 7.26-7.30 (m, 1H), 6.63-6.70 (m, 2H), 4.75 (d, J=5.5 Hz, 2H), 4.17 (t, J=5.6 Hz, 2H), 3.94 (s, 3H), 3.55-3.61 (m, 4H), 2.70 (t, J=5.6 Hz, 2H), 2.45-2.49 (m, 4H).

The compounds below were synthesized following the procedures described in Example 38.

| No. | Structure | Name | MS: m/z [M + H]$^+$ | $^1$H NMR (400 MHz, DMSO-d$_6$) |
|---|---|---|---|---|
| 70 | 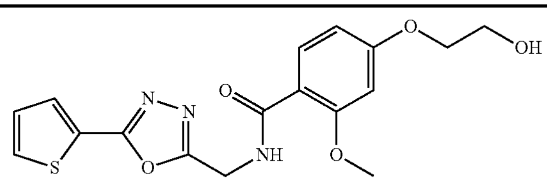 | 4-(2-hydroxyethoxy)-2-methoxy-N-((5-(thiophen-2-yl)-1,3,4-oxadiazol-2-yl)methyl)benzamide | 376.1 | δ 8.76 (s, 1H), 7.93 (d, J = 4.5 Hz, 1H), 7.87-7.73 (m, 2H), 7.28 (s, 1H), 6.72-6.54 (m, 2H), 4.91 (s, 1H), 4.76 (d, J = 5.3 Hz, 2H), 4.07 (s, 2H), 3.93 (s, 3H), 3.73 (s, 2H). |
| 71 | 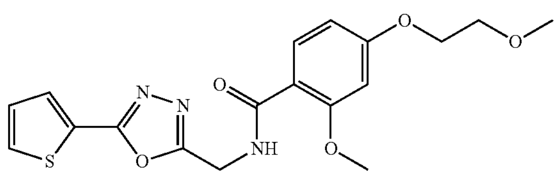 | 2-methoxy-4-(2-methoxyethoxy)-N-((5-(thiophen-2-yl)-1,3,4-oxadiazol-2-yl)methyl)benzamide | 390.0 | δ 8.76 (t, J = 5.4 Hz, 1H), 7.93 (d, J = 4.1 Hz, 1H), 7.83 (d, J = 8.7 Hz, 1H), 7.77 (d, J = 2.7 Hz, 1H), 7.33-7.22 (m, 1H), 6.75-6.59 (m, 2H), 4.76 (d, J = 5.5 Hz, 2H), 4.24-4.12 (m, 2H), 3.93 (s, 3H), 3.75-3.61 (m, 2H), 3.32 (d, J = 5.0 Hz, 3H). |

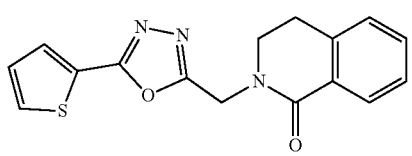

Example 39

2-((5-thiophen-2-yl)-1,3,4-oxadiazol-2-yl)methyl)-3,4-dihydroisoquinolin-1(2H)-one a) N'-(2-chloroacetyl)thiophene-2-carbohydrazide To a mixture of thiophene-2-carbohydrazide (5.00 g, 35 mmol), NaHCO$_3$ (8.86 g, 106 mmol), H$_2$O (40 mL) and THF (60 ml·) was added a solution of 2-chloroacetyl chloride (4.20 mL, 52.8 mmol) in THF (10 mL) dropwise. And the resulting mixture was stirred at room temperature for 1 hour. The reaction mixture was diluted with ethyl acetate (50 mL), washed with brine (10 mL). The organic layer was separated, concentrated under reduced pressure to afford the title compound (2.10 g, yield: 27%). LC-MS (ESI): m/z 219.0 [M+H]$^+$.

b) 2-(chloromethyl)-5-(thiophen-2-yl)-1,3,4-oxadiazole

A mixture of N'-(2-chloroacetyl)thiophene-2-carbohydrazide (1.00 g, 4.57 mmol) and POCl$_3$ (8.50 mL, 91.5 mmol) was heated to 100° C. for 2 hours. Then the reaction mixture was concentrated under reduced pressure. The residue was mixed with DCM (10 mL) and aqueous saturated NaHCO$_3$ (20 mL). The organic layer was separated, dried over anhydrous Na$_2$SO$_4$ and filtered. The filtrate was concentrated under reduced pressure to afford the title compound (700 mg, yield: 76%). LC-MS (ESI): m/z 201.0 [M+H]$^+$.

c) 2-((5-(thiophen-2-yl)-1,3,4-oxadiazol-2-yl)methyl)-3,4-dihydroisoquinolin-1(2H)-one To a solution of 2-(chloromethyl)-5-(thiophen-2-yl)-1,3,4-oxadiazole (250 mg, 1.25 mmol) in DMF (15 mL) was added NaH (74.8 mg, 1.87 mmol, 60% in oil) at 0° C. and the resulting mixture was stirred at this temperature for 30 minutes, 3,4-dihydroisoquinolin-1(2H)-one (250 mg, 1.25 mmol) was added. The reaction mixture was warmed up to RT and stirred for an hour. The resulting mixture was mixed with EA (100 mL) and brine (100 mL). The organic layer was separated, dried over anhydrous Na$_2$SO$_4$ and filtered in vacuum. The filtrate was concentrated under reduced pressure. The residue was purified by preparative HPLC (system: Waters 2767/2545/2489/Qda, Column name: Inertsil ODS-3 10 um 20*250 nm, Mobile Phase A: 0.1% FA in water, Mobile Phase B: CH$_3$CN. Wavelength: 254 nm/214 nm. Flow: 20 mL/min: Column temp: RT) to afford the titled compound (43.1 mg, yield: 11%). LC-MS (ESI): m/z 312.0 [M+H]$^+$; $^1$H NMR (400 MHz, DMSO-d$_6$) δ 7.94 (d, J=4.9 Hz, 1H), 7.77-7.85 (m, 2H), 7.54-7.64 (m, 2H), 7.17-7.36 (m, 1H), 5.02 (s, 2H), 3.75 (t, J=6.5 Hz, 2H), 3.07 (t, J=6.4 Hz, 2H).

Example 40

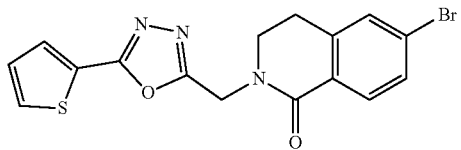

73

6-bromo-2-((5-(thiophen-2-yl)-1,3,4-oxadiazol-2-yl)methyl)-3,4-dihydroisoquinolin-1(2H)-one To a solution of 2-((5-(thiophen-2-yl)-1,3,4-oxadiazol-2-yl)methyl)-3,4-dihydroisoquinolin-1(2H)-one (676 mg, 2.99 mmol) in DMF (15 mL) were added NaH (178 mg, 4.49 mmol, 60% in oil) at 0° C. and the reaction was stirred at 0° C. for 30 min, 6-bromo-3,4-dihydroiso-quinolin-1(2H)-one (600 mg, 3.0 mmol) was added. The resulting mixture was warmed up to room temperature and stirred for an hour. The reaction mixture was diluted with ethyl acetate (20 mL) and brine (20 mL). The organic layer was separated, dried over anhydrous Na$_2$SO$_4$ and filtered. The filtrate was concentrated under reduced pressure to afford the crude (400 mg). The crude product (100 mg) was purified by preparative HPLC (Method: Waters 2767/2545/2489/Qda, Column name: Inertsil ODS-3 10 um 20*250 nm, Mobile Phase A: 0.1% FA in water, Mobile Phase B: CH$_3$CN, Flow: 20 mL/min: Column temp: room temperature) to afford the titled compound (25 mg, yield: 6.5%) as a white solid. LC-MS (ESI): m/z 392.2 [M+H]$^+$; $^1$H NMR (400 MHz, DMSO-d$_6$) δ 7.94 (d, J=4.9 Hz, 1H), 7.77-7.85 (m, 2H), 7.54-7.64 (m, 2H), 7.17-7.36 (m, 1H), 5.02 (s, 2H), 3.75 (t, J=6.5 Hz, 2H), 3.07 (t, J=6.4 Hz, 2H).

Example 41

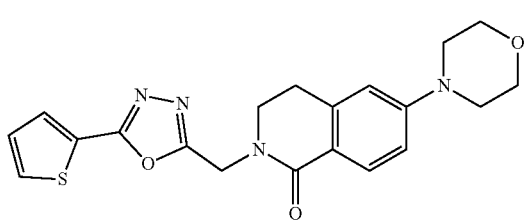

74

6-morpholino-2-((5-(thiophen-2-yl)-1,3,4-oxadiazol-2-yl)methyl)-3,4-dihydroisoquinolin-(2H)-one A mixture of 6-bromo-2-((5-(thiophen-2-yl)-1,3,4-oxadiazol-2-yl)methyl)-3,4-dihydroisoquinolin-1(2H)-one (300 mg, 0.77 mmol), morpholine (0.14 mL, 1.54 mmol), Cs$_2$CO$_3$ (749 mg, 2.30 mmol), BINAP (47.9 mg, 0.08 mmol), Pd$_2$(dba)$_3$ (70.3 mg, 0.080 mmol) and toluene (10 mL) was degassed with argon for 3 times, then heated to 115° C. for 36 hours. The resulting mixture was filtered and the filtrate was concentrated under vacuum. The residue was purified by preparative HPLC (system: Waters 2767/2545/2489/Qda, Waters Xbridge C18 10 um OBD 19*150 mm, Mobile Phase A: 0.1% NH$_4$OH in water, Mobile Phase B: CH$_3$CN, Flow: 20 mL/min: Column temp: room temperature) to afford the title compound (17.0 mg, yield: 5.6%) as a white solid. LC-MS (ESI): m/z 397.1 [M+H]$^+$; $^1$H NMR (400 MHz, DMSO-d$_6$) δ 7.94 (d, J=4.5 Hz, 1H), 7.79 (d, J=2.9 Hz, 1H), 7.73 (d, J=8.8 Hz, 1H), 7.24-7.32 (m, 1H), 6.90 (d, J=7.2 Hz, 1H), 6.80 (s, 1H), 4.97 (s, 1H), 3.61-3.80 (m, 6H), 3.24 (s, 2H), 2.97 (s, 1H).

Example 42

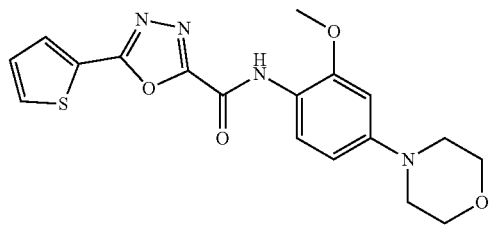

75

N-(2-methoxy-4-morpholinophenyl)-5-(thiophen-2-yl)-1,3,4-oxadiazole-2-carboxamide a) 4-(3-methoxy-4-nitrophenyl)morpholine To a solution of 4-fluoro-2-methoxy-1-nitrobenzene (8.00 g, 47 mmol) in acetonitrile (100 mL) were added morpholine (4.07 g, 467 mmol) and potassium carbonate (7 mg, 51 mmol), and the reaction was stirred at 75° C. for 3 hours. The reaction was concentrated under reduced pressure. The residue was mixed with water (30 mL), the suspension was filtered. The filter cake was collected, washed with water (30 mL), dried in vacuum to afford the titled compound (10.0 g, yield; 90%). LC-MS (ESI): m/z 239.1 [M+H]$^+$.

b) 2-methoxy-4-morpholinoaniline

To a solution of 4-(3-methoxy-4-nitrophenyl)morpholine (3.00 g, 12.6 mmol) in ethyl acetate (30 mL) was added Pd/C (10%, 500 mg), and the reaction mixture was degassed with N$_2$ for 3 times. The reaction mixture was stirred at room temperature under a balloon pressure of H2 for 3 hours. The resulting mixture was filtered and the filtrate was concentrated under reduced pressure to afford the titled compound (2.30 g, yield; 88%). LC-MS (ESI): m/z 209.0 [M+H]$^+$.

c) Methyl 2-oxo-2-(2-(thiophene-2-carbonyl)hydrazino)acetate

To a mixture of thiophene-2-carbohydrazide (3.00 g, 21.1 mmol), NaHCO$_3$ (5.32 g, 63.3 mmol), H$_2$O (15 mL) and THF (15 mL) was added a solution of methyl 2-chloro-2-oxoacetate (3.9 mg, 32 mmol) in THF (2.0 mL) dropwise. The reaction mixture was stirred at rt for 2 hours. The resulting mixture was concentrated under reduced pressure to removed most of THF. The residue was extracted with EA (20 mL×3). The organic layers were combined, washed with brine (20 mL), dried over anhydrous $Na_2SO_4$ and concentrated under reduced pressure to afford the titled compound (5.30 g, 100% yield). LC-MS (ESI): m/z 229.1 $[M+H]^+$.

d) methyl 5-(thiophen-2-yl)-1,3,4-oxadiazole-2-carboxylate

To a solution of methyl 2-oxo-2-(2-(thiophene-2-carbonyl)hydrazino)acetate (1.4 g, 6.13 mmol) in DCM (20 mL), were added TEA (2.56 mL, 18.4 mmol) and tosyl chloride (1.40 g, 7.36 mmol). The resulting mixture was stirred at room temperature for 2 hours. The reaction mixture was concentrated under reduced pressure. The residue was purified using silica gel column chromatography eluting with ethyl acetate in petroleum ether (PE/EA=1/10 to 1/1) to afford the titled compound (650 mg, yield: 50%). LC-MS (ESI): m/z 221.0 $[M+H]^+$.

e) N-(2-methoxy-4-morpholinophenyl)-5-(thiophen-2-yl)-1,3,4-oxadiazole-2-carboxamide To a solution of methyl 5-(thiophen-2-yl)-1,3,4-oxadiazole-2-carboxylate (130 mg, 0.62 mmol) in methanol (5 mL) were added 2-methoxy-4-morpholinoaniline (772 mg, 3.71 mmol) and TEA (0.86 mL, 6.18 mmol), and the reaction was stirred at 65° C. for 5 hours. The reaction mixture was concentrated under reduced pressure. The residue was mixed with ethanol (10 mL) and was filtered in vacuum. The filter cake was dried in vacuum to afford the titled compound (27 mg, yield: 11%). LC-MS (ESI): m/z 387.0 $[M+H]^+$; $^1H$ NMR (400 MHz, DMSO-$d_6$) δ 9.87 (s, 1H), 8.05 (d, J=4.8 Hz, 1H), 7.97 (d, J=2.9 Hz, 1H), 7.66 (d, J=8.7 Hz, 1H), 7.44-7.27 (m, 1H), 6.70 (s, 1H), 6.55 (d, J=8.5 Hz, 1H), 3.87 (s, 3H), 3.75 (s, 4H), 3.15 (s, 4H).

Example 43

76

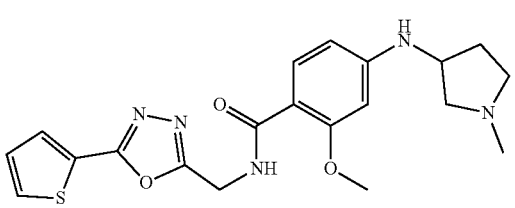

2-methoxy-4-((1-methylpyrrolidin-3-yl)amino)-N-((5-(thiophen-2-yl)-1,3,4-oxadiazol-2-yl)methyl)benzamide a) tert-butyl 3-((3-methoxy-4-(methoxycarbonyl)phenyl)amino)pyrrolidine-1-carboxylate To a solution of methyl 4-bromo-2-methoxybenzoate (5.0 g, 20 mmol) in 1,4-dioxane (50 mL) were added $Pd_2(dba)_3$ (1.87 g, 2.04 mmol), BINAP (1.27 g, 2.04 mmol), tert-butyl 3-aminopyrrolidine-1-carboxylate (4.18 g, 22.44 mmol) and $Cs_2CO_3$ (20 g, 61 mmol), and the reaction was stirred at 105° C. for overnight. The mixture was cooled to room temperature and diluted with ethyl acetate (200 mL) and brine (200 mL). The organic layer was separated and concentrated in vacuum. The residue was purified using silica gel column chromatography eluting with ethyl acetate in petroleum ether (EA/PE=1/100 to 1/2) to afford the titled compound (7.0 g, yield: 93%) as a yellow oil. LC-MS (ESI): m/z 351.5 $[M+H]^+$.

b) methyl 2-methoxy-4-(pyrrolidin-3-ylamino)benzoate hydrochloride

A mixture of tert-butyl 3-((3-methoxy-4-(methoxycarbonyl)phenyl)amino)pyrrolidine-1-carboxylate (7.0 g, 20 mmol) in HCl (4 M in dioxane, 10 mL) solution was stirred at room temperature for 18 hours. The mixture was concentrated in vacuum at 50° C. and dried to afford the title compound (5.3 g, yield: 92.5%) as a yellow solid. LC-MS (ESI): m/z 251.1 [M−HCl+H].

c) methyl 2-methoxy-4-((1-methylpyrrolidin-3-yl)amino)benzoate

To a solution of methyl 2-methoxy-4-(pyrrolidin-3-ylamino)benzoate hydrochloride (1.0 g, 3.49 mmol) in methanol (20 mL) were added formaldehyde (0.21 g, 6.97 mmol, 30% in water) and sodium cyanoborohydride (0.26 g, 4.18 mmol) and the reaction was stirred at room temperature for 2 hours. The reaction was concentrated in vacuum and the residue was purified using silica gel column chromatography eluting with methanol in dichloromethane (MeOH/DCM=0/1 to 1/15, v/v) to afford the titled compound (430 mg, yield: 46.8%) as a yellow solid. LC-MS (ESI): m/z 264.9 $[M+H]^+$.

d) 2-methoxy-4-((1-methylpyrrolidin-3-yl)amino)benzoic Acid

A mixture of methyl 2-methoxy-4-((1-methylpyrrolidin-3-yl)amino)benzoate (600.00 mg, 1.63 mmol), LiOH (684 mg, 16.28 mmol), MeOH (20 mL), $H_2O$ (10 mL) was heated to 70° C. and the mixture was stirred at this temperature for 18 hours. The reaction was cooled to room temperature. The pH of mixture was adjusted to 6-7. The mixture was concentrated in vacuum to afford residue. EtOH (50 mL) was added and the mixture was stirred at room temperature for 20 minutes and filtered. The filtrate was concentrated in vacuum to afford the titled compound (400 mg, yield: 88%) as a white foam. LC-MS (ESI): m/z 250.9 $[M+H]^+$.

e) 2-methoxy-4-((1-methylpyrrolidin-3-yl)amino)-N-((5-(thiophen-2-yl)-1,3,4-oxadiazol-2-yl)methyl)benzamide To a solution of 2-methoxy-4-((1-methylpyrrolidin-3-yl)amino)benzoic acid (400 mg, 1.60 mmol) in DMF (20 mL) were added DIEA (524 mg, 4.06 mmol) and BOP (539 mg, 1.22 mmol) and the reaction was stirred at room temperature for 5 minutes. (5-(thiophen-2-yl)-1,3,4-oxadiazol-2-yl)methanamine TFA salt (300 mg, 1.02 mmol) in DMF (20 mL) was added in one portion. The reaction was stirred at room temperature for 30 minutes. The mixture was purified by silica gel column chromatography eluting with methanol in DCM (MeOH/DCM=0/1 to 1/10, v/v) which was further purified by preparative-HPLC (Base method) to afford the title compound (0.16 g, yield: 38%) as a white solid. LC-MS (ESI): m/z 414.2 $[M+H]^+$. $^1H$ NMR (400 MHz, DMSO-$d_6$) δ 8.55 (t, J=5.6 Hz, 1H), 7.93 (dd, J=5.0, 1.1 Hz, 1H), 7.77 (dd, J=3.7, 1.1 Hz, 1H), 7.67 (d, J=8.4 Hz, 1H), 7.27 (dd, J=5.0, 3.8 Hz, 1H), 6.50 (d, J=6.9 Hz, 1H), 6.21 (d, J=8.5 Hz, 2H), 4.73 (d, J=5.6 Hz, 2H), 3.96 (s, 1H), 3.88 (s, 3H), 2.73 (dd, J=9.2, 6.7 Hz, 1H), 2.58 (dd, J=13.8, 8.2 Hz, 1H), 2.37 (dt, J=9.7, 6.0 Hz, 2H), 2.29-2.19 (m, 4H), 1.59 (d, J=6.5 Hz, 1H).

Example 44

77

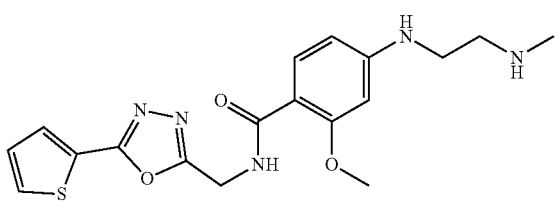

2-methoxy-4-((2-(methylamino)ethyl)amino)-N-((5-(thiophen-2-yl)-1,3,4-oxadiazol-2-ylmethyl)benzamide a) tert-butyl (2-((3-methoxy-4-(((5-(thiophen-2-yl)-1,3,4-oxadiazol-2-yl)methyl)carbamoyl) phenylamino)ethyl)(methyl)carbamate To a solution of 4-bromo-2-methoxy-N-((5-(thiophen-2-yl)-1,3,4-oxadiazol-2-yl) methyl)benzamide (300 mg, 0.761 mmol) in dioxane (6 mL) were added tert-butyl (2-aminoethyl)(methyl)carbamate (199 mg, 1.1 mmol), Pd$_2$(dba)$_3$ (69.68 mg, 0.076 mmol), BINAP (47.38 mg, 0.076 mmol) and Cs$_2$CO$_3$ (991 mg, 3.04 mmol), the mixture was degassed with N$_2$ for three times. The reaction was stirred at 105° C. for 18 hours. The reaction was filtered, the filtrate was diluted with water (15 mL), the mixture was extracted with ethyl acetate (20 mL×3). The organic layer were combined, washed with brine (20 mL), dried over anhydrous Na$_2$SO$_4$, filtered and concentrated in vacuo. The residue was purified using silica gel column chromatography eluting with ethyl acetate in petroleum ether (PE:EA=4:1 to 1:4) to afford the titled compound (200 mg, yield: 27%). LC-MS (ESI): m/z 488.2 [M+H]$^+$.

b) 2-methoxy-4-((2-(methylamino)ethyl)amino)-N-((5-(thiophen-2-yl)-1,3,4-oxadiazol-2-yl)methyl)benzamide To a solution of tert-butyl (2-((3-methoxy-4-(((5-(thiophen-2-yl)-1,3,4-oxadiazol-2-yl)methyl)carbamoyl)phenyl)amino)ethyl)methyl)carbamate (200 mg, 0.41 mmol) in dichloromethane (8 mL) was added TFA (2 mL). The reaction was stirred at room temperature for 2 hours. The reaction was concentrated in vacuo. The residue was purified with preparative HPLC to afford the titled compound (17 mg, yield: 21%). LC-MS (ESI): m/z 388.2 [M+H]$^+$. $^1$H NMR (400 MHz, DMSO-d$_6$) δ 8.54 (d, J=5.4 Hz, 1H), 8.01-7.87 (m, 1H), 7.77 (d, J=2.6 Hz, 1H), 7.67 (d, J=9.2 Hz, 1H), 7.27 (dd, J=4.9, 3.8 Hz, 1H), 6.25 (t, J=6.1 Hz, 3H), 4.73 (d, J=5.7 Hz, 2H), 3.88 (s, 3H), 3.16 (dd, J=11.8, 6.0 Hz, 3H), 2.68 (t, J=6.2 Hz, 2H), 2.31 (s, 3H).

The compounds below were synthesized following the procedures described in Example 44.

| No. | Structure | Name | MS: m/z [M + H]$^+$ | $^1$H NMR (400 MHz, DMSO-d$_6$) |
|---|---|---|---|---|
| 78 | 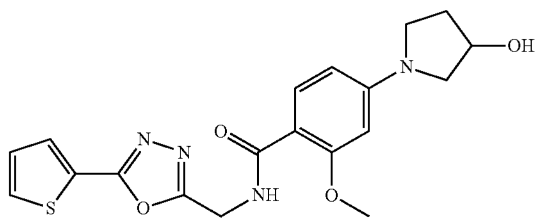 [SMILES: COc1cc(N2CCC(O)C2)ccc1C(=O)NCc1nnc(-c2cccs2)o1] | 4-(3-hydroxypyrrolidin-1-yl)-2-methoxy-N-((5-(thiophen-2-yl)-1,3,4-oxadiazol-2-yl)methyl)benzamide | 375.1 | δ 8.54 (d, J = 5.7 Hz, 1H), 7.93 (d, J = 4.0 Hz, 1H), 7.77 (d, J = 2.7 Hz, 1H), 7.67 (d, J = 8.5 Hz, 1H), 7.32-7.17 (m, 1H), 6.33-6.17 (m, 3H), 4.73 (t, J = 5.3 Hz, 3H), 3.88 (s, 3H), 3.56 (dd, J = 11.5, 5.8 Hz, 2H), 3.17 (dd, J = 11.7, 5.8 Hz, 2H). |
| 79 | 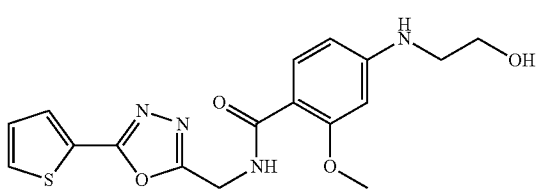 [SMILES: COc1cc(NCCO)ccc1C(=O)NCc1nnc(-c2cccs2)o1] | 4-((2-hydroxyethyl)amino)-2-methoxy-N-((5-(thiophen-2-yl)-1,3,4-oxadiazol-2-yl)methyl)benzamide | 401.0 | δ 8.58 (s, 1H), 7.93 (d, J = 5.0 Hz, 1H), 7.76 (t, J = 6.5 Hz, 2H), 7.29-7.16 (m, 1H), 6.19 (d, J = 9.0 Hz, 1H), 6.10 (s, 1H), 5.01 (d, J = 3.7 Hz, 1H), 4.74 (d, J = 5.6 Hz, 2H), 4.41 (s, 1H), 3.94 (s, 3H), 3.46 (dd, J = 10.8, 4.7 Hz, 1H), 3.39 (dd, J = 12.4, 6.9 Hz, 2H), 3.17 (d, J = 10.5 Hz, 1H), 2.06-2.02 (m, 1H), 1.93-1.88 (m, 1H). |

Example 45

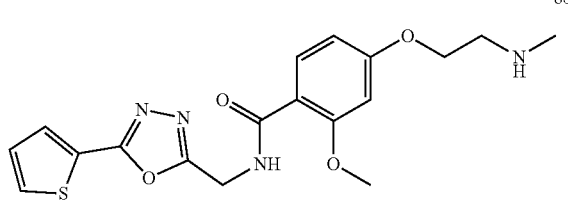

2-methoxy-4-(2-(methylamino)ethoxy)-N-((5-(thiophen-2-yl)-1,3,4-oxadiazol-2-yl)methyl)benzamide a) 2-((tert-butoxycarbonyl)(methyl)amino)ethyl Methanesulfonate To a solution of tert-butyl (2-hydroxyethyl)(methyl)carbamate (1.0 g, 5.7 mmol) in DCM (10 mL) were added triethylamine (693 mg, 6.8 mmol) and a solution of methanesulfonyl chloride (719 mg, 6.3 mmol) in DCM (2 mL) dropwise at 0° C. and the reaction was warmed to room temperature. The reaction was allowed to stir at this temperature for 1.5 hours. The reaction was washed with water (10 mL) and the organic layer was separated. The organic layer was concentrated in vacuo. The residue was purified using silica gel column chromatography eluting with ethyl acetate in petroleum ether (PE:EA=10:1 to 1:1) to afford the titled compound (1.16 g, yield: 80%) as a yellow oil.

b) tert-butyl (2-(3-methoxy-4-(((5-(thiophen-2-yl)-1,3,4-oxadiazol-2-yl)methyl)carbamoyl) phenoxy)ethyl)(methyl)carbamate To a solution of 2-((tert-butoxycarbonyl)(methyl)amino) ethyl methanesulfonate (458 mg, 1.81 mmol) in DMF (5 mL) were added 4-hydroxy-2-methoxy-N-((5-(thiophen-2-yl)-1,3,4-oxadiazol-2-yl)methyl)benzamide (300 mg, 0.91 mmol) and $Cs_2CO_3$ (589 mg, 1.81 mmol), and the reaction was stirred at 90° C. for 5 hours. The reaction was diluted with water (20 mL), the mixture was extracted with ethyl acetate (20 mL×3), the organic layers were combined, washed with brine (20 mL), dried over anhydrous $Na_2SO_4$, filtered and concentrated in vacuo. The residue was purified using silica gel column chromatography eluting with ethyl acetate in petroleum ether (PE:EA=10:1 to 1:4) to afford the titled compound (53 mg, yield: 6.0%). LC-MS (ESI): m/z 489.0 $[M+H]^+$.

c) 2-methoxy-4-(2-(methylamino)ethoxy)-N-((5-(thiophen-2-yl)-1,3,4-oxadiazol-2-yl)methyl)benzamide To a solution of tert-butyl (2-(3-methoxy-4-(((5-(thiophen-2-yl)-1,3,4-oxadiazol-2-yl)methyl)carbamoyl) phenoxy)ethyl)(methyl)carbamate (53 mg, 0.11 mmol) in DCM (5 mL) was added TFA (1 mL), and the reaction was stirred at room temperature for 1 hr. The reaction was concentrated in vacuo. The residue was purified with preparative HPLC to afford the titled compound (9.94 mg, yield: 24%). LC-MS (ESI): m/z 389.1 $[M-H]^-$. $^1$H NMR (400 MHz, DMSO-$d_6$) δ 8.76 (t, J=5.5 Hz, 1H), 7.93 (d, J=4.9 Hz, 1H), 7.84 (d, J=8.7 Hz, 1H), 7.77 (d, J=3.3 Hz, 1H), 7.32-7.18 (m, 1H), 6.74-6.57 (m, 2H), 4.75 (d, J=5.6 Hz, 2H), 4.10 (t, J=5.5 Hz, 2H), 3.93 (s, 3H), 3.32-3.28 (m, 1H), 2.87 (t, J=5.3 Hz, 2H), 2.35 (s, 3H).

The compounds below were synthesized following the procedures described in Example 45.

| No. | Structure | Name | MS: m/z $[M + H]^+$ | $^1$H NMR (400 MHz, DMSO-$d_6$) |
|---|---|---|---|---|
| 81 | 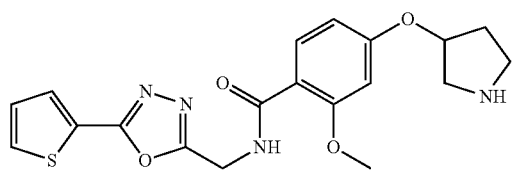 [SMILES: COc1cc(OC2CCNC2)ccc1C(=O)NCc1nnc(-c2cccs2)o1] | 2-methoxy-4-(pyrrolidin-3-yloxy)-N-((5-(thiophen-2-yl)-1,3,4-oxadiazol-2-yl)methyl)benzamide | 501.1 | δ 8.76 (d, J = 6.1 Hz, 1H), 7.93 (dd, J = 5.0, 1.1 Hz, 1H), 7.90-7.64 (m, 2H), 7.28 (dd, J = 5.0, 3.8 Hz, 1H), 6.76-6.47 (m, 2H), 4.95 (s, 1H), 4.75 (d, J = 5.5 Hz, 2H), 3.92 (s, 3H), 3.20-2.99 (m, 1H), 2.83 (dd, J = 25.8, 12.7 Hz, 2H), 2.18-1.88 (m, 2H), 1.33-0.95 (m, 2H). |

Example 46

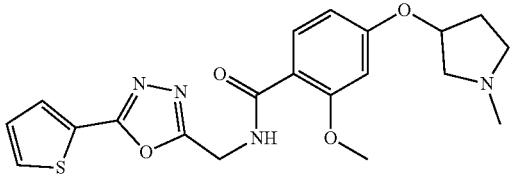

2-methoxy-4-((1-methylpyrrolidin-3-yl)oxy)-N-((5-(thiophen-2-yl)-1,3,4-oxadiazol-2-yl)methyl)benzamide To a solution of 2-methoxy-4-(pyrrolidin-3-yloxy)-N-((5-(thiophen-2-yl)-1,3,4-oxadiazol-2-yl) methyl)benzamide (240 mg, 0.6 mmol) in methanol (10 m) were added acetic acid (22 mg, 0.12 mmol), formaldehyde (126 mg, 4.20 mmol), and 2-methylpyridine borane (641 mg, 6.0 mmol, and the reaction was stirred at 80° C. for 2 hours. The reaction was concentrated in vacuo. The residue was purified using silica gel column chromatography eluting with methanol in DCM (MeOH:DCM=1:100 to 1:10, v/v) to afford crude product. The crude was further purified with preparative HPLC to afford the titled compound (2.18 mg, yield: 0.8%) as a white solid. LC-MS (ESI): m/z 415.5 [M+H]$^+$. $^1$H NMR (400 MHz, DMSO-d$_6$) δ 8.75 (t, J=5.4 Hz, 1H), 7.93 (dd, J=5.0, 1.1 Hz, 1H), 7.81 (s, 1H), 7.77 (dd, J=3.7, 1.1 Hz, 2H), 7.28 (dd, J=5.0, 3.7 Hz, 1H), 6.60 (m, 2H), 4.97 (s, 1H), 4.75 (d, J=5.6 Hz, 2H), 3.92 (s, 3H), 2.86-2.73 (m, 1H), 2.72-2.60 (m, 2H), 2.41-2.31 (m, 2H), 2.27 (s, 3H), 1.76 (d, J=7.1 Hz, 1H).

Example 47

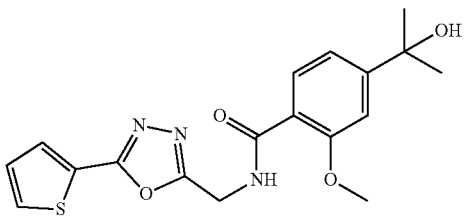

4-(2-hydroxypropan-2-yl)-2-methoxy-N-((5-(thiophen-2-yl)-1,3,4-oxadiazol-2-yl)methyl)benzamide a) 4-(2-hydroxypropan-2-yl)-2-methoxybenzoic Acid A solution of 4-bromo-2-methoxybenzoic acid (400 mg, 1.73 mmol) in THF (5 mL) was cooled to −65° C., n-BuLi (3.3 mL, 0.48 mmol, 1.6 M) was added. The reaction was stirred at this temperature for 30 min. To the mixture was added acetone (0.19 mL, 2.5 mmol) dropwise, the mixture was slowly warmed to 0° C. and stirred for 30 minutes. The mixture was diluted with ethyl acetate (5 mL) and saturated aqueous NH$_4$Cl solution (5 mL). The organic layer was separated, washed with brine (5 mL), filtered and concentrated in vacuo. The residue was purified using silica gel column chromatography eluting with methanol in dichloromethane (MeOH:DCM=0:1 to 1:7) to afford the title compound (50 mg, yield: 14%) as a colorless oil. LC-MS (ESI): m/z 211.0 [M+H]$^+$.

b) 4-(2-hydroxypropan-2-yl)-2-methoxy-N-((5-(thiophen-2-yl)-1,3,4-oxadiazol-2-yl)methyl)benzamide To a solution of 4-(2-hydroxypropan-2-yl)-2-methoxybenzoic acid (50 mg, 0.24 mmol) in DMF (5 mL) were added BOP (210 mg, 0.48 mmol), DIEA (0.12 mL, 0.71 mmol), and [5-(thiophen-2-yl)-1,3,4-oxadiazol-2-yl]methanamine (43 mg, 0.24 mmol) The reaction was stirred at room temperature for 1.5 hours. The reaction was purified by preparative HPLC (Waters 2767/2545/2489, Waters Xbridge C18 10 um OBD 19*250 mm, Mobile Phase A: 0.1% NH$_4$HCO$_3$ in water, Mobile Phase B: CH$_3$CN, 20 mL/min, RT) to afford the title compound (7 mg, yield: 7.6%) as a white solid. LC-MS (ESI): m/z 374.1[M+H]$^+$. $^1$H NMR (400 MHz, DMSO-d$_6$) δ 8.88 (t, J=5.7 Hz, 1H), 7.94 (d, J=4.0 Hz, 1H), 7.76 (t, J=6.1 Hz, 2H), 7.27 (dd, J=9.5, 4.6 Hz, 2H), 7.11 (d, J=8.1 Hz, 1H), 5.18 (s, 1H), 4.77 (d, J=5.6 Hz, 2H), 3.93 (s, 3H), 1.44 (s, 6H).

Example 48

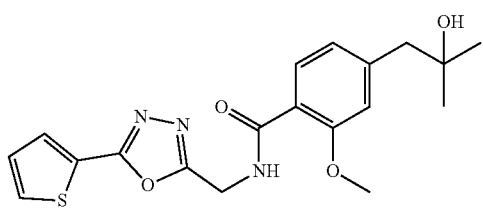

4-(2-hydroxy-2-methylpropyl)-2-methoxy-N-((5-(thiophen-2-yl)-1,3,4-oxadiazol-2-yl)methyl)benzamide a) methyl 4-(2-hydroxy-2-methylpropyl)-2-methoxybenzoate LDA (8.3 mL, 0.2 mmol, 2M in THF) was added to a solution of 1,3-dimethyl-1,3-diazinan-2-one (7.8 mL, 64 mmol) in THF (30 mL) at −70° C., followed by methyl 2-methoxy-4-methylbenzoate (2.91 g, 16 mmol). The reaction was stirred at −70° C. for 2 hours and acetone (1.78 mL, 24.224 mmol) was added. The reaction was warmed to 0° C. and was stirred at that temperature for 1 hour. The mixture was diluted with brine (20 mL) and extracted with ethyl acetate (40 mL-2). The combined organic layers was washed with bine (20 mL), dried with Na$_2$SO$_4$, filtered and concentrated in vacuo. The residue was purified using silica gel column chromatography eluting with ethyl acetate in petroleum ether (PE/EA=1/0 to 1.5/1) to afford the title compound (900 mg, yield: 19.2%) as a yellow oil. LC-MS (ESI): m/z 238.8 [M+H]$^+$.

b) 4-(2-hydroxy-2-methylpropyl)-2-methoxybenzoic Acid

To a solution of methyl 4-(2-hydroxy-2-methylpropyl)-2-methoxybenzoate (1.7 g, 7.13 mmol) in MeOH (20 mL) were added H$_2$O (20 mL) and LiOH.H$_2$O (3.00 g, 71 mmol). The reaction was stirred at 60° C. for 2 hours. The mixture was cooled to room temperature and adjusted the pH to 7~-8 with aqueous HCl (1.0 M). The organic solvent was removed in vacuum and water (20 mL) was added. The mixture was acidified with hydrochloric acid (5 mL) and was extracted with ethyl acetate (3×50 mL). The combined organic layers were dried with Na$_2$SO$_4$, filtered and concentrated to afford the title compound (1.4 g, yield: 72%) as a yellow oil. LC-MS (ESI): m/z 225.1 [M+H]$^+$.

c) 4-(2-hydroxy-2-methylpropyl)-2-methoxy-N-((5-(thiophen-2-yl)-1,3,4-oxadiazol-2-ylmethyl)benzamide To a solution of (5-(thiophen-2-yl)-1,3,4-oxadiazol-2-yl)methanamine TFA salt (2.19 g, 5.563 mmol) in DMF (15 mL) were added DIEA (2.51 mL, 15.171 mmol), BOP (2.68 g, 6.068 mmol), and 4-(2-hydroxy-2-methylpropyl)-2-methoxybenzoic acid (1.4 g, 5.057 mmol). The reaction was stirred at room temperature for 1 hour. The reaction was diluted with ethyl acetate (30 mL) and brine (50 mL). The organic layer was separated, dried with $Na_2SO_4$, filtered and concentrated in vacuo. The residue was purified using silica gel column chromatography eluting with ethyl acetate in petroleum ether (PE:EA=1:0-1/2) to afford the title compound (1.0 g, 2.59 mmol, yield: 51%) as an off-white solid. LC-MS (ESI): m/z 388.1 [M+H]+. $^1$H NMR (400 MHz, DMSO-$d_6$) δ 8.87 (t, J=5.6 Hz, 1H), 7.93 (dd, J=5.0, 1.2 Hz, 1H), 7.78 (dd, J=3.7, 1.2 Hz, 1H), 7.73 (d, J=7.9 Hz, 1H), 7.28 (dd, J=5.0, 3.7 Hz, 1H), 7.02 (s, 1H), 6.90 (dd, J=7.9, 1.1 Hz, 1H), 4.77 (d, J=5.7 Hz, 2H), 4.39 (s, 1H), 3.91 (s, 3H), 2.70 (s, 2H), 1.09 (s, 6H).

Example 49

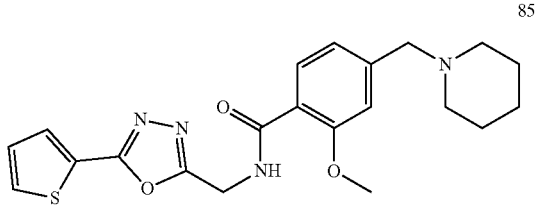 [SMILES: COc1cc(CN2CCCCC2)ccc1C(=O)NCc1nnc(-c2cccs2)o1]

2-methoxy-4-(piperidin-1-ylmethyl)-N-((5-(thiophen-2-yl)-1,3,4-oxadiazol-2-ylmethyl)benzamide a) 4-formyl-2-methoxybenzoic Acid A solution of 4-bromo-2-methoxybenzoic acid (4.0 g, 17 mmol) in THF (50 mL) was cooled to -65° C., n-butyllithium (15.2 mL, 0.16 mmol, 2.5 M in THF) was added. The reaction was stirred at this temperature for 30 minutes. To this mixture was added DMF (1.62 mL, 21 mmol) dropwise, then the whole mixture was slowly warmed to 0° C. and stirred for 30 minutes. The mixture was diluted with ethyl acetate (30 mL), washed with saturated aqueous $NH_4Cl$ solution (50 mL) and brine (50 mL). The organic layer was dried with $Na_2SO_4$, filtered and concentrated in vacuo. The residue was purified using silica gel column chromatography eluting with methanol in dichloromethane (MeOH:DCM=0:1 to 1:20) to afford the title compound (2.3 g, yield: 55%) as a yellow solid. LC-MS (ESI): m/z 179.1 [M–H]$^-$.

b) 4-formyl-2-methoxy-N-((5-(thiophen-2-yl)-1,3,4-oxadiazol-2-yl)methyl)benzamide To a solution of 4-formyl-2-methoxybenzoic acid (300 mg, 1.249 mmol) in DMF (10 mL) were added BOP (828 mg, 1.9 mmol), DIEA (0.62 mL, 3.7 mmol) and (5-(thiophen-2-yl)-1,3,4-oxadiazol-2-yl)methanamine TFA salt (347.19 mg, 1.249 mmol). The reaction was stirred at room temperature for 2 hours. The reaction was diluted with ethyl acetate (20 mL) and brine (40 mL). The organic layer was separated, washed with brine (40 mL), dried with $Na_2SO_4$, filtered and concentrated in vacuo. The residue was purified using silica gel column chromatography eluting with methanol in dichloromethane (MeOH/DCM=0/1 to 1/20) to afford the title compound (120 mg, yield: 26%) as a white solid. LC-MS (ESI): m/z 344.1 [M+H]$^+$.

c) 2-methoxy-4-(piperidin-1-ylmethyl)-N-(5-(thiophen-2-yl)-1,3,4-oxadiazol-2-yl)methyl)benzamide To a solution of 4-formyl-2-methoxy-N-((5-(thiophen-2-yl)-1,3,4-oxadiazol-2-yl)methyl) benzamide (50 mg, 0.15 mmol) in MeOH (5 mL) were added piperidine (0.2 mL, 2.02 mmol) and acetic acid (0.01 mL, 0.175 mmol), and the reaction was stirred at room temperature for 1 hour. To this mixture was added sodium cyanoborahydride (18 mg, 0.291 mmol), and the reaction was stirred at that temperature for 2 hours. After reaction completed, the mixture was purified by preparative-HPLC (Waters 2767/2545/2489, Waters Xbridge C18 10 um OBD 19*250 mm, Mobile Phase A: 0.1% $NH_4OH$ in water, Mobile Phase B: $CH_3CN$, Flow: 20 mL/min, Column temp; RT) to afford the title compound (18 mg, yield; 30%) as a white solid. LC-MS (ESI): m/z 413.1 [M+H]$^+$. $^1$H NMR (400 MHz, DMSO-$d_6$) δ 8.89 (t, J=5.7 Hz, 1H), 7.94 (dd, J=5.0, 1.2 Hz, 1H), 7.79-7.75 (m, 2H), 7.28 (dd, J=5.0, 3.7 Hz, 1H), 7.08 (s, 1H), 6.99 (d, J=7.3 Hz, 1H), 4.77 (d, J=5.7 Hz, 2H), 3.91 (s, 3H), 3.46 (s, 2H), 2.33 (s, 4H), 1.53-1.47 (m, 4H), 1.39 (s, 2H).

The compounds below were synthesized following the procedures described in Example 49.

| No. | Structure | Name | MS: m/z [M + H]$^+$ | $^1$H NMR (400 MHz, DMSO-$d_6$) |
|---|---|---|---|---|
| 86 | 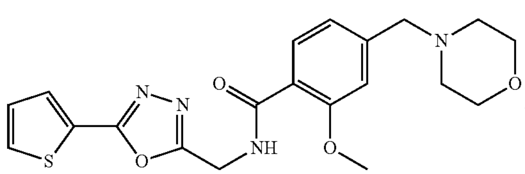 [SMILES: COc1cc(CN2CCOCC2)ccc1C(=O)NCc1nnc(-c2cccs2)o1] | 2-methoxy-4-(morpholinomethyl)-N-((5-(thiophen-2-yl)-1,3,4-oxadiazol-2-yl)methyl)benzamide | 415.1 | δ 8.89 (t, J = 5.6 Hz, 1H), 7.94 (dd, J = 5.0, 1.1 Hz, 1H), 7.78 (dd, J = 4.5, 3.4 Hz, 2H), 7.28 (dd, J = 5.0, 3.8 Hz, 1H), 7.10 (s, 1H), 7.01 (d, J = 7.9 Hz, 1H), 4.77 (d, J = 5.7 Hz, 2H), 3.92 (s, 3H), 3.62-3.55 (m, 4H), 3.51 (s, 2H), 2.37 (s, 4H). |

Biological Assay and Data

As stated above, the compounds of Formula I are MIF inhibitors, and are useful in the treatment of diseases mediated by MIF. The biological activities of the compounds of can be determined by using any suitable assay for determining the activity of a candidate compound as a MIF inhibitor.

MIF Enzymatic Assays

Tautomerase Assay Using pHPP as substrate

This assay measured MIF's tautomerase activity in a cell-free system and was based on the determination of initial rates of the MIF-catalyzed conversion of the ketonic into the enolic tautomer of pHPP. This was achieved by spectrophotometric quantification of the complex between borate and the product of the reaction (enolic pHPP). The substrate was prepared by conversion of the enolic pHPP into its ketonic form. To achieve this, 0.5 M pHPP in methanol was diluted 10-fold with 50 mM sodium acetate buffer at pH 6.0, and then the suspension was shaken for 24 h at room temperature in darkness, and finally stored at 4° C. for not more than 1 week, with 5 min sonication being recommended before use.

Assays were performed in small-volume clear-bottom black 96 or 384-well polystyrene plates (Greiner Bio-One). First, 2 μL of the enzyme solution containing 6 nM of MIF in DPBS, 0.025% w/v BSA, and 300 μM CHAPS was dispensed onto sample and negative control wells using Multidrop Combi with metallic tip cassettes (Thermo Fisher Scientific) previously treated with Sigmacote. Then, 2 μL of the same buffer without MIF was dispensed onto positive control wells. The reaction was started by addition of the following to all wells: 2 μL of substrate solution containing 3 mM ketonic pHPP in 200 mM boric acid, 25 mM sodium phosphate, 0.025% w/v BSA, and 300 μM CHAPS at pH 6.0. In order to remove bubbles, the plate was centrifuged in an Allegra 25R centrifuge (Beckman Coulter, Inc., Brea, CA) at 1000 rpm for 2 min at room temperature. Then, the plate was read in an EnVision. Final concentrations of enzyme and substrate were 3 nM and 1.5 mM, respectively. Initial rates were calculated for each well as the slope of the absorbance progress curve.

All exemplified compounds (Examples 1-85) were tested in the MIF tautomerase assay or a similar assay described above. The data mentioned below represents a mean $pIC_{50}$ value of multiple test results. It is understood that the data illustrated below may have reasonable variation depending on the specific conditions and procedures used by the person conducting the testing.

Assay Data

The $pIC_{50}$ data from assays for measuring the inhibitory effect on MIF by compounds are listed in table 1 below.

TABLE 1

Inhibition of the MIF Enzyme in vitro by compounds

| Compound # | Tautomerase Inhibition $pIC_{50}$ |
| --- | --- |
| 1 | <5 |
| 2 | 5.07 |
| 3 | <5 |
| 4 | 5.58 |
| 5 | 7.73 |
| 6 | 7.17 |
| 7 | <5 |
| 8 | 6.54 |
| 9 | 7.64 |
| 10 | 5.90 |
| 11 | 5.68 |
| 12 | <5 |
| 13 | <5 |
| 14 | 5.91 |
| 15 | 6.70 |
| 16 | 7.09 |
| 17 | 7.98 |
| 18 | 7.63 |
| 19 | 7.54 |
| 20 | 6.76 |
| 21 | 7.59 |
| 22 | 7.91 |
| 23 | 7.50 |
| 24 | 7.31 |
| 25 | 7.68 |
| 26 | 7.95 |
| 27 | 7.73 |
| 28 | 7.42 |
| 29 | 8.14 |
| 30 | 7.90 |
| 31 | 8.16 |
| 32 | 8.02 |
| 33 | 7.29 |
| 34 | 7.33 |
| 35 | <5 |
| 36 | <5 |
| 37 | 7.44 |
| 38 | 6.31 |
| 39 | 4.06 |
| 40 | 5.58 |
| 41 | 1.77 |
| 42 | 3.10 |
| 43 | 5.09 |
| 44 | <5 |
| 45 | <5 |
| 46 | 3.70 |
| 47 | <5 |
| 48 | <5 |
| 49 | <5 |
| 50 | <5 |
| 51 | 6.29 |
| 52 | 4.20 |
| 53 | <5 |
| 54 | <5 |
| 55 | 6.22 |
| 56 | 6.13 |
| 57 | 6.29 |
| 58 | 5.95 |
| 59 | 5.90 |
| 60 | 5.28 |
| 61 | <5 |
| 62 | <5 |
| 63 | <5 |
| 64 | 4.79 |
| 65 | <5 |
| 66 | <5 |
| 67 | 4.62 |
| 68 | 3.23 |
| 69 | 5.98 |
| 70 | 6.12 |
| 71 | 6.21 |
| 72 | <5 |
| 73 | <5 |
| 74 | <5 |
| 75 | <5 |
| 76 | 1.77 |
| 77 | 5.66 |
| 78 | 6.24 |
| 79 | 6.15 |
| 80 | 5.62 |
| 81 | 5.60 |
| 82 | 5.53 |
| 83 | 5.98 |
| 84 | 6.04 |
| 85 | 5.20 |
| 86 | 5.47 |

Cell Proliferation Assays

The assay measures the ability of a compound to inhibit cell proliferation using Cell Counting Kit-8 (CCK-8), which allows sensitive colorimetric assays for the determination of cell viability in cell proliferation and cytotoxicity assays. The highly water-soluble tetrazolium salt, WST-8, is reduced by dehydrogenase activities in cells to give a yellow-color formazan dye, which is soluble in the tissue culture media. The amount of the formazan dye, generated by the activities of dehydrogenases in cells, is directly proportional to the number of living cells.

The assay was performed based on the instruction of the manufacturer (Dojindo Molecular Technologies Inc., Rockville, MD, USA). To start the assay, BV2 cells were seeded at a density of $2\times10^6$ cells/well into 96-well plates and treated with test compounds, which were used at a top final assay concentration of 33.3 μM, diluted in assay medium with 1:3 dilutions to produce 10 point concentration responses, for 48 h. After incubation, the CCK-8 solution (10 μl) was added to each well of the plate and the plates were incubated in incubator at 37° C. for 3 h. Absorbance was recorded three times independently using a microplate reader (Bio-Rad Laboratories, Richmond, CA, USA) at 450 nm.

Selected examples were tested in the BV2 cell proliferation. The data mentioned below represents a mean $pIC_{50}$ value of multiple test results. It is understood that the data illustrated below may have reasonable variation depending on the specific conditions and procedures used by the person conducting the testing.

The $pIC_{50}$ data from assays for measuring the inhibitory effect on MIF by compounds are listed in table 2 below.

TABLE 2

Inhibition of the BV2 and U251 cell profileration by compounds

| Compound # | BV2 Profileration $pIC_{50}$ | U251 Profileration $pIC_{50}$ |
|---|---|---|
| 17 | 4.94 | <3 |
| 19 | <3 | <3 |
| 21 | <3 | <3 |
| 22 | <3 | <3 |
| 44 | 4.34 | <3 |
| 46 | <3 | <3 |
| 51 | 4.88 | <3 |
| 52 | 5.44 | <3 |
| 56 | 4.79 | <3 |
| 58 | 4.45 | <3 |
| 59 | 4.39 | <3 |
| 63 | 4.67 | <3 |
| 69 | 4.35 | <3 |
| 72 | 3.91 | <3 |
| 73 | 4.63 | <3 |
| 74 | 4.60 | <3 |
| 75 | 4.55 | <3 |
| 76 | <3 | <3 |
| 77 | <3 | <3 |
| 78 | 4.10 | <3 |
| 79 | <3 | <3 |
| 80 | 4.58 | <3 |
| 81 | <3 | 4.45 |
| 82 | <3 | <3 |
| 83 | <3 | <3 |
| 84 | 4.38 | <3 |
| 85 | <3 | <3 |
| 86 | <3 | <3 |

What is claimed is:

1. A compound or a pharmaceutically acceptable salt thereof, wherein the compound is selected from
N-(5-(4-hydroxyphenyl)-1,3,4-oxadia.zol-2-yl)-2,4-dimethoxybenzamide;
2,4-dimethoxy-N-(5-(thiazol-5-yl)-1,3,4-oxadiazol-2-yl)benzamide;
2,4-dimethoxy-N-(5-(3-methylthiophen-2-yl)-1,3,4-oxadiazol-2-yl)benzamide;
N-(5-(3-fluorothiophen-2-yl)-1,3,4-oxadiazol-2-yl)-2,4-dimethoxybenzamide;
2-ethoxy-N-(5-(thiophen-2-yl)-1,3,4-oxadiazol-2-yl)benzamide;
2-fluoro-4-methoxy-N-(5-(thiophen-2-yl)-1,3,4-oxadiazol-2-yl)benzamide;
methyl 2((5-(thiophen-2-yl)-1,3,4-oxadiazol-2-yl)carbamoyl)benzoate;
4-(benzyloxy)-2-methoxy-N-(5-(thiophen-2-yl)-1,3,4-oxa.diazol-2-yl)benzamide;
4-hydroxy-2-methoxy-N-(5-(thiophen-2-yl)-1,3,4-oxadiazol-2-yl)benzamide;
4-(2-hydroxyethoxy)-2-methoxy-N-(5-(thiophen-2-yl)-1,3,4-oxadiazoi-2-yl)benzamide;
4-(2-(benzyloxy)ethoxy)-2-methoxy-N-(5-(thiophen-2-yl)-1,3,4-oxadiazol-2-yl)benzamide;
2-(3-methoxy-4-((5-(thiophen-2-yl)-1,3,4-oxadiazol-2-yl)carbamoyl)phenoxy)acetic acid;
4-(2-(dimethylamino)ethoxy)-2-methoxy-N-(5-(thiophen-2-yl)-1,3,4oxadiazol-2-yl)benzamide;
2-(3-methoxy-4-4-((5-(thiophen-2-yl)-1,3,4-oxadiazol-2-yl)carbamoyl)phenoxy)-2-methylpropanoic acid;
4-((2H-tetrazol-5-yl)methoxy)-2-methoxy-N-(5-(thiophen-2-yl)-1,3,4oxadiazol-2-yl)benzamide;
2-methoxy-4-((2-((5-methyl-2-oxo-1,3-dioxol-4-yl)methyl)-2H-tetrazol-5-y)methoxy)-N-(5-(thiophen-2-yl)-1,3,4-oxadiaziol-2-yl)benzamide;
2-methoxy-4-((1-((5-methyl-2-oxo 1,3 -dioxol-4-yl)methyl)-1H-tetrazol-5-yl)methoxy)-N-(5-(thiophen-2-yl)-1,3,4-oxadiazol-2-yObenzamide;
4-(3-cyanopropyl)-2-methoxy-N-(5-(thiophen-2-yl)-1,3,4-oxadiazol-2-yl)benzamide;
4-(3-(2H-tetrazol-5-yl)propyl)-2-methoxy-N-(5-(thiophen-2-yl)-1,3,4-oxadiazol-2-yl)berizamide;
Cis-4-(3-methoxy-4-((5-(thiophen-2-yl)-1,3,4-oxadiazol-2-yl(carbamoyl)phenyl)cyclohexane-1-carboxyl acid;
Trans-4-(3-methoxy-4-((5-(thiophen-2-yl)-oxadiazol-2-yl)carbamoyl)phenyl)cyclohexane-1-carboxylic acid;
3'-methoxy4'-((5-(thiophen-2-yl)-1,3,4-oxadiazol-2-yl)carbamoyl)-2,3,4,5-tetrahydro-[1,1'-biphenyl]-4-carboxylic acid;
(3-methoxy-4-((5-(thiophen-2-yl)-1,3,4-oxadiazol-2-yl)carbamoyl)phenyl)proline;
1-(3-methoxy-4-(5-(thiophen-2-yl)-1,3,4-oxadiazol-2-yl)carbamoyl)phenyl)piperidine-3-carboxylic acid;
2-((3-methoxy-4-((5-(thiophen-2-yl)-1,3,4-oxadiazol-2-yl)carbamoyl)phenyl)amino)-2-methylpropanoic acid;
4-(6-oxa-3-azabicyclo[3.1.1]heptan-3-yl)-2-methoxy-N-(5-(thiophen-2-yl)-1,3,4-oxadiazol-2-yl)benzamide;
2-methoxy-4-morpholino-N-(5-(thiazol-5-yl)-1,3,4-oxadiazol-2-yl)benzamide;
2-methoxy-4-morpholino-N-(5-(thiazol-5-yl)-1,3,4-oxadiazol-2-yl)benzenesulfonamide;
2-methoxy-N-methyl-4-morpholino-N-(5-(thiazol-5-yl)-1,3,4-oxadiazol-2-yl)benzamide;
2-methoxy-4-morpholino-N-(5-(thiophen-2-yl)-1,3,4-oxadiazol-2-yl)benzamide;
2,4-dimethoxy-N-((5-(thiophen-2-yl)-1,3,4-oxadiazol-2-yl)methyl)benzamide;
N-((5-(thiophen-2-yl)-1,3,4-oxadiazol-2-yl)methyl)-2-(trifluoromethoxy)benzamide;
2-hydroxy-N-((5-(thiophen-2-yl)-1,3,4-oxadiazol-2-yl)methyl)benzamide;

2,6-difluoro-N-((5-(thiophen-2-yl)-1,3,4-oxadiazol-2-yl)methyl)benzamide;
3-methoxy -N-((5-(thioplien-2-yl)- 1,3,4-oxadiazol-2-yl)methyl)isonicotinamide;
2-methoxy-N-((5-(thiophen-2-yl)- 1,3,4-oxadiazol-2-yl)methyl)nicotinamide;
1-methyl-N-((5-(thiophen-2-yl)-1,3,4-oxadiazol -2-yl)methyl)piperidine-4-carboxamide;
2-methoxy-4-morpholino-N-((5-(thiophen-2-yl)-1,3,4-oxadiazol-2-yl)methyl)benzamide;
2-methoxy-N-methyl-4-morpholino-N-((5-(thiophen-2-yl)-1,3,4-oxadiazol-2-y)methyl)benzamide;
N-ethyl-2-methoxy-z1-morpholino-N-((5-(thiophen-2-yl)-1,3,4-oxadiazol-2-yl)methyl)benzamide;
2-methoxy-3-morpholino-N-((5-(thiophen-2-yl)- 1,3,4-oxadiazol-2-yl)methyl)benzamide;
4-(2,6-dimethylmorpholino)-2-methoxy-N-((5-(thiophen-2-yl)-1,3,4-oxadiazol-2-yl)methyl)benzamide;
2-methoxy-4-(piperidin-1-yl)-N-((5-(thiophen-2-yl)-1,3,4-oxadiazol-2-yl)methyl)benzamide;
4-(6-oxa-3-azabicyclo[3.1.1]heptan-3-yl)-2-methoxy-N-((5-(thiophen-2-yl)-1,3,4-oxadiazol-2-yl)methyl)benzamide;
2-methoxy-4-(piperazin-1-yl)-N-((5-(thiophen-2-yl)-1,3,4-oxadiazol-2-yl)methyl)benzamide;
2-methoxy-4-(4-methylpiperazin-1-yl)-N-((5-(thiophen-2-yl)-1,3,4-oxadiazol-2-methyl)benzamide;
2-methoxy-4-morpholino-N-((5-(thiazol-5-yl)-1,3,4-oxadiazol-2-y1)methyl)benzamide;
N-((5-(isothiazol-5-yl)-1,3,4-oxadiazol-2-yl)methyl)-2-methoxy-4-morpholinobenzamide;
2-methoxy-4-morpholino-N((5-(thiazol-2-yl)-1,3,4-oxadiazol-2-yl)methyl)benzamide;
N-((5-(5-chlorothiophen-2-yl)-1,3,4-oxadiazol-2-yl)methyl)-2-methoxy-4-morpholinohenzamide;
2-methoxy-4-morpholino-N-(2-(5-(thiophen-2-yl)-1,3,4-oxadiazol-2-yl)propan-2-yl)benzamide;
2-methoxy-4-morpholino-N-(1-(5-(thiophen-2-yl)-1,3,4-oxadiazol-2-yl)ethyl)benzamide;
2-methoxy-N-methyl-4-morpholino-N-(2-(5-(thiophen-2-yl)-1,3,4-oxadiazol-2-yl)propan-2-yl)benzamide;
2-methoxy4-(2-morpholinoethoxy)-N-((5-(thiophen-2-yl)-1,3,4-oxadiazol-2-yl)methyl)benzamide;
4-(2-hydroxyethoxy)-2-methoxy-N-((5-(thiophen-2-yl)-1,3,4-oxadiazol-2-yl)methyl)benzamide;
2-methoxy-4-(2-methoxyethoxy)-N-((5-(thiophen-2-yl -1,3,4-oxadiazol-2-yl)methyl)benzamide;
N-(2-methoxy-4-morpholinophenyl)-5-(thiophen-2-yl)-1,3,4-oxadiazole-2-carboxamide;
2-methoxy-4-((1-methylpyrrolidin-3-yl)amino)-N-((5-(thiophen-2-yl)-1,3,4-oxadiazol-2-yl)methyl)benzamide;
2-methoxy-4-(2-(methylamino)ethyl)amino)-N-((5-(thiophen-2-yl)-1,3,4-oxadiazol-2-yl)methyl)benzamide;
4-(3-hydroxypyrrolidin-1-yl)-2-methoxy-N-((5-(thiophen-2-yl)-1,3,4-oxadiazol-2-yl)methyl)benzamide;
4-((2-hydroxyethyl)amino)-2-methoxy-N-((5-(thiophen-2-yl)-1,3,4-oxadiazial-2-yl)methyl)benzamide;
2-methoxy-4-(2-(methylamino)ethoxy)-N-((5-(thiophen-2-yl)-1,3,4-oxadiazol-2-yl)methyl)benzamide;
2-methoxy-4-(pyrrolidin-3-yloxy)-N-((5-(thiophen-2-yl)-1,3,4-oxadiazol-2-yl)methyl)benzamide;
2-methoxy-4-((1-methylpyrrolidin-3-yl)oxy)-N-((5-(thiophen-2-yl)-1,3,4-oxadiazol-2-yl)methyl)benzamide;
4-(2-hydroxypropan-2-yl)-2-methoxy-N-((5-(thiophen-2-yl)-1,3,4-oxadiazol-2-yl)methyl)benzamide;
4-(2-hydroxy-2-methylpropyl)-2-methoxy-N-((5-(thiophen-2-yl)-1,3,4-oxadiazol-2-yl)methyl)benzamide;
2-methoxy-4-(piperidin-1-ylmethyl)-N-((5-(thiophen-2-yl)-1,3,4-oxadiazol-2-yl)methyl)benzamide;
2-methoxy4-(morpholinomethyl)-N-((5-(thiophen-2-yl)-1,3,4-oxadiazol-2-yl)methyl)benzamide.

2. A pharmaceutical composition, comprising a compound of claim 1, or a pharmaceutically acceptable salt thereof; and a pharmaceutically acceptable carrier or excipient.

3. A method of treating a disease mediated by MIF in a subject in need thereof, comprising administering to the subject, a therapeutically effective amount of a compound of claim 1, or a pharmaceutically acceptable salt thereof.

4. The method of claim 3, wherein the disease mediated by MIF is
tumor selected from glioblastomas, lung cancer, breast cancer, gastric cancer, bladder cancer, melanoma;
intlammatoly disease selected from chronic obstructive pulmonary disease (COPD), pneumonia;
autoimmune disease selected from rheumatoid arthritis (RA), multiple sclerosis (MS) systemic lupus erythematosus (SLE).

5. The method of claim 3, wherein the subject is human.

6. A method of inhibiting MIF expression, production and/or secretion in a subject in need thereof, the method comprising administering to the subject, a pharmaceutically effective amount of a compound of claim 1, or a pharmaceutically acceptable salt thereof.

7. The method of claim 6, wherein the suject is human.

8. A method of inhibiting MIF tautomerase catalytic activity in a subject in need thereof, the method comprising administering to the subject, a pharmaceutically effective amount of a compound of claim 5, or a pharmaceutically acceptable salt thereof.

9. The method of claim 8, wherein the subject is human.

10. A method of inhibiting MIF expression, production and/or secretion in a cell, comprising contacting the cell with a pharmaceutically effective amount of a compound of claim 1, or a pharmaceutically acceptable salt thereof.

11. A method of inhibiting MIF tautomerase catalytic activity in a cell, comprising contacting the cell with a pharmaceutically effective amount of a compound of claim 1, or a pharmaceutically acceptable salt thereof.

12. A compound of claim 1, wherein the compounds is 2-methoxy-4-morpholino-N-((5-thiophen-2-yl)-1,3,4-oxadiazol-2-yl)methyl)benzamide.

13. A compound of claim 1, wherein the compounds is 2-methoxy-N-methyl-4-morpholino-N-((5-thiophen-2-yl)-1,3,4-oxadiazol-2-yl)methyl)benzamide.

14. A compound of claim 1, wherein the compound is N-ethyl-2-methoxy-4-morpholino-N-((5-(thiophen-2-yl)-1,3,4-oxadiazol-2-yl)methyl)benzamide.

* * * * *